United States Patent
Richards-Kortum et al.

(10) Patent No.: US 6,258,576 B1
(45) Date of Patent: *Jul. 10, 2001

(54) DIAGNOSTIC METHOD AND APPARATUS FOR CERVICAL SQUAMOUS INTRAEPITHELIAL LESIONS IN VITRO AND IN VIVO USING FLUORESCENCE SPECTROSCOPY

(75) Inventors: Rebecca Richards-Kortum, Austin, TX (US); Nirmala Ramanujam, Philadelphia, PA (US); Anita Mahadevan-Jansen, Austin; Michele Follen Mitchell, Houston, both of TX (US)

(73) Assignee: Board of Regents, the University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/666,021

(22) Filed: Jun. 19, 1996

Related U.S. Application Data

(63) Continuation-in-part of application No. 08/403,446, filed on Mar. 14, 1997.

(51) Int. Cl.$^7$ .............................. G01N 21/64; A61B 5/00
(52) U.S. Cl. ............................................ 435/172; 425/288
(58) Field of Search .............................. 435/172; 425/288

(56) References Cited

U.S. PATENT DOCUMENTS

| | | | |
|---|---|---|---|
| 4,556,057 | 12/1985 | Hiruma et al. | 128/303.1 |
| 4,648,892 | 3/1987 | Kittrell et al. | 65/4.21 |
| 4,675,529 | 6/1987 | Kushida | 250/458.1 |
| 4,755,684 | 7/1988 | Leiner et al. | 250/461.1 |
| 4,832,483 | 5/1989 | Verma | 356/39 |
| 4,913,142 | 4/1990 | Kittrell et al. | 606/7 |
| 4,967,745 | 11/1990 | Hayes et al. | 128/303.1 |
| 4,973,848 | 11/1990 | Kolobanov et al. | 250/458.1 |
| 5,003,977 | 4/1991 | Suzuki et al. | 128/633 |
| 5,009,655 | 4/1991 | Daignault, Jr. et al. | 606/7 |
| 5,014,707 | 5/1991 | Schwarz et al. | 128/633 |
| 5,026,368 | 6/1991 | Adair | 606/15 |
| 5,034,010 | 7/1991 | Kittrell et al. | 606/15 |
| 5,036,853 | 8/1991 | Jeffcoat et al. | 128/634 |
| 5,038,039 | 8/1991 | Wong et al. | 250/339 |
| 5,062,431 | 11/1991 | Potter | 128/665 |
| 5,092,331 | 3/1992 | Nakamura et al. | 128/634 |
| 5,104,392 | 4/1992 | Kittrell et al. | 606/15 |
| 5,106,387 | 4/1992 | Kittrell et al. | 606/15 |
| 5,192,278 | 3/1993 | Hayes et al. | 606/15 |
| 5,199,431 | 4/1993 | Kittrell et al. | 128/634 |
| 5,251,613 | 10/1993 | Adair | 128/6 |
| 5,280,788 | 1/1994 | Janes et al. | 128/665 |
| 5,290,275 | 3/1994 | Kittrell et al. | 606/15 |
| 5,293,872 | 3/1994 | Alfano et al. | 128/664 |
| 5,304,173 | 4/1994 | Kittrell et al. | 606/15 |
| 5,318,023 | 6/1994 | Vari et al. | 128/633 |
| 5,345,941 | 9/1994 | Rava et al. | 128/665 |
| 5,348,003 | 9/1994 | Caro | 128/633 |
| 5,348,018 | 9/1994 | Alfano et al. | 128/665 |
| 5,408,996 | 4/1995 | Salb | 128/633 |
| 5,419,323 | 5/1995 | Kittrell et al. | 128/653.1 |
| 5,421,337 | 6/1995 | Richards-Kortum et al. | 128/665 |
| 5,421,339 | 6/1995 | Ramanujam et al. | 128/665 |
| 5,421,346 | 6/1995 | Sanyal | 128/750 |
| 5,450,857 | 9/1995 | Garfield et al. | 128/778 |
| 5,452,723 | 9/1995 | Wu et al. | 128/664 |
| 5,467,767 | 11/1995 | Alfano et al. | 128/665 |
| 5,507,287 | 4/1996 | Palcic et al. | 128/633 |
| 5,552,134 | 9/1996 | Morgan et al. | 424/9.61 |

FOREIGN PATENT DOCUMENTS

| | | | |
|---|---|---|---|
| 0 608 987 A1 | 8/1994 | (EP) | G01N/33/574 |
| 1151436 | 6/1989 | (JP) | A61B/5/00 |
| WO 88/05908 | 8/1988 | (WO) | G01N/15/14 |
| WO 90/06718 | 6/1990 | (WO) . | |
| WO 90/12536 | 11/1990 | (WO) . | |
| WO 94/26168 | 11/1994 | (WO) . | |
| WO 95/26673 | 10/1995 | (WO) | A61B/5/00 |
| WO 96/28084 | 9/1996 | (WO) . | |
| WO 96/30746 | 10/1996 | (WO) . | |

OTHER PUBLICATIONS

Alfano et al., "Laser Induced Fluorescence Spectroscopy from Native Cancerous and Normal Tissue," *IEEE Journal of Quantum Electronics*, QE–20(12):1507–1511, 1984.

Avrillier et al., "XEC1 Excimer Laser–Induced Autofluorescence Spectroscopy for Human Cerebral Tumours Diagnosis: Preliminary Study," *SPIE*, 1894:177–186, 1993.

Bergeron et al., "Complete Fluorescence Spectrum of a Normal and Atherosclerotic Aorta," *Can. J. Phys.*, 66:1035–1039, 1988.

(List continued on next page.)

*Primary Examiner*—Geetha P. Bansal
(74) *Attorney, Agent, or Firm*—Fulbright & Jaworski, LLP

(57) ABSTRACT

The present invention involves the use of fluorescence spectroscopy in the diagnosis of cervical cancer and pre-cancer. Using multiple illumination wavelengths, it is possible to (i) differentiate normal or inflamed tissue from squamous intraepithelial lesions (SILs) and (ii) to differentiate high grade SILs from non-high grade SILs. The detection may be performed in vitro or in vivo. Multivariate statistical analysis was employed to reduce the number of fluorescence excitation-emission wavelength pairs needed to re-develop algorithms that demonstrate a minimum decrease in classification accuracy. Fluorescence at excitation-emission wavelength pairs was used to redevelop and test screening and diagnostic algorithms that have a similar classification accuracy to those that employ fluorescence emission spectra at three excitation wavelengths. Both the full-parameter and reduced-parameter screening algorithms discriminate between SILs and non-SILs with a similar specificity and a substantially improved sensitivity relative to Pap smear screening and differentiate high grade SILs from non-high grade SILs.

35 Claims, 10 Drawing Sheets

OTHER PUBLICATIONS

Bosshart et al., "Fluorescence Spectroscopy for Identification of Atherosclerotic Tissue," *Cardiovascular Research*, 26:620–625, 1992.

Bottiroli et al., "Natural Fluorescence of Normal and Neoplastic Human Colon: A Comprehensive "ex vivo" Study," *Lasers in Surgery & Medicine*, 16(1):48–60, 1995.

Clarke et al., "Spectroscopic Characterization of Cardiovascular Tissue," Lasers in Surgery and Medicine, 8:45–59, 1988.

Deckelbaum et al., "Discrimination of Normal and Atherosclerotic Aorta by Laser–Induced Fluorescence," *Lasers in Surgery and Medicine*, 7:330–335, 1987.

Deckelbaum et al., "In–vivo Fluorescence Spectroscopy of Normal and Atherosclerotic Arteries," *SPIE*, 906:314–319, 1988.

D'Hallewin et al., "In Vivo Fluorescence Detection of Human Bladder Carcinoma Without Sensitizing Agents," *Journal of the American Paraplegia Society*, 17(4):161–164, 1994.

Edholm et al., Tissue Identification During Needle Puncture by Reflection Spectrophotometry *Biol. Engng.*, 6:409–413, 1968.

Fiarman et al., "Differences in Laser–Induced Autofluorescence between Adenomatous and Hyperplastic Polyps and Normal Confocal Mucosa by Confocal Microscopy," *Digestive Disease & Sciences*, 40(6):11261–1268, 1995.

Fitzmaurice et al., "Argon Ion Laser–Excited Autofluorescence in Normal and Atherosclerotic Aorta and Coronary Arteries: Morphologic Studies," *American Heart Journal*, 118(5)(1):1028–1037, 1989.

Frank et al., "Characterization of Human Breast Biopsy Specimens with Near–IR Raman Spectroscopy," *Anal. Chem.*, 66:319–326, 1994.

Ghadially and Neish, "Porphyrin Fluorescence of Experimentally Produced Squamous Cell Carcinoma," *Nature*, 188:1124, 1960.

Ghadially et al., "Mechanisms Involved in the Production of Red Fluorescence of Human and Experimental Tumours," *Path. Bact.*, 85:77–92, 1963.

Glassman et al., "Excitation Spectroscopy of Malignant and Non–malignant Gynecological Tissues," *Lasers in the Life Sciences*, 6(2):99–106, 1994.

Glassman et al., "Time Resolved and Steady State Fluorescence Spectroscopy from Normal and Malignant Cultured Human Breast Cell Lines," *Lasers in the Life Sciences*, 6(2):91–98, 1994.

Gmitro et al., "Measurement Depth of Laser–Induced Tissue Fluorescence with Application to Laser Angioplasty," *Applied Optics*, 27(9):1844–1849, 1988.

Harries et al., "Diagnostic Imaging of the Larynx: Autofluorescence of Laryngeal Tumours Using the Helium–Cadmium Laser," *The Journal of Laryngology and Otology*, 109:108–110, 1995.

Hoyt et al., "Remote Biomedical Spectroscopic Imaging of Human Artery Wall," *Lasers in Surgery and Medicine*, 8:1–9, 1988.

Kittrell et al., "Diagnosis of Fibrous Arterial Atherosclerosis Using Fluorescence," *Applied Optics*, 24(15):2280–2281, 1985.

Kluftinger et al., "Detection of Squamous Cell Cancer and Pre–cancerous Lesions by Imaging of Tissue Autofluorescence in the Hamster Cheek Pouch Model," *Surgical Oncology*, 1:183–188, 1992.

Laifer et al., "Biochemical Basis for the Difference Between Normal and Atherosclerotic Arterial Fluorescence," *Circulation*, 80(6):1893–1901, 1989.

Lam et al., "Detection of Dysplasia and Carcinoma is situ with a Lung Imaging Fluorescence Endoscope Device," *J. Thorac Cardiovasc. Surg.*, 105:1035–1040, 1993.

Leon et al., "Human Arterial Surface Fluorescence: Atherosclerotic Plaque Identification and Effects of Laser Atheroma Ablation," *JACC*, 12(1):94–102, 1988.

Liu et al., "Raman, Fluorescence, and Time–Resolved Light Scattering as Optical Diagnostic Techniques to Separate Diseased and Normal Biomedical Media," *J. Photochem. Photobiol. B: Biol.*, 16:187–209, 1992.

Lohmann et al., "In situ Differentiation Between Nevi and Malignant Melanomas by Fluorescence Measurements," *Naturwissenschaften*, 78:456–457, 1991.

Lohmann et al., "Fluorescence Studies on Lung Tumors," *Z. Naturforsch*, 45c:1063–1066, 1990.

Lohmann and Künzel, "Fluorescence Tomographical Studies on Breast Tissue with Cancer," *Naturwissenschaften*, 77:476–478, 1990.

Lohman, W., "Native Fluorescence of Unstained Cryo–sections of the Skin with Melanomas and Nevi," *Naturwissenschaften*, 76:424–426, 1989.

Mahadevan et al., "Optical Techniques for the Diagnosis of Cervical Precancers: A Comparison of Raman and Fluorescence Spectroscopies," *SPIE*, 2388:110–120, 1995.

Mahadevan et al., "Study of the Fluorescence Properties of Normal and Neoplastic Human Cervical Tissue," *Lasers in Surgery and Medicine*, 13:647–655, 1993.

Manoharan et al., "Ultraviolet Resonance Raman Spectroscopy for Detection of Colon Cancer," *Lasers in Life Sciences*, 6:217–227, 1995.

Manoharan et al., "Laser–induced Fluorescence Spectroscopy of Colonic Dysplasia: Prospects for Optical Histological Analysis," *SPIE*, 2388:417–421, 1995.

Montán and Strömblad, "Spectral Characterization of Brain Tumors Utilizing Laser–Induced Fluorescence," *Lasers in Life Sciences*, 1(4):275–285, 1987.

Mosier–Boss et al., "Fluorescence Rejection in Raman Spectroscopy by Shifted–Spectra, Edge Detection, and FFT Filtering Techniques," *Applied Spectroscopy*, 49(5):630–638, 1995.

Nishioka, "Laser–Induced Fluorescence Spectroscopy," *Experimental and Investigational Endoscopy*, 42(2):313–326, 1994.

Oraevsky et al., "XeCl Laser–Induced Fluorescence of Atherosclerotic Arteries. Spectral Similarities Between Lipid–Rich Lesions and Peroxidized Lipoproteins," *Circulation Research*, 72:;84–90, 1993.

Ozaki et al., "Biomedical Application of Near–Infrared Fourier Transform Raman Spectroscopy, Part I: The 1064–nm Excited Raman Spectra of Blood and Met Hemoglobin," *Applied Spectroscopy*, 46(3):533–536, 1992.

Palcic et al., "Detection and Localization of Early Lung Cancer by Imaging Techniques," *Chest*, 99:742–743, 1991.

Papazoglou et al., "Laser–Induced Fluorescence Detection of Cardiovascular Atherosclerotic Deposits via Their Natural Emission and Hypocrellin (HA) Probing," *J. Photochem. Photobiol. B: Biol.*, 22:139–144, 1994.

Ramanujam et al., "In vivo Diagnosis of Cervical Intraepithelial Neoplasia Using 337–nm–Excited Laser–Induced Fluorescence," *Proc. Natl. Acad. Sci. USA*, 91:10193–10197, 1994.

Ramanujam et al., "Fluorescence Spectroscopy: A Diagnostic Tool for Cervical Intraepithelial Neoplasia (CIN)," *Gynecologic Oncology*, 52:31–38, 1994.

Richards–Kortum et al., "476 nm Excited Laser–Induced Fluorescence Spectroscopy of Human Coronary Arteries: Applications in Cardiology," *American Heart Journal*, 122(4)(1):1141–1150, 1991.

Richards–Kortum et al., "Spectral Diagnosis of Atherosclerosis Using an Optical Fiber Laser Catheter," *American Heart Journal*, 118(2):381–391, 1989.

Richards–Kortum et al., "A One–Layer Model of Laser–Induced Fluorescence for Diagnosis of Disease in Human Tissue: Applications to Atherosclerosis," *IEEE Transactions on Biomedical Engineering*, 36(12):1222–1232, 1989.

Richards–Kortum et al., "Survey of the UV and Visible Spectroscopic Properties of Normal and Atherosclerotic Human Artery Using Fluorescence EEMS," In *Optronic Techniques in Diagnostic and Therapeutic Medicine*, ed. R. Pratesi, Plenum, 1991, pp. 129–138.

Richards–Kortum et al., "A Model for Extraction of Diagnostic Information from Laser Induced Fluorescence Spectra of Human Artery Wall," *Spectrochimica Acta*, 45A(1):87–93, 1989.

Römer et al., "Laser–Induced Fluorescence Microscopy of Normal Colon and Dysplasia in Colonic Adenomas: Implications for Spectroscopic Diagnosis," *The American Journal of Gastroenterology*, 90(1):81–87, 1995.

Sartori et al., Autofluorescence Maps of Atherosclerotic Human Arteries–A New Technique in Medical Imaging, *IEEE Journal of Quantum Electronics*, QE–23(10):1794–1797, 1987.

Schomacker et al., "Ultraviolet Laser–Induced Fluorescence of Colonic Polyps," *Gastroenterology*, 102:1155–1160, 1992.

Sterenborg et al., "In vivo Fluorescence Spectroscopy and Imaging of Human Skin Tumours," *Lasers in Medical Science*, 9:191–201, 1994.

van Gemert et al., "Optical Properties of Human Blood Vessel Wall and Plaque," *Lasers in Surgery and Medicine*, 5:235–237, 1985.

Verbunt et al., "Characterization of Ultraviolet Laser–Induced Autofluorescence of Ceroid Deposits and Other Structures in Atherosclerotic Plaques as a Potential Diagnostic for Laser Angiosurgery," *American Heart Journal*, 123(1):208–216, 1992.

Yuanlong et al., "Characteristic Autofluorescence for Cancer Diagnosis and Its Origin," *Lasers in Surgery and Medicine*, 7:528–532, 1987.

Zeng et al., "Autofluorescence Distribution in Skin Tissue Revealed by Micropectrophotometer Measurements," *SPIE*, 1876:129–135, 1993.

Zeng et al., "A Computerized Autofluorescence and Diffuse Reflective Spectroanalyser System for in vivo Studies," *Phys. Med. Biol.*, 38:231–240, 1993.

International Search Report dated Oct. 17, 1997 (TUUT:006P).

DIAGNOSTIC METHOD AND APPARATUS FOR CERVICAL SQUAMOUS INTRAEPITHELIAL LESIONS IN VITRO AND IN VIVO USING FLUORESCENCE SPECTROSCOPY

This application is a continuation-in-part of U.S. Ser. No. 08/403,446, filed Mar. 14, 1997.

BACKGROUND OF THE INVENTION

I. Field of the Invention

The invention relates to optical methods and apparatus used for the diagnosis of cervical precancers.

II. Related Art

There has been a significant decline in the incidence of advanced cervical cancer over the last 40 years, primarily due to the development of organized programs that target early detection of its curable precursor, cervical Squamous Intraepithelial Lesion (SIL) (SILs consist of Cervical Intraepithelial Neoplasia (CIN) and Human Papilloma Viral (HPV) infection) [1]. Even though organized screening (Pap smear) and diagnostic (colposcopy) programs are currently in place, approximately 15,900 new cases of cervical cancer and 4,900 cervical cancer related deaths were reported in 1995, in the United States alone [2]. Currently, 24.5% of women with cervical cancer are under the age of 35 years, and the incidence continues to increase for women in this age group [1]. The continuing morbidity and mortality rate related to cervical cancer necessitates an improvement in the accuracy and efficacy of current detection modalities.

The Pap smear is the primary screening tool for the detection of cervical cancer and its precursor [3]. In a Pap test, a large number of cells obtained by scraping the cervical epithelium are smeared onto a slide which is then fixed and stained for cytologic examination. Each smear is then examined under a microscope for the presence of neoplastic cells [4]. The Pap smear's reported sensitivity and specificity range from 11–99% and 14–97%, respectively. Like many screening tests in an asymptomatic population, the Pap smear is unable to achieve a concurrently high sensitivity and high specificity [5]. The accuracy of the Pap smear is limited by both sampling and reading errors [6]. Approximately 60% of false-negative smears are attributed to insufficient sampling; the remaining 40% are due to reading errors. Because of the monotony and fatigue associated with reading Pap smears (50,000–300,000 cells per slide), the American Society of Cytology has proposed that a cytotechnologist should be limited to evaluating no more than 12,000 smears annually [7]. As a result, accurate Pap smear screening is labor intensive and requires highly trained professionals.

A patient with a Pap smear interpreted as indicating the presence of SIL is generally recommended for follow up with a diagnostic procedure called colposcopy [3]. During a colposcopic examination, the cervix is stained with acetic acid and viewed through a low power microscope to identify potential pre-cancerous sites; suspicious sites are biopsied and then histologically examined to confirm the presence, extent and severity of the SIL [8]. A patient who has high grade SIL (HG SIL) (which consists of CIN II and/or CIN III) is usually treated, whereas a patient diagnosed with low grade SIL (LG SIL) (which consists of HPV and/or CIN I) is generally followed further using colposcopy [3].

Colposcopic examination and tissue biopsy in expert hands maintains a high sensitivity (80–90%), at the expense of a significantly low specificity (50–60%) [9]. A poor specificity represents unnecessary biopsy of tissues which do not contain cervical pre-cancer. In spite of the poor specificity of this technique, extensive training is required to achieve this skill level. All biopsy specimens require histologic evaluation and, therefore, diagnosis is not immediate. The disconnection between colposcopic assessment and biopsy and definitive treatment is of particular concern in the management of economically disadvantaged patients who may not return for treatment, particularly since cervical cancer precursors are more prevalent in groups of lower socio-economic status [1].

Fluorescence spectroscopy is a technique that has the potential to improve the accuracy and efficacy of cervical pre-cancer screening and diagnosis. Fluorescence spectroscopy has the capability to quickly, non-invasively and quantitatively probe the biochemical and morphological changes that occur as tissue becomes neoplastic. The altered biochemical and morphological state of the neoplastic tissue is reflected in the spectral characteristics of the measured fluorescence. This spectral information can be correlated to tissue histopathology, the current "gold standard" to develop clinically effective screening and diagnostic algorithms. These mathematical algorithms can be implemented in software, thereby enabling automated, fast, non-invasive and accurate pre-cancer screening and diagnosis in the hands of non-experts.

Although a complete understanding of the quantitative information contained within a tissue fluorescence spectrum has not been achieved, many groups have applied fluorescence spectroscopy for real-time, non-invasive, automated characterization of tissue pathology. Characterization of tissue pathology using auto-fluorescence [10–23] as well as photosensitizer induced fluorescence [24–27] to discriminate between diseased and non-diseased human tissues in vitro and in vivo has been described in a variety of tissues.

Auto-fluorescence spectra of normal tissue, intraepithelial neoplasia and invasive carcinoma have been measured from several organ sites in vivo [13–17]. In vivo studies of the human colon at 370 nm excitation [13] indicated that a simple algorithm based on fluorescence intensity at two emission wavelengths can be used to differentiate normal colon and adenomatous polyps with a sensitivity and specificity of 100% and 97%, respectively. Shomacker et al. [14] conducted similar studies in vivo at 337 nm excitation and demonstrated that a multivariate linear regression algorithm based on laser induced fluorescence spectra can be used to discriminate between normal colon and colonic polyps with a similarly high sensitivity and specificity. Lam et al. developed a bronchoscope which illuminates tissue at 442 nm excitation and produces a false color image in near real-time which represents the ratio of fluorescence intensities at 520 nm (green) and 690 nm (red) [16,17]. In vivo studies demonstrated that the ratio of red to green auto-fluorescence is greater in normal bronchial tissues than in abnormal bronchial tissues [16]. In a trial with 53 patients, the sensitivity of fluorescence bronchoscopy was found to be 72%, as compared to 50% for conventional white light bronchoscopy [17].

Nonetheless, a reliable diagnostic method with improved diagnostic capability for use in vitro and in vivo is needed to allow faster, more effective patient management and potentially further reduce mortality.

SUMMARY OF THE INVENTION

The present invention demonstrates that fluorescence spectroscopy can be applied, both in vitro and in vivo, to the diagnosis of cervical tissue abnormalities including the clinical detection of cervical precancer.

In a first exemplary embodiment, there is provided a method of detecting tissue abnormality in a tissue sample comprising the steps of (i) providing a tissue sample; (ii) illuminating said sample with electromagnetic radiation wavelengths of about 337 nm, about 380 nm and about 460 nm to produce three fluorescence intensity spectra; (iii) detecting a plurality of emission wavelengths from said fluorescence intensity spectra; and (iv) establishing from said emission wavelengths a probability that said sample is abnormal. The illumination wavelengths are advantageously in the ranges of 317–357 nm, 360–400 nm and 440–480 nm. The method may further comprise preprocessing data at the emission wavelengths to reduce inter-sample and intra-sample variation. The establishing step may comprise normalizing the spectra relative to a maximum intensity within the spectra. Optionally, the establishing step does not comprise mean-scaling the spectra.

Emission wavelengths may be selected at about 410 nm, about 460 nm, about 510 nm and about 580 nm for an illumination of about 337 nm; at about 460 nm, about 510 nm, about 580 nm, about 600 nm and about 640 nm for an illumination of about 380 nm; and at about 510, bout 580 nm, about 600 nm, about 620 nm, about 640 nm and about 660 nm for an illumination of about 460 nm.

In various embodiments, the method may use illumination in vitro or in vivo. Where the method is in vitro, the providing step may comprise obtaining the tissue sample by biopsy. Further, the in vitro method may comprise generating a monolayer cell touch preparation or a pellet and ethanol fixation of the tissue sample. The illumination may comprise illuminating the sample substantially normal to a surface of the sample, and wherein the detecting step comprises, detecting the spectra at an angle of approximately 20° from normal.

The method is capable of distinguishing tissues as follows: normal squamous and abnormal tissue; normal columnar epithelium and abnormal tissue; inflamed and abnormal tissue; low grade SIL and high grade SIL tissue; and normal and high grade SIL tissue.

The present invention also comprises a method of developing a model for differentiating normal from abnormal tissue in a tissue sample comprising the steps of (i) providing a plurality of tissue samples; (ii) illuminating the samples with electromagnetic radiation wavelengths of about 337 nm, about 380 nm and about 460 nm to produce three fluorescence intensity spectra; (iii) detecting a plurality of emission wavelengths from the fluorescence intensity spectra; (iv) forming a set of principal components from the spectra, said principal components being defined as providing statistically significant differences between normal tissue and various forms of abnormal tissue; and (v) subjecting said principal components to logistic discrimination to develop a relevant mathematical model. Again, the illumination wavelengths may be in the ranges of 317–357 nm, 360400 nm and 440–480 nm.

In still another embodiment, there is provided a method of detecting tissue abnormality in a tissue sample comprising the steps of (i) providing a tissue sample; (ii) illuminating the sample with electromagnetic radiation wavelengths of about 337 nm, about 380 nm and about 460 nm to produce three fluorescence intensity spectra; (iii) detecting a plurality of emission wavelengths from said fluorescence intensity spectra; and (iv) establishing from principal components PC 1, PC3 and PC7 of step (iii) a probability that the sample is abnormal. Alternatively, the principal components are PC1, PC2, PC4 and PC5 or PC1, PC3 PC6 and PC8.

In still yet another embodiment, there is provided a method of detecting tissue abnormality in a subject in vivo comprising the steps of (i) illuminating a tissue sample in vivo with a plurality of electromagnetic radiation wavelengths to produce a plurality of fluorescence intensity spectra; (ii) detecting a plurality of emission wavelengths from the fluorescence intensity spectra; and (iii) establishing from the emission wavelengths a probability that the sample is abnormal. The illumination wavelengths advantageously include at least three wavelengths having the ranges of about 317–357 nm, about 360–400 nm and about 440–480 nm. The method may further comprise the step of preprocessing data at the emission wavelengths to reduce inter-patient and intra-patient variation.

In still yet another embodiment, there is provided a method for diagnosing cervical precancer in a patient comprising the steps of (i) illuminating cervical tissue of the patient with a plurality of electromagnetic radiation wavelengths to produce a plurality of fluorescence intensity spectra; (ii) detecting a plurality of emission wavelengths from said fluorescence intensity spectra; (iii) comparing the plurality of emission wavelengths from the patient with known emission wavelengths for normal tissue; and (iv) making a diagnostic prediction of the condition the cervical tissue.

In still yet another embodiment, the method of fluorescent spectroscopy is coupled with illuminating the sample with an electromagnetic radiation wavelength in the near infrared sufficient to produce a Raman spectrum and detecting a Raman spectrum therefrom. The near infrared illumination wavelength is about 789 nm. Advantageously, the emission frequencies are shifted about 626, 818, 978, 1070, 1175, 1246, 1330, 1454 and 1656 $cm^{-1}$ from the illumination wavelength. In a particular embodiment, at least one of the emission frequencies is associated with compound selected from the group consisting of collagen, phopholipids and glucose-1-phosphate.

The present invention also contemplates an apparatus for detecting tissue abnormality, comprising, a light source for emitting a plurality of electromagnetic radiation wavelengths, and a probe connected to the light source, the probe being adapted to apply the plurality of radiation wavelengths to tissue under test and to gather fluorescence emitted from the tissue under test. The apparatus also, includes means, connected to probe, for detecting at least one fluorescence spectrum emitted from the tissue under test, and a programmed computer connected to the detection means, for processing the at least one fluorescence spectrum according to a predetermined algorithm to establish a probability that the tissue under test is abnormal.

The light source may comprise a nitrogen pumped laser, and the plurality of electromagnetic radiation wavelengths may be about 337 nm, about 380 nm and about 460 nm.

The apparatus may further comprise a polychromator connected between the probe and the detection means.

The probe may include emission optical fibers for applying the plurality of electromagnetic wavelengths to the tissue under test, collection optical fibers for gathering the fluorescence emitted from the tissue under test, and a shield overlying ends of the excitation optical fibers and collection optical fibers.

The predetermined algorithm may include principal components that predict statistically relevant differences between fluorescence emission wavelengths from normal and abnormal tissues for the plurality of applied electromagnetic radiation wavelengths.

Finally, the abnormal tissues that are predicted may include inflamed tissue, low grade SIL and high grade SIL.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein.

(FIG. 3A) Original and corresponding, (FIG. 3B) normalized and (FIG. 3C) normalized, mean-scaled spectra at 337 nm excitation from a typical patient.

(FIG. 4A) Original and corresponding, (FIG. 4B) normalized and (FIG. 4C) normalized, mean-scaled spectra at 380 nm excitation from the same patient. 5

(FIG. 5A) Original and corresponding, (FIG. 5B) normalized and (FIG. 5C) normalized, mean-scaled spectra at 460 nm excitation from the same patient.

DETAILED DESCRIPTION OF THE INVENTION

I. The Present Invention

Figure 1:
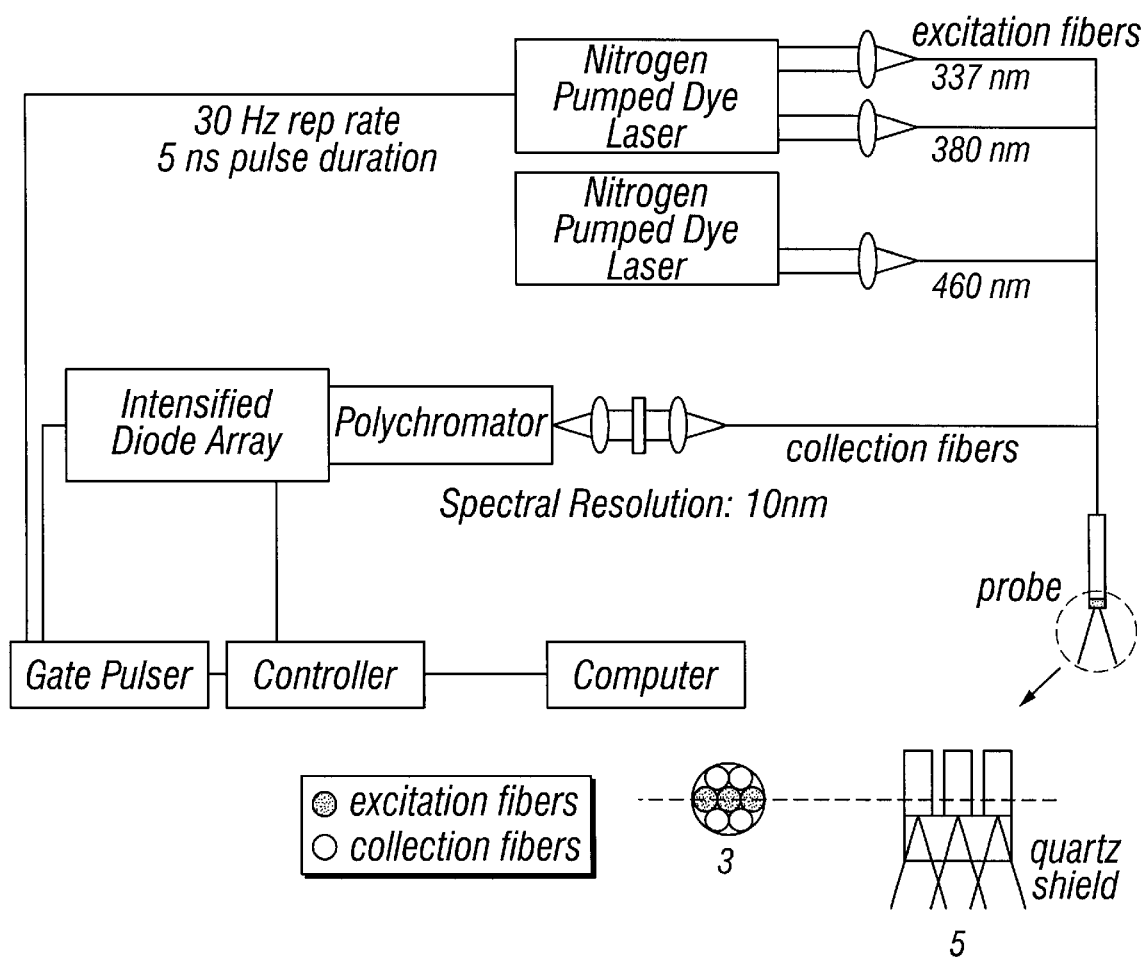
FIG. 1. A schematic of the portable fluorimeter used to measure cervical tissue fluorescence spectra at three excitation wavelengths.

This present invention provides for the development and application of a detection technique for human cervical pre-cancer, both in vitro and in vivo, based on laser induced fluorescence spectroscopy. Fluorescence spectra from 381 cervical samples in 95 patients were acquired at three excitation wavelengths: 337, 380 and 460 nm. A general multivariate statistical algorithm is then used to analyze and extract clinically useful information from tissue spectra acquired in vivo. The present invention includes a screening algorithm to discriminate between SILs and-non SILs (normal squamous and columnar epithelia and inflammation); and a diagnostic algorithm to differentiate high grade SILs from non-high grade SILs (low grade SILs, normal epithelia and inflammation). The retrospective and prospective accuracy of both the screening and diagnostic algorithms is compared to the accuracy of Pap smear screening [5] and to colposcopy in expert hands [9].

The general multivariate statistical algorithm was developed and tested using cervical tissue spectra acquired at 337 nm excitation from 476 cervical sites in 92 patients. This algorithm could be used to differentiate SILs and normal squamous tissues with an average sensitivity and specificity of 91%±2 and 78%±3, respectively. Spectra of normal columnar tissues and inflammation were indistinguishable from those of SILs at this single excitation wavelength. Furthermore, a multivariate statistical algorithm based solely on spectra at 337 nm excitation only could not discriminate between high grade SILs and low grade SILs effectively.

However, multivariate statistical analysis of cervical tissue fluorescence spectra acquired in vivo at 380 nm and 460 nm excitation from a subset of the 92 patients indicated that spectra at these excitation wavelengths can overcome the limitations of spectra at 337 nm excitation. Spectra at 380 nm excitation from 165 sites in a first group of 40 patients could be used to differentiate SILs from normal columnar epithelia and inflammation with a sensitivity and specificity of 77%±1 and 72%±9, respectively; spectra at 460 nm excitation from 149 sites in a second group of 24 patients could be used to differentiate high grade SILs from low grade SILs with a sensitivity and specificity of 80%±4 and 76%±5, respectively.

There are two principal limitations of previous studies using fluorescence spectroscopy in the diagnosis of precancers. A first limitation is that fluorescence spectra were not acquired at all three excitation wavelengths (337, 380 and 460 nm) from every patient in the study. Therefore, analysis of spectral data from these studies did not indicate if the classification accuracy of each of the three constituent algorithms developed using spectra at a single excitation wavelength could be improved by utilizing tissue spectra at all three excitation wavelengths. A second limitation of these studies is that the accuracy of composite screening and diagnostic algorithms utilizing a combination of the constituent algorithms could not be evaluated since tissue spectra were not available at all three excitation wavelengths from the same group of patients.

In accordance with one embodiment, an algorithm based on normalized, mean-scaled spectra at 337 nm excitation can be used to differentiate between SILs and normal squamous tissues, while a second algorithm based on similarly pre-processed spectra at 380 nm excitation can be used to differentiate SILs from normal columnar tissues and samples with inflammation. A third algorithm, based on normalized tissue spectra at 460 nm excitation, can be used to discriminate between low grade SILs and high grade SILs.

Thus, a first goal of this analysis is to evaluate the accuracy of constituent and composite algorithms which address these questions. Fluorescence spectra acquired in vivo at all three excitation wavelengths from 381 cervical sites in 95 patients were analyzed to determine if the accuracy of each of the three constituent algorithms previously developed can be improved using tissue spectra at a combination of two or three excitation wavelengths rather than at a single excitation wavelength.

A second goal of this analysis is to integrate the three independently developed constituent algorithms which discriminate between pairs of tissue types into composite screening and diagnostic algorithms that can achieve discrimination between many of the clinically relevant tissue types. The effective accuracy of a composite screening algorithm for the identification of SILs (normal epithelium and inflammation versus SIL) and a composite diagnostic algorithm for the identification of high grade SILs (non-high grade versus high grade) was evaluated.

The third goal of the analysis is to determine if fluorescence intensities at a reduced number of excitation-emission wavelength pairs can be used to re-develop constituent and composite algorithms that can achieve classification with a minimum decrease in predictive ability. A significant reduction in the number of required fluorescence excitation-emission wavelength pairs could enhance the development of a cost-effective clinical fluorimeter. The accuracy of the constituent and composite algorithms based on the reduced emission variables was compared to the accuracy of those that utilize entire fluorescence emission spectra.

This ultimate result of this analysis is the clinically applicable diagnostic method for diagnosing cervical pre-cancer in accordance with the present invention. A patient may present in the clinic with an indication of disease or for a routine check up. The decision will be made to conduct an in vitro or in vivo diagnosis. If in vitro is selected, a tissue sample is taken from the cervix and prepared for examination. If in vivo is selected, the patient is examined directly. The general steps that follow are much the same. First, the cervical tissue is illuminated with a plurality of electromagnetic radiation wavelengths to produce a plurality of fluorescence intensity spectra. Second, a plurality of emission wavelengths from the fluorescence intensity spectra is detected. Third, the plurality of emission wavelengths from the patient is compared with known emission wavelengths for normal tissue. And fourth, a diagnostic determination on the cervical tissue is made.

II. Multivariate Statistical Method Development

The five primary steps involved in multivariate statistical methods of the present invention are (i) preprocessing of spectral data from each patient to account for inter-patient variation, (ii) partitioning of the preprocessed spectral data from all patients into calibration and prediction sets, (iii) dimension reduction of the preprocessed spectra in the calibration set using principal component analysis, (iv) selection of the diagnostically most useful principal components using a two-sided unpaired t-test and (v) development of an optimal classification scheme based on logistic discrimination using the diagnostically useful principal component scores of the calibration set as inputs. These five individual steps of the multivariate statistical method are discussed below in more detail.

(i) Preprocessing: The objective of preprocessing is to calibrate tissue spectra for inter-patient variation which might obscure differences in the spectra of different tissue types. Four methods of preprocessing were invoked on the spectral data: (a) normalization, (b) mean scaling, (c) a combination of normalization and mean scaling and (d) median scaling.

Spectra were normalized by dividing the fluorescence intensity at each emission wavelength by the maximum fluorescence intensity of that sample. Normalizing a fluorescence spectrum removes absolute intensity information; methods developed from normalized fluorescence spectra rely on differences in spectral line shape information for diagnosis. If the contribution of the absolute intensity information is not significant, two advantages are realized by utilizing normalized spectra. First, it is no longer necessary to calibrate for inter-patient variation of normal tissue fluorescence intensity as in the two-stage method. And second, identification of a colposcopically normal reference site in each patient prior to spectroscopic analysis is no longer needed.

Mean scaling was performed by calculating the mean spectrum for a patient (using all spectra obtained from cervical sites in that patient) and subtracting it from each spectrum in that patient. Mean-scaling can be performed on both unnormalized (original) and normalized spectra. Mean-scaling does not require colposcopy to identify a reference normal site in each patient prior to spectroscopic analysis. However, unlike normalization, mean-scaling displays the differences in the fluorescence spectrum from a particular site with respect to the average spectrum from that patient. Therefore this method can enhance differences in fluorescence spectra between tissue categories most effectively when spectra are acquired from approximately equal numbers of non diseased and diseased sites from each patient.

Median scaling is performed by calculating the median spectrum for a patient (using all spectra obtained from cervical sites in that patient) and subtracting it from each spectrum in that patient. Like mean scaling, median scaling can be performed on both unnormalized (original) and normalized spectra, and median scaling does not require colposcopy to identify a reference normal site in each patient prior to spectroscopic analysis. However, unlike mean scaling, median scaling does not require the acquisition of spectra from equal numbers of non diseased and diseased sites from each patient.

(ii) Calibration and Prediction Data Sets: The preprocessed spectral data were randomly assigned into either a calibration or prediction set. The multivariate statistical method was developed and optimized using the calibration set. It was then tested prospectively on the prediction data set.

(iii) Principal Component Analysis: Principal component analysis (PCA) is a linear model which transforms the original variables of a fluorescence emission spectrum into a smaller set of linear combinations of the original variables called principal components that account for most of the variance of the original data set. Principal component analysis is described in Dillon W. R., Goldstein M., *Multivariate Analysis: Methods and Applications,* John Wiley and Sons, 1984, pp. 23–52, the disclosure of which is expressly incorporated herein by reference. While PCA may not provide direct insight to the morphologic and biochemical basis of tissue spectra, it provides a novel approach of condensing all the spectral information into a few manageable components, with minimal information loss. Furthermore, each principal component can be easily related to the original emission spectrum, thus providing insight into diagnostically useful emission variables.

Prior to PCA, a data matrix is created where each row of the matrix contains the preprocessed fluorescence spectrum of a sample and each column contains the pre-processed fluorescence intensity at each emission wavelength. The data matrix D (RC), consisting of R rows (corresponding to r total samples from all patients in the training set) and C columns (corresponding to intensity at c emission wavelengths) can be written as:

$$D = \begin{pmatrix} D_{11} D_{12} \ldots D_{1c} \\ D_{21} D_{22} \ldots D_{2c} \\ \\ D_{r1} D_{r2} \ldots D_{rc} \end{pmatrix} \quad (1)$$

The first step in PCA is to calculate the covariance matrix, Z. First, each column of the preprocessed data matrix D is mean-scaled. The mean-scaled preprocessed data matrix, $D_m$ is then multiplied by its transpose and each element of the resulting square matrix is divided by (r−1), where r is the total number of samples. The equation for calculating Z is defined as:

$$Z = \frac{1}{r-1}(D_m / D_m) \quad (2)$$

The square covariance matrix, Z (c×c) is decomposed into its respective eigenvalues and eigenvectors. Because of experimental error, the total number of eigenvalues will always equal the total number of columns (c) in the data matrix D assuming that c<r. The goal is to select n<c eigenvalues that can describe most of the variance of the original data matrix to within experimental error. The variance, V accounted for by the first n eigenvalues can be calculated as follows:

$$V = 100 \left( \frac{\sum_{j=1}^{n} \lambda_j}{\sum_{j=1}^{c} \lambda_j} \right) \quad (3)$$

The criterion used in this analysis was to retain the first n eigenvalues and corresponding eigenvectors that account for 99% of the variance in the original data set.

Next, the principal component score matrix can be calculated according to the following equation:

$$R = DC \quad (4)$$

where, D (RC) is the preprocessed data matrix and C (c×n) is a matrix whose columns contain the n eigenvectors which correspond to the first n eigenvalues. Each row of the score matrix R (r×c) corresponds to the principal component scores of a sample and each column corresponds to a principal component. The principal components are mutually orthogonal to each other.

Finally, the component loading is calculated for each principal component. The component loading represents the correlation between the principal component and the variables of the original fluorescence emission spectrum. The component loading can be calculated as shown below:

$$CL_{ij} = \frac{C_{ij}}{\sqrt{S_{ii}}} \sqrt{\lambda_j} \quad (5)$$

where, $CL_{ij}$ represents the correlation between the ith variable (preprocessed intensity at ith emission wavelength) and the jth principal component. $C_{ij}$ is the ith component of the jth eigenvector, $\lambda_j$ is the jth eigenvalue and $S_{ii}$ is the variance of the ith variable.

Principal component analysis was performed on each type of preprocessed data matrix, described above. Eigenvalues accounting for 99% of the variance in the original preprocessed data set were retained The corresponding eigenvectors were then multiplied by the original data matrix to obtain the principal component score matrix R.

(iv) Student's T-Test: Average values of principal component scores were calculated for each histo-pathologic tissue category for each principal component obtained from the preprocessed data matrix. A two-sided unpaired student's t-test was employed to determine the diagnostic contribution of each principal component. Such a test is disclosed in Devore J. L., *Probability and Statistics for Engineering and the Sciences,* Brooks/Cole, 1992, and in Walpole R. E., Myers R. H., *Probability and Statistics for Engineers and Scientists,* Macmillan Publishing Co., 1978, Chapter 7, the disclosures of which are expressly incorporated herein by reference. The hypothesis that the means of the principal component scores of two tissue categories are different were tested for 1) normal squamous epithelia and SILs, 2) columnar normal epithelia and SILs and 3) inflammation and SILs. The t-test was extended a step further to determine if there are any statistically significant differences between the means of the principal component scores of high grade SILs and low grade SILs. Principal components for which the hypothesis stated above were true below the 0.05 level of significance were retained for further analysis.

(v) Logistic Discrimination: Logistic discriminant analysis is a statistical technique that can be used to develop diagnostic methods based on posterior probabilities, overcoming the drawback of the binary decision scheme employed in the two-stage method. This statistical classification method is based on Bayes theorem and can be used to calculate the posterior probability that an unknown sample belongs to each of the possible tissue categories identified. Logistic discrimination is discussed in Albert A., Harris E. K., *Multivariate Interpretation of Clinical Laboratory Data,* Marcel Dekker, 1987, the disclosure of which is expressly incorporated herein by reference. Classifying the unknown sample into the tissue category for which its posterior probability is highest results in a classification scheme that minimizes the rate of misclassification.

For two diagnostic categories, $G_1$ and $G_2$, the posterior probability of being a member of $G_1$, given measurement x, according to Bayes theorem is:

$$P(G_1 \mid X) = \frac{P(x \mid G_1)P(G_1)C(2 \mid 1)}{P(x \mid G_1)P(G_1)C(2 \mid 1) + P(x \mid G_2)P(G_2)C(1 \mid 2)} \quad (6)$$

where $P(x \bowtie G_i)$ is the conditional joint probability that a tissue sample of type i will have principal component score x, and $P(G_i)$ is the prior probability of finding tissue type i in the sample population. $C(j \bowtie i)$ is the cost of misclassifying a sample into group j when the actual membership is group i.

The prior probability $P(G_i)$ is an estimate of the likelihood that a sample of type i belongs to a particular group when no information about it is available. If the sample is considered representative of the population, the observed proportions of cases in each group can serve as estimates of the prior probabilities. In a clinical setting, either historical incidence figures appropriate for the patient population can be used to generate prior probabilities, or the practitioner's colposcopic assessment of the likelihood of precancer can be used to estimate prior probabilities.

The conditional probabilities can be developed from the probability distributions of the n principal component scores for each tissue type, i. The probability distributions can be modeled using the gamma function, which is characterized by two parameters, alpha and beta, which are related to the mean and standard deviation of the data set. The Gamma function is typically used to model skewed distributions and is defined below:

$$f(x; \alpha, \beta) = \frac{1}{\beta^\alpha \Gamma(\alpha)} x^{\alpha-1} e^{-\frac{x}{\beta}} \quad (7)$$

The gamma function can be used to calculate the conditional probability that a sample from tissue type i, will exhibit the principal component score, x. If more than one principal component is needed to describe a sample population, then the conditional joint probability is simply the product of the conditional probabilities of each principal component (assuming that each principal component is an independent variable) for that sample population.

III. Instrumentation

Fluorescence occurs when a fraction of the light absorbed by the tissue is reradiated at emission wavelengths that are longer than the excitation light. Thus, the apparatus of the present invention includes a controllable illumination device for emitting a plurality of electromagnetic radiation wavelengths selected to cause a tissue to produce a fluorescence intensity spectrum. Typically, the light source is a laser. Also included are an optical system for applying the plurality of radiation wavelengths to a tissue sample, a fluorescence intensity spectrum detecting device for detecting an intensity of fluorescence spectra emitted by the sample as a result of illumination by the plurality of electromagnetic radiation wavelengths. Optionally, the system may include a data processor, connected to the detecting device, for analyzing detected fluorescence spectra to calculate a probability that the sample is abnormal.

A schematic of the portable fluorimeter which was used to acquire cervical tissue fluorescence spectra at three excitation wavelengths is shown in FIG. 1 (1). The fiber-optic probe includes a central fiber surrounded by a circular array of six fibers; all seven fibers have the same characteristics (0.22 NA, 200 μm core diameter). Three fibers along the diameter of the distal end of the probe (FIG. 1 (3)) are used for excitation light delivery (overlap of the illumination area viewed by the three excitation fibers is greater than 85%). The purpose of the remaining four fibers is to collect the emitted fluorescence from the area (1 mm diameter) directly illuminated by the probe. A quartz shield at the tip of the distal end of the probe which is in direct tissue contact (FIG. 1 (5)) provides a fixed distance between the optical fibers and the tissue surface so fluorescence intensity can be measured in calibrated units.

Two nitrogen pumped-dye lasers are used to provide illumination at three different excitation wavelengths: one laser serves to deliver excitation light at 337 nm (fundamental) and has a dye module which is used to generate light at 380 nm using the fluorescent dye, BBQ (1E-03 M in 7 parts toluene and 3 parts ethanol). The dye module of the second laser is used to provide illumination at 460 nm, using the fluorescent dye, Coumarin 460 (1E-02 M in ethanol). Laser illumination at each excitation wavelength, 337, 380 and 460 nm is coupled into each of the excitation fibers. In this study, the average transmitted pulse energies at 337, 380 and 460 nm excitation were 12, 9 and 14 μJ, respectively. The laser characteristics were a 5 ns pulse duration and a repetition rate of 30 Hz.

The proximal ends of the four emission collection fibers are arranged in a circular array and imaged at the entrance slit of a polychromator coupled to a 1,024 intensified diode array controlled by a multi-channel analyzer. 360, 400 and 470 nm long pass filters are used to block scattered excitation light at 337, 380 and 460 nm excitation, respectively from the detector. A 205 ns collection gate, synchronized to the leading edge of the laser pulse using a pulser (Princeton Instruments, PG200), eliminates the effects of the colposcope's white light illumination during fluorescence measurements. Data acquisition is computer controlled.

IV. Combining Fluorescence and Raman Spectroscopies

The present invention also contemplates a method that combines fluorescence spectroscopy, as described above, with NIR Raman spectra, in vitro or in vivo. This is accomplished through a light source, sequentially or simultaneously, in conjunction with an optical coupling system for the application and analysis of both kinds of data. For example, a probe is selectively coupled to ultraviolet or visible sources of electromagnetic radiation to excite fluorescence, and then selectively coupled to NIR sources to excite fluorescence-free Raman spectra. The fluorescence spectra may be used to improve the analytical rejection of fluorescence from the Raman spectrum.

In one embodiment, the apparatus comprises a diachronic mirror or swing-way mirror so that each electromagnetic radiation source is selectively coupled to the optical excitation fiber(s). Similarly, light collected by the collection fiber may be selectively coupled to the appropriate detectors. Alternatively, a probe may house discrete sets of fluorescence and Raman excitation and detection fibers, thereby obviating the need for mirrors.

In analyzing the spectra, fluorescence may be used advantageously to identify normal tissues and low and high grade lesions. NIR Raman spectra can be used advantageously to identify inflammation and metaplasia. Alternatively, information gathered about the tissue type, in accordance with the above-described fluorescence methods, can be used to improve the Raman diagnostic capability. This is accomplished by using fluorescence spectra to calculate the posterior probability that tissue is normal, low grade or high grade SIL. Then, this classification is used as the prior probability in logistic discrimination, based on the detected Raman spectra. In yet another embodiment, information gathered with NIR Raman spectroscopy is used to calculate the posterior probability that the tissue is inflamed or metaplastic. Then, this information is used as the prior probability in logistic discrimination, based on the detected fluorescence spectrum. By the same token, Raman can improve the diagnostic performance of fluorescence by reducing misclassification of inflammation and metaplasia as precancer.

In one embodiment, the Raman method comprises illuminating a sample with an electromagnetic radiation wavelength in the near infrared to produce a Raman spectrum shifted from the illumination wavelength; detecting a plurality of emission frequencies of the spectrum; and establishing from the emission frequencies a probability that the sample is abnormal. The excitation wavelength typically is between 700 and 850 nm, with a wavelength of about 789 nm being a specific embodiment. Emission frequencies are shifted about 626, 818, 978, 1070, 1175, 1246, 1330, 1454 and 1656 $cm^{-1}$ from 789 nm in a more specific embodiment.

Another approach that may be taken in examining Raman spectra is to look at the Raman signatures of specific compounds. In this embodiment, compounds of interest include collagen, phopholipids and glucose-1-phosphate. The Raman spectrum measured for collagen contains peaks at 770, 826, 1066, 1181, 1248, 1452 and 1660 $cm^{-1}$. Glucose 1-phosphate is an intermediate product in the glycogen-glucose conversion cycle and found in abundance in cervical epithelial cells. The spectrum of glucose 1-phosphate includes peaks at 850, 970, 1053, 1091, 1146 and 1350 $cm^{-1}$. The peaks for one major phospholipid, phosphatidylcholine, are at 740, 980, 1091, 1320 and 1454 $cm^{-1}$.

V. Examples

The following examples are included to demonstrate specific embodiments of the present invention. It should be appreciated by those of skill in the art that the techniques disclosed in the examples which follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1: METHODS

Clinical measurements.

A randomly selected group of non-pregnant patients referred to the colposcopy clinic of the University of Texas MD Anderson Cancer Center on the basis of abnormal cervical cytology was asked to participate in the in vivo fluorescence spectroscopy study. Informed consent was obtained from each patient who participated and the study was reviewed and approved by the Institutional Review Boards of the University of Texas, Austin and the University of Texas, MD Anderson Cancer Center. Each patient underwent a complete history and a physical examination including a pelvic exam, a Pap smear and colposcopy of the cervix, vagina and vulva.

After colposcopic examination of the cervix, but before tissue biopsy, fluorescence spectra were acquired on average from two colposcopically abnormal sites, two colposcopically normal squamous sites and 1 normal columnar site (if colposcopically visible) from each patient. Tissue biopsies were obtained only from abnormal sites identified by colposcopy and subsequently analyzed by the probe to comply with routine patient care procedure. All tissue biopsies were fixed in formalin and submitted for histologic examination. Hemotoxylin and eosin stained sections of each biopsy specimen were evaluated by a panel of four board certified pathologists and a consensus diagnosis was established using the Bethesda classification system [1]. This classification system which has previously been used to grade cytologic specimens has now been extended to classification of histology samples. Samples were classified as normal squamous, normal columnar, inflammation, low grade SIL or high grade SIL. Samples with multiple diagnoses were classified into the most severe histo-pathologic category.

Prior to each patient study, the probe was disinfected and a background spectrum was acquired at all three excitation wavelengths consecutively with the probe dipped in a non-fluorescent bottle containing distilled water. The background spectrum was subtracted from all subsequently acquired spectra at corresponding excitation wavelengths for that patient. Next, with the probe placed on the face of a quartz cuvette containing a solution of Rhodamine 610 dissolved in ethylene glycol (2 mg/L), 50 fluorescence spectra were measured at each excitation wavelength. After calibration, fluorescence spectra were acquired from the cervix: 10 spectra for 10 consecutive pulses were acquired at 337 nm excitation; next, 50 spectra for 50 consecutive laser pulses were measured at 380 mn excitation and then at 460 nm excitation. The data acquisition time was 0.33 s at 337 nm excitation and 1.67 s at each 380 and 460 nm excitation per cervical site. Spectra were collected in the visible region of the electromagnetic spectrum with a resolution of 10 nm (full width at half maximum) and a signal to noise ratio of 30:1 at the fluorescence maximum at each excitation wavelength.

All spectra were corrected for the non-uniform spectral response of the detection system using correction factors obtained by recording the spectrum of an N.I.S.T traceable calibrated tungsten ribbon filament lamp. Spectra from each cervical site at each excitation wavelength were averaged and normalized to the peak fluorescence intensity of the Rhodamine 610 calibration standard at the corresponding excitation wavelength for that patient; absolute fluorescence intensities are reported in these calibrated units. In this clinical study, fluorescence spectra were acquired at all three excitation wavelengths from each cervical site from a total of 381 sites in 95 patients during colposcopy.

EXAMPLE: 2: STATISTICAL METHODS

Figure 2:
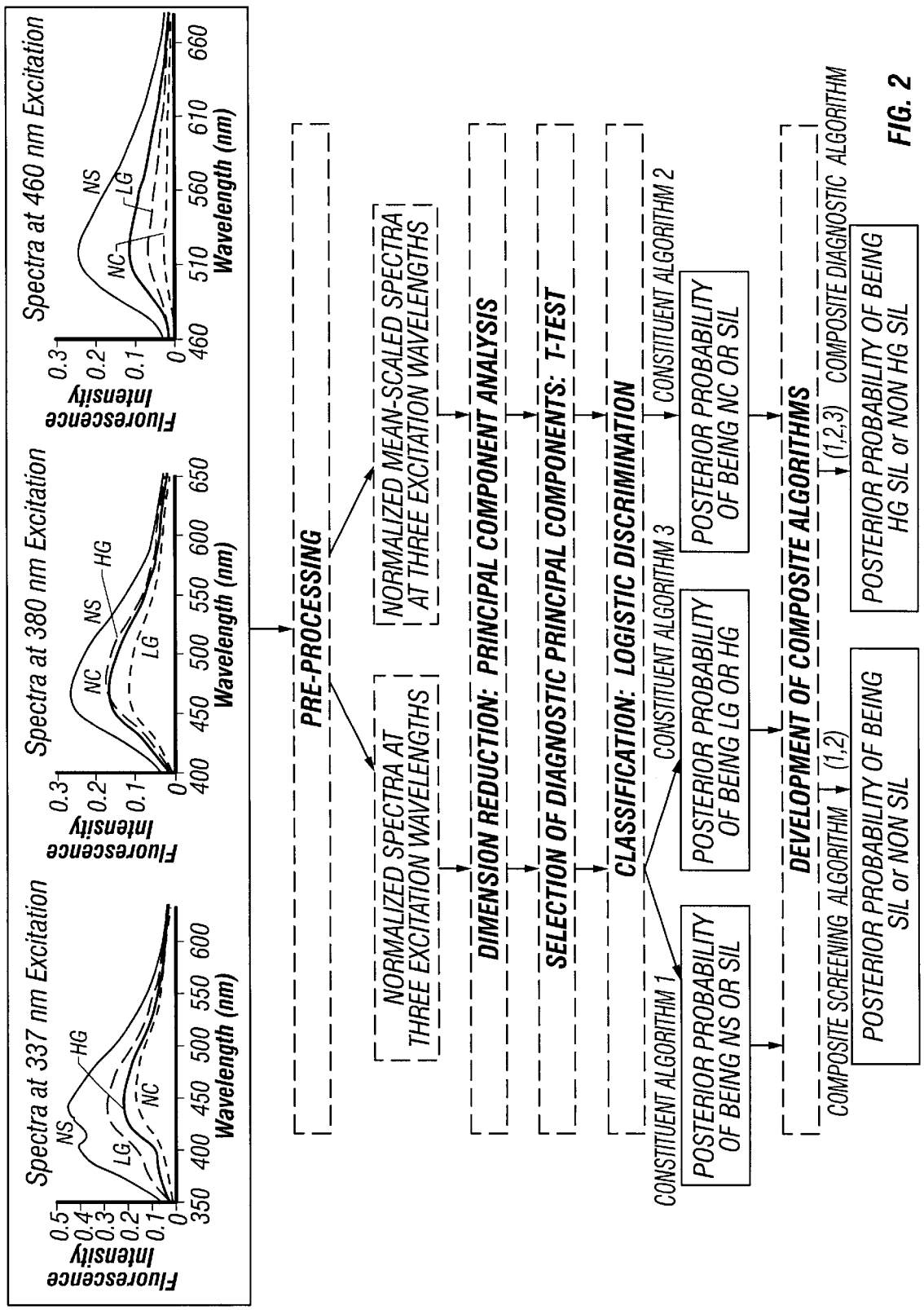
FIG. 2. A flow chart of a formal analytical process used to develop the screening and diagnostic algorithms. The text in the dashed-line boxes represent mathematical steps implemented on the spectral data and the text in the solid line boxes represent outputs after each mathematical step (NS—normal squamous, NC—normal columnar, LG—LG SIL and HG—HG SIL).

Development of screening and diagnostic algorithms:

FIG. 2 illustrates a schematic of the formal analytical process used to develop screening and diagnostic algorithms for the differential detection of SILs, in vivo. In FIG. 2, the text in the dashed-line boxes represents the mathematical steps implemented on the spectral data, and the text in the solid-line boxes represent the output after each mathematical process. There are four primary steps involved in the multivariate statistical analysis of tissue spectral data (FIG. 2). The first step is to pre-process spectral data to reduce inter-patient and intra-patient variation within a tissue type; the pre-processed spectra are then dimensionally reduced into an informative set of principal components which describe most of the variance of the original spectral data set using Principal Component Analysis (PCA). Next, the principal components which contain diagnostically relevant information are selected using an unpaired, one-sided student s t-test, and finally a classification algorithm based on logistic discrimination is developed using these diagnostically relevant principal components.

In summary, three constituent algorithms were developed using multivariate statistical analysis (FIG. 2): a constituent algorithm (1) discriminates between SILs and normal squamous tissues, a constituent algorithm (2) discriminates between SILs and normal columnar tissues and finally, a constituent algorithm (3) differentiates high grade SILs from low grade SILs. The three constituent algorithms were then combined to develop two composite algorithms (FIG. 2): constituent algorithms (1) and (2) were combined to develop a composite screening algorithm which discriminates between SILs and non SILs. All three constituent algorithms were then combined to develop a composite diagnostic algorithm which differentiates high grade SILs from non-high grade SILs.

Multivariate statistical analysis of cervical tissue spectra.

As a first step, three methods of pre-processing were applied to the spectral data at each excitation wavelength: 1) normalization 2) mean-scaling and 3) a combination of normalization and mean-scaling. Similarly pre-processed spectra at each excitation wavelength were combined to create spectral inputs at the following combinations of excitation wavelengths: (337, 460) nm, (337, 380) nm, (380, 460) nm and (337, 380, 460) nm. Pre-processing of spectral data resulted in four types of spectral inputs (original and three types of pre-processed spectral inputs) at four single excitation wavelengths and at four possible combinations of multiple excitation wavelengths. Hence, there were a total of 12 spectral inputs at single excitation wavelengths and 16 spectral inputs at multiple excitation wavelengths which were evaluated using the multivariate statistical algorithm.

Prior to PCA, the input data matrix, D (RC) was created so each row of the matrix corresponded to the pre-processed fluorescence spectrum of a sample and each column corresponded to the pre-processed fluorescence intensity at each emission wavelength. Spectral inputs at multiple excitation wavelengths were created by arranging spectra at each excitation wavelength in series in the original spectral data matrix. PCA [28] was used to dimensionally reduce the pre-processed spectral data matrix into a smaller orthogonal set of linear combinations of the emission variables that account for most of the variance of the spectral data set.

Average values of principal component scores were calculated for each principal component of each tissue type. An unpaired, one-sided student's t-test [29] was employed to determine the diagnostic content of each principal component. The hypothesis that the means of the principal component scores of two tissue types are different was tested for (1) normal squamous epithelia and SILs, (2) normal columnar epithelia and SILs and (3) inflammation and SILs. The t-test was extended a step further to determine if there were any statistically significant differences between the means of the principal component scores of high grade SILs and low grade SILs. Principal components for which the hypothesis stated above was statistically significant ($P<0.05$) were retained for further analysis.

Next, a statistical classification algorithm was developed using the diagnostically useful principal components to calculate the posterior probability that an unknown sample belongs to each tissue type under consideration. The posterior probability of an unknown sample belonging to each tissue type was calculated using logistic discrimination [30]. The posterior probability is related to the prior and conditional joint probabilities and to the costs of misclassification of the tissue types under consideration. The prior probability of each tissue type was determined by calculating the observed proportion of cases in each group. The cost of misclassification of a particular tissue type was varied from 0 to 1 in 0.1 increments, and the optimal cost was identified when the total number of misclassified samples based on the classification algorithm was a minimum. If there was more than one cost at which the total number of misclassified samples was a minimum, the cost that maximized sensitivity was selected. The conditional joint probabilities were developed by modeling the probability distribution of each principal component of each tissue type using the normal probability density function [31], which is characterized by $\mu$ (mean) and $\sigma$ (standard deviation). The best fit of the normal probability density function to the probability distribution of each principal component (score) of each tissue type was obtained in the least squares sense, using $\mu$ and $\sigma$ as free parameters of the fit. The normal probability density function was then used to calculate the conditional joint probability that an unknown sample, given that it is from tissue type i, will exhibit a set of principal component scores, X.

The multivariate statistical algorithm was developed and optimized using a calibration set and then tested in an unbiased manner on a prediction set of approximately equal prior probability (Table 1). Data in the prediction set is pre-processed and organized into two prediction datasets in the following way:

Spectra obtained from each patient at each excitation wavelength are separately (1) normalized and (2) normalized, followed by mean-scaling. Spectra at each excitation wavelength, processed in a similar manner are concatenated into a vector. Two prediction data matrices are developed. In each matrix, each row is a vector containing similarly pre-processed fluorescence emission spectra at 337, 380 and 460 nm excitation concatenated and each column corresponds to pre-processed fluorescence intensity at a particular excitation emission wavelength pair.

These processed data matrices are then used to test the composite screening algorithm performance. The steps of this test are:

The normalized prediction data matrix (Dn') is multiplied by the reduced eigenvector matrix from normalized spectral data of the calibration set (Cn'). Cn' contains only those eigenvectors which displayed statistically significant differences for samples to be classified by constituent algorithm 1.

The posterior probabilities that a sample is SIL or normal squamous epithelium are calculated using Bayes theorem. In this calculation, the mean values and standard deviations of the PC scores for normal squamous epithelium and SILs and prior probabilities and optimal costs of misclassification of the calibration set are used.

The normalized, mean-scaled prediction data matrix (Dnm') is multiplied by the reduced eigenvector matrix from normalized, mean-scaled spectral data of the calibration set (Cmn'). Cmn' contains only those eigenvectors which displayed statistically significant differences for samples to be classified by constituent algorithm 2.

The posterior probabilities that a sample is SIL or normal columnar epithelium are calculated using Bayes theorem. In this calculation, the mean values and standard deviations of the PC scores for normal columnar epithelium and SILs and prior probabilities and optimal costs of misclassification of the calibration set are used.

Using constituent algorithm 1, samples with a posterior probability of being normal squamous epithelium greater than a threshold value are classified as non-SIL. Remaining samples are classified based on the output of constituent algorithm 2. Using constituent algorithm 2, sample with a posterior probability of being normal columnar epithelium greater than a threshold are classified as non-SIL. The remaining samples are classified as SIL.

The processed data matrices are then used to test the composite diagnostic algorithm performance. The steps of this test are:

The normalized prediction data matrix (Dn') is multiplied by the reduced eigenvector matrix from normalized spectral data of the calibration set (Cn'). Cn' contains only those eigenvectors which displayed statistically significant differences for samples to be classified by constituent algorithm 1.

The posterior probabilities that a sample is SIL or normal squamous epithelium are calculated using Bayes theorem. In this calculation, the mean values and standard deviations of the PC scores for normal squamous epithelium and SILs and prior probabilities and optimal costs of misclassification of the calibration set are used.

The normalized, mean-scaled prediction data matrix (Dnm') is multiplied by the reduced eigenvector matrix from normalized, mean-scaled spectral data of the calibration set (Cmu'). Cnm' contains only those eigenvectors which displayed statistically significant differences for samples to be classified by constituent algorithm 2.

The posterior probabilities that a sample is SIL or normal columnar epithelium are calculated using Bayes theorem. In this calculation, the mean values and standard deviations of the PC scores for normal columnar epithelium and SILs and prior probabilities and optimal costs of misclassification of the calibration set are used.

The normalized prediction data matrix (Dn') is multiplied by the reduced eigenvector matrix from normalized spectral data of the calibration set (Cn'). Cn' contains only those eigenvectors which displayed statistically significant differences for samples to be classified by constituent algorithm 3.

The posterior probabilities that a sample is HGSIL or LGSIL are calculated using Bayes theorem. In this calculation, the mean values and standard deviations of the PC scores for HGSILs and LGSILs and prior probabilities and optimal costs of misclassification of the calibration set are used.

Using constituent algorithm 1, samples with a posterior probability of being normal squamous epithelium greater than a threshold are classified as non-SIL. Remaining samples are classified based on the output of constituent algorithm 2. Using constituent algorithm 2, sample with a posterior probability of being normal columnar epithelium greater than a threshold are classified as non-SIL. Remaining samples are classified based on the output of constituent algorithm 3. Using constituent algorithm 3, samples with a posterior probability of being LGSIL greater than a threshold are classified as LGSIL. The remaining samples are classified as HGSIL.

The calibration and prediction sets were developed by randomly assigning the spectral data into the two sets with the condition that both contain roughly equal number of samples from each histo-pathologic category. The random assignment ensured that not all spectra from a single patient were contained in the same data set.

TABLE 1

Histo-pathologic classification of samples from the calibration and prediction sets. Note, biopsies for histological evaluation were not obtained from colposcopically normal squamous and columnar tissue sites to comply with routine patient care procedure.

| Histo-pathology | Calibration Set | Prediction Set |
|---|---|---|
| Normal Squamous | 94 | 94 |
| Normal Columnar | 13 | 14 |
| Inflammation | 15 | 14 |

TABLE 1-continued

Histo-pathologic classification of samples from the calibration and prediction sets. Note, biopsies for histological evaluation were not obtained from colposcopically normal squamous and columnar tissue sites to comply with routine patient care procedure.

| Histo-pathology | Calibration Set | Prediction Set |
|---|---|---|
| Low Grade SIL | 23 | 24 |
| High Grade SIL | 35 | 35 |

Development of constituent algorithms:

The multivariate statistical algorithm was developed and optimized using all 28 types of pre-processed spectral inputs from the calibration set. The algorithm was used to identify spectral inputs which provide the greatest discrimination between the following pairs of tissue types: (1) SILs and normal squamous epithelia, (2) SILs and normal columnar epithelia, (3) SILs and inflammation, and (4) high grade SILs and low grade SILs. The optimal spectral input for differentiating between two particular tissue types was identified when the total number of samples misclassified from the calibration set using the multivariate statistical algorithm was a minimum. The algorithm based on the spectral input that minimized misclassification between the two tissue types under consideration was implemented on the prediction data set.

Three multivariate statistical constituent algorithms were developed using tissue spectra at three excitation wavelengths. Constituent algorithm (1) was developed to differentiate between SILs and normal squamous epithelia; constituent algorithm (2) was developed to differentiate between SILs and normal columnar epithelia and constituent algorithm (3) could be used to discriminate between low grade SILs and high grade SILs.

Development of composite algorithms:

Each of the independently developed constituent algorithms was intended to discriminate only between pairs of tissue types. A combination of these constituent algorithms was required to provide discrimination between several of the clinically relevant tissue types. Therefore, two composite algorithms were developed: a composite screening algorithm was developed to differentiate between SILs and non SILs (normal squamous and columnar epithelia and inflammation) using constituent algorithms (1) and (2) and a composite diagnostic algorithm was developed to differentiate high grade SILs from non-high grade SILs (low grade SILs, normal epithelia and inflammation) using all three constituent algorithms.

The composite screening algorithm was developed in the following manner. First, constituent algorithms (1) and (2) were developed independently using the calibration data set. The classification outputs from both constituent algorithms were used to determine if a sample being evaluated is SIL or non-SIL: first, using constituent algorithm (1), samples were classified as non SIL if they had a probability that is less than 0.5; otherwise, they were classified as SIL. Next only samples that were classified as SIL based on the algorithm (1) were tested using algorithm (2). Again, samples were classified as non SIL if their posterior probability was less than 0.5; otherwise they were classified as SIL. The spectral data from the prediction set was evaluated using the composite screening algorithm in an identical manner.

The composite diagnostic algorithm was implemented in the following manner. The three constituent algorithms were developed independently using the calibration set. Algorithms (1) and (2) were implemented on each sample from the calibration data set, as described previously. Only samples that were classified as SIL based on algorithms (1) and (2) were tested using algorithm (3). If samples evaluated using algorithm (3) had a posterior probability greater than 0.5, they were classified as high grade SIL; otherwise they were classified as non-high grade SIL. The spectral data from the prediction set was evaluated using the composite diagnostic algorithm in an identical manner.

EXAMPLE 3: RESULTS

Constituent algorithms (1), (2) and (3):

Table 2 summarizes the components of the optimal set of three constituent algorithms. Constituent algorithm (1) can be used to differentiate between SILs and normal squamous epithelia; algorithm (2) differentiates between SILs and normal columnar epithelia; and algorithm (3) discriminates between low grade SILs and high grade SILs.

Figure 3A:
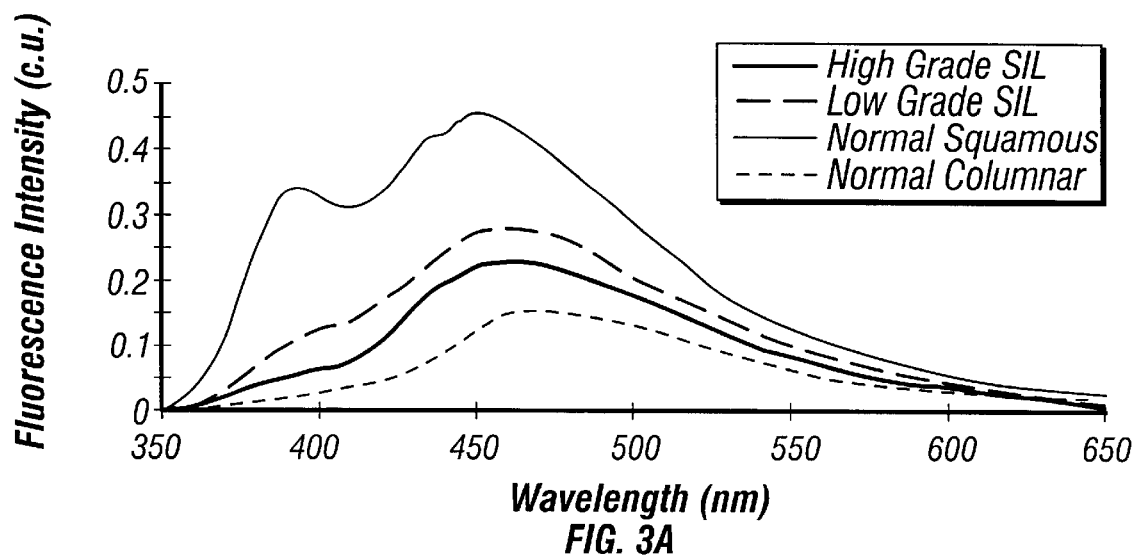
FIGS. 3A, 3B and 3C.
Figure 3B:
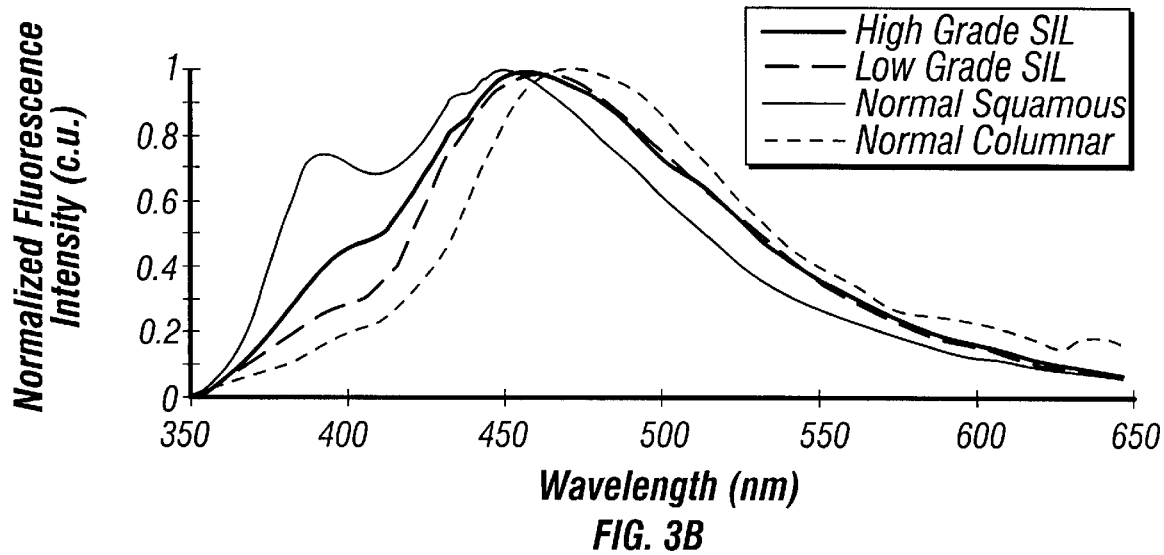
Figure 3C:
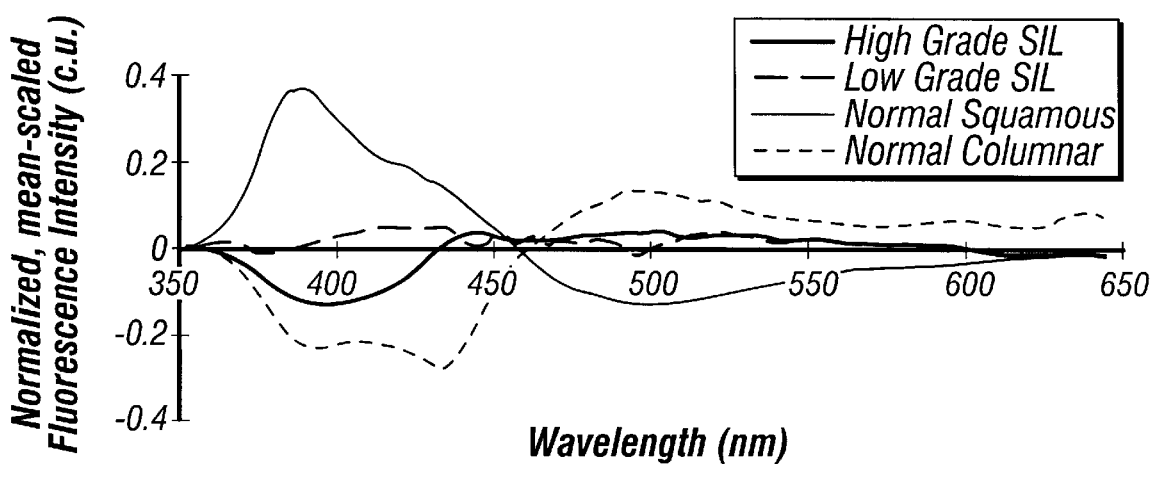

The corresponding normalized, mean-scaled spectra of this patient, shown in FIG. 3C displays differences in the normalized fluorescence spectrum (FIG. 3B) from a particular site with respect to the average normalized spectrum from this patient. Evaluation of FIG. 3C indicates that between 360 and 450 nm, the normalized, mean-scaled fluorescence intensity of the normal squamous tissue is greater than the mean (Y=0), and that of the normal columnar tissue is less than the mean. Above 460 nm, the opposite phenomenon is observed; the fluorescence intensity of the normal squamous tissue is less than the mean, while that of the normal columnar tissue is greater than the mean. The fluorescence intensity of SILs lies close to the mean and is bounded by the intensities of the two normal tissue types. In addition, between 360 and 420 nm, the normalized, mean-scaled fluorescence intensity of the low grade SIL is slightly greater than the mean, while that of the high grade SIL is less than the mean.

TABLE 2

| Constituent Algorithms | Excitation Wavelengths | Pre-processing Method | PC[1] | V(%)[2] | $(\mu, \sigma)$[3] | PP[4] |
|---|---|---|---|---|---|---|
| (1) | 337, 380, 460 | normalization | PC1 | 51 | NS: (2.993, 1.589); SIL: (2.514, 0.671) | NS: 62% |
| SIL vs. | | | PC3 | 11 | NS: (2.631, 0.292); SIL: (2.535, 0.427) | SIL: 38% |
| Normal Squamous (NS) | | | PC7 | 3 | NS: (2.850, 0.145); SIL: (2.775, 0.209) | |
| (2) | 337, 380, 460 | normalization | PC1 | 59 | NC: (2.479, 0.444); SIL: (2.737, 0.482) | NC: 28% |
| SIL vs. | | mean-scaling | PC2 | 12 | NC: (2.894, 0.330); SIL: (2.990, 0.367) | SIL: 72% |
| Normal Columnar (NC) | | | PC4 | 6 | NC: (3.006, 0.186); SIL: (3.051, 0.167) | |
| | | | PC5 | 3 | NC: (3.004, 0.101); SIL: (2.994, 0.199) | |
| (3) | 337, 380, 460 | normalization | PC1 | 51 | LG: (2.755, 0.663); HG (2.353, 0.759) | LG: 40% |
| HG SIL (HG) vs. | | | PC3 | 11 | LG: (2.549, 0.394); HG (2.453, 0.497) | HG: 60% |
| LG SIL (LG) | | | PC6 | 3 | LG: (2.042, 0.180); HG (2.100, 0.180) | |
| | | | PC8 | 2 | LG: (2.486, 0.223); HG (2.550, 0.130) | |

Components of an optimal set of three constituent algorithms. Algorithm (1) discriminates between SILs and normal squamous tissues, algorithm (2) discriminates between SILs and normal columnar tissues and algorithm (3) differentiates high grade (HG) SILs from low grade (LG) SILs. Principal Component Analysis: 1 - Principal Component; 2 - Variance accounted for by principal component. Logistic Discrimination: 3 - $\mu$ (mean) and $\sigma$ (standard deviation) of principal component scores of tissue types under consideration; 4 - prior probabilities of tissue types under consideration.

Pre-processing:

FIG. 3A illustrates average fluorescence spectra per site acquired from cervical sites at 337 nm excitation from a typical patient. All fluorescence intensities are reported in the same set of calibrated units. Corresponding normalized and normalized, mean-scaled spectra are illustrated in FIGS. 3B and 3C, respectively. Evaluation of the original spectra at 337 nm excitation (FIG. 3A) indicates that the fluorescence intensity of SILs is less than that of the corresponding normal squamous tissue and greater than that of the corresponding normal columnar tissue over the entire emission spectrum. Examination of normalized spectra from this patient (FIG. 3B) indicates that following normalization, the fluorescence intensity of the normal squamous tissue is greater than that of corresponding SILs over the wavelength range 360 to 450 nm only; between 460 and 600 nm, the fluorescence intensity of SILs is greater than that of the corresponding normal squamous tissue which in part reflects the longer peak emission wavelength of SILs. A comparison of the spectral line shape of SILs to that of the normal columnar tissue illustrates the opposite phenomenon. The normalized fluorescence intensity of SILs is greater than that of the corresponding normal columnar tissue over the wavelength range 360 to 450 nm; however, between 460 and 600 nm, the fluorescence intensity of the normal columnar tissue is greater than that of the SILs. This spectral difference reflects the longer peak emission wavelength of the normal columnar tissue relative to that of SILs. Further evaluation of normalized spectra in FIG. 3B indicates that there are spectral line shape differences between low grade SILs and high grade SILs over the wavelength range 360 to 420 nm.

Figure 4A:
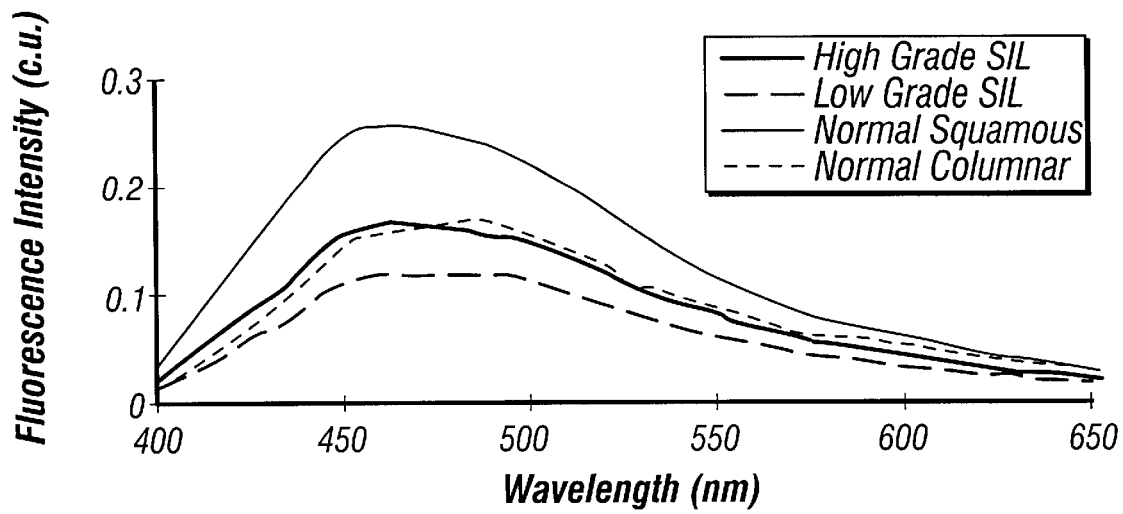
FIGS. 4A, 4B and 4C.
Figure 4B:
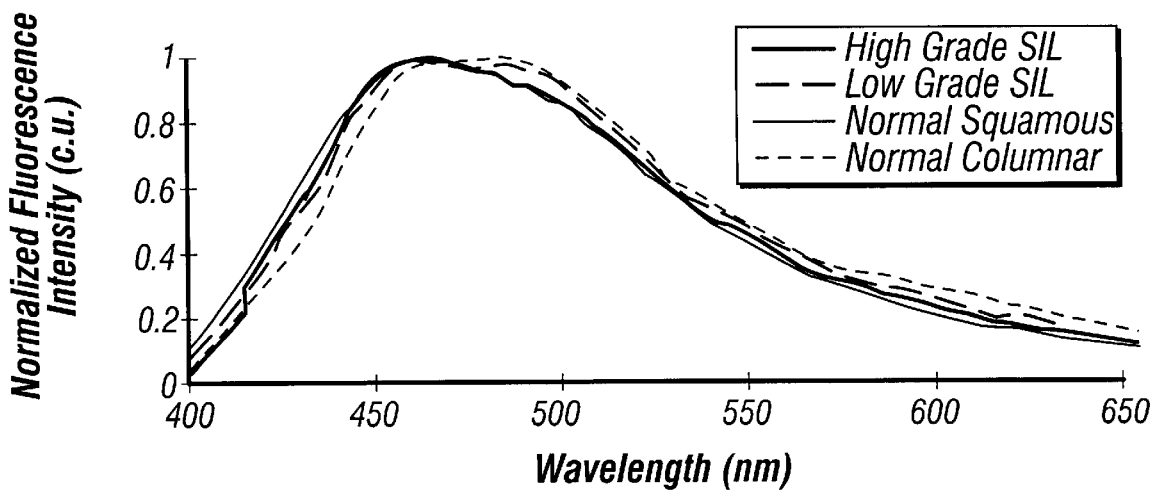
Figure 4C:
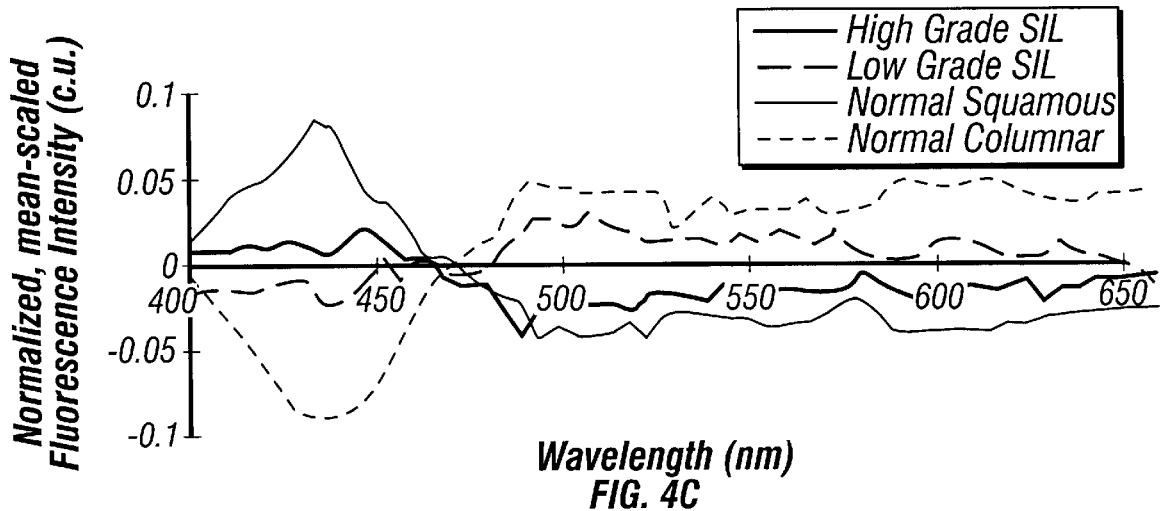

FIG. 4A illustrates average fluorescence spectra per site acquired from cervical sites at 380 nm excitation, from the same patient. FIGS. 4B and 4C show the corresponding normalized, and normalized, mean-scaled spectra, respectively. In FIG. 4A, the fluorescence intensity of SILs is less than that of the corresponding normal squamous tissue, with the low grade SIL exhibiting the weakest fluorescence intensity over the entire emission spectrum. Note that the fluorescence intensity of the normal columnar sample is indistinguishable from that of the low grade SIL. Normalized spectra at 380 nm excitation, (FIG. 4B), indicate that over the wavelength range 400 to 450 nm, the fluorescence intensity of the normal squamous tissue is slightly greater than that of SILs and that of the normal columnar tissue is less than that of SILs. The opposite phenomenon is observed above 580 mn. A careful examination of the spectra of the low grade SIL and high grade SIL indicates that between 460 and 580 nm, the normalized fluorescence intensity of the low grade SIL is higher than that of the high grade SIL. The normalized, mean-scaled spectra (FIG. 4C) enhances the previously observed normalized spectral line shape differences by displaying them relative to the average normalized spectrum of this patient. FIG. 4C indicates that between 400 to 450 nm, the fluorescence intensity of the normal squamous tissue is greater than the mean and that of the normal columnar tissue is less than the mean. The opposite phenomenon is observed above 460 nm. The fluorescence intensity of the SILs is bounded by the intensities of the two normal tissue types over the entire emission spectrum. The low grade SIL and high grade SIL also show spectral line shape differences; above 460 nm, the normalized, mean-scaled fluorescence intensity of the low grade SIL lies above the mean and that of the high grade SIL lies below the mean.

Figure 5A:
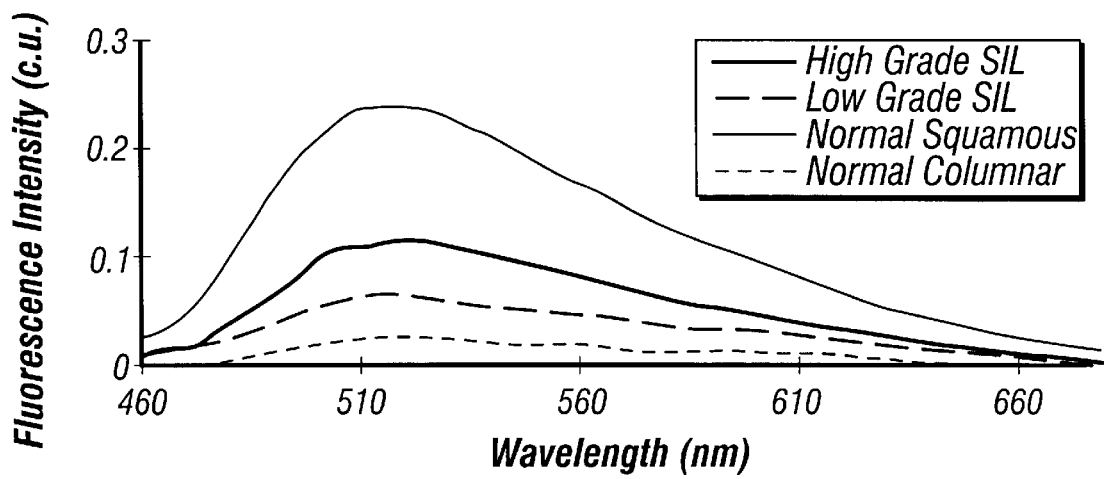
FIGS. 5A, 5B and 5C.
Figure 5B:
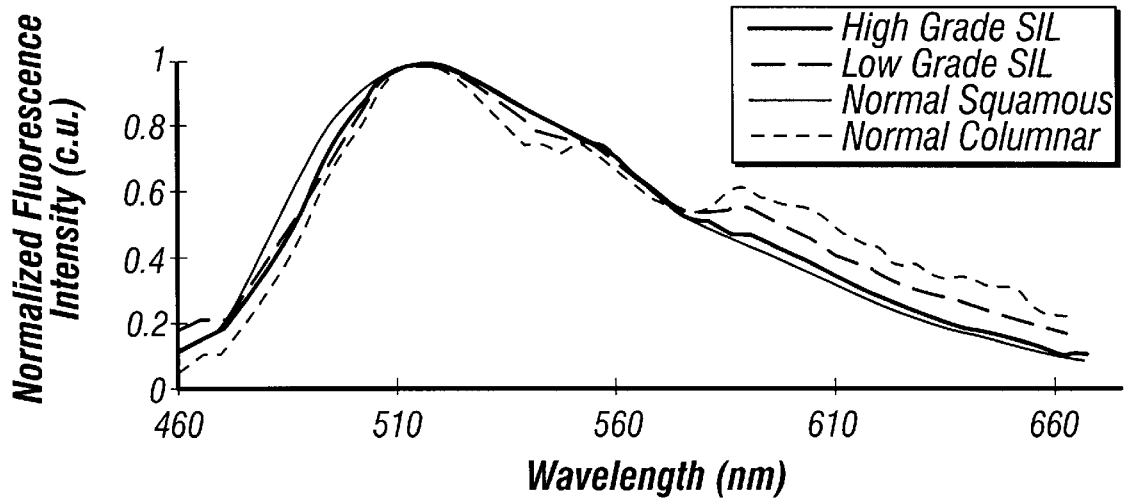
Figure 5C:
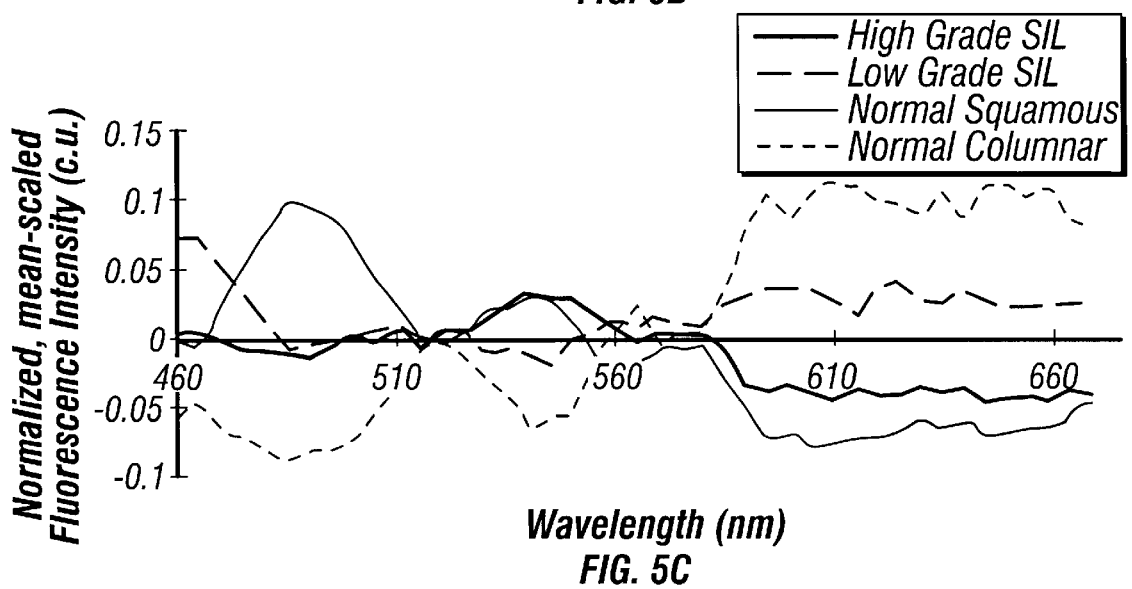

FIGS. 5A, 5B and 5C illustrate original, normalized and normalized, mean-scaled spectra, respectively at 460 nm excitation from the same patient. Evaluation of FIG. 5A indicates that the fluorescence intensity of SILs is less than that of the corresponding normal squamous tissue and greater than that of the corresponding normal columnar sample over the entire emission spectrum. Evaluation of normalized spectra at this excitation wavelength (FIG. 5B) demonstrates that below 510 nm, the fluorescence intensity of SILs is less than that of the normal squamous tissue and greater than that of the corresponding normal columnar tissue. Above, 580 nm, the normalized fluorescence intensity of SILs is less than that of the normal columnar tissue and greater then that of normal squamous tissue. Note that there are spectral line shape differences between the low grade SIL and high grade SIL between 580 and 660 nm; the normalized fluorescence intensity of the low grade SIL is greater than that of the high grade SIL. The normalized, mean-scaled spectra shown in FIG. 5C reflects the differences observed in the normalized spectra relative to the average normalized spectrum of this patient. Below 510 nm, the fluorescence intensity of the normal squamous tissue is greater than the mean, while that of the normal columnar tissue is less than the mean. Above 580 nm, the opposite phenomenon is observed. The fluorescence intensity of the SILs lies between those of the two normal tissue types. Above 580 nm, the fluorescence intensity of the low grade SIL is greater than the mean and that of the high grade SIL is less than the mean.

Figure 6:
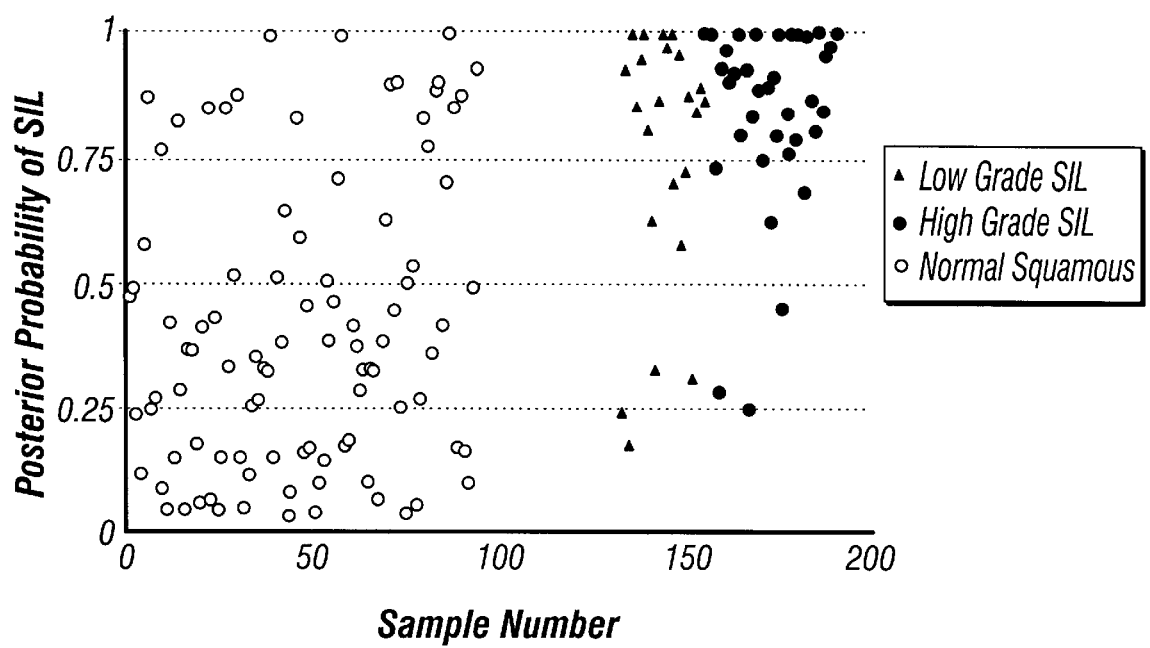
FIG. 6. A plot of the posterior probability of belonging to the SIL category of all SILs and normal squamous epithelia from the calibration set. Evaluation of the misclassified SILs indicates that one samples with CIN III, two with CIN II, two with CIN I and two with HPV are incorrectly classified.

Principal Component Analysis and Logistic Discrimination:

Constituent algorithm (1) which differentiates Sils from normal squamous tissues. A constituent algorithm based on normalized spectra arranged in series at all three excitation wavelengths provided the greatest discrimination between SILs and normal squamous tissues. The algorithm demonstrated an incremental improvement in sensitivity without sacrificing specificity relative to the previously developed constituent algorithm (1) that employed normalized, mean-scaled spectra at 337 nm excitation only. Multivariate statistical analysis of normalized tissue spectra at all three excitation wavelengths, indicated three principal components show statistically significant differences between SILs and normal squamous tissues (Table 2). These three principal components account collectively for 65% of the total variance of the spectral data set. Logistic discrimination was used to develop a classification algorithm to discriminate between SILs and normal squamous epithelia based on these three informative principal components. Prior probabilities were determined by calculating the percentage of each tissue type from the data set: 62% normal squamous tissues and 38% SILs. The cost of misclassification of SIL was optimized at 0.7. Posterior probabilities of belonging to each tissue type were calculated for all samples from the data set, using the known prior probabilities, cost of misclassification of SILs and the conditional joint probabilities calculated from the normal probability density function. FIG. 6 illustrates the retrospective accuracy of the algorithm applied to the calibration data set. The posterior probability of being classified into the SIL category is plotted for all SILs and normal squamous epithelia. FIG. 6 indicates that 92% of high grade SILs and 83% of low grade SILs are correctly classified with a posterior probability greater than 0.5. Approximately 70% of colposcopically normal squamous epithelia are correctly classified with a posterior probability less than 0.5.

The confusion matrix in Table 3 compares the retrospective accuracy of the algorithm on the calibration data set to its prospective accuracy on the prediction set. In the confusion matrix, the first row corresponds to the histo-pathologic classification and the first column corresponds to the spectroscopic classification of the samples. A prospective evaluation of the algorithm's accuracy indicates that there is a small increase in the proportion of correctly classified low grade SILs and no change in the proportion of correctly classified low grade SILs or normal squamous tissues. Note that the majority of normal columnar tissues and samples with inflammation from both calibration and prediction sets are misclassified as SIL using this algorithm. Evaluation of the misclassified SILs from the calibration set indicates that one sample with CIN III, two with CIN II, two with CIN I and two with HPV are incorrectly classified. From the prediction set, two samples with CIN III, one with CIN II, two with CIN I and one with HPV are incorrectly classified as non-SIL.

TABLE 3

Accuracy of constituent algorithm (1) which differentiates SILs and normal squamous tissues from the calibration and prediction sets. The first column corresponds to the spectroscopic classification and the first row corresponds to the histo-pathologic classification.

|  | Normal Squamous | Normal Columnar | Inflammation | LG SIL | HG SIL |
|---|---|---|---|---|---|
| Classification in Calibration Set |  |  |  |  |  |
| Non SIL | 68% | 8% | 7% | 17% | 9% |
| SIL | 32% | 92% | 93% | 83% | 91% |
| Classification in Prediction Set |  |  |  |  |  |
| Non SIL | 68% | 29% | 21% | 12% | 9% |
| SIL | 32% | 71% | 79% | 88% | 91% |

Figure 7:
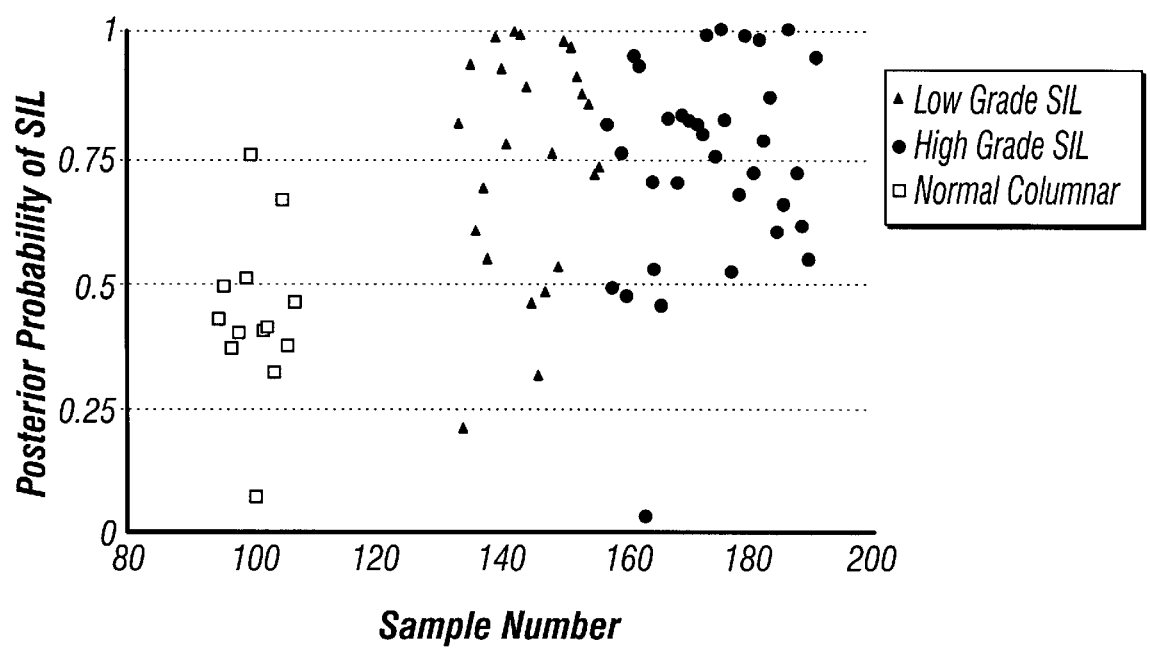
FIG. 7. A plot of the posterior probability of belonging to the SIL category of all SILs and normal columnar epithelia from the calibration data set. Evaluation of the misclassified SILs indicates that three samples with CIN II, three with CIN I and one with HPV are incorrectly classified.

Constituent algorithm (2) which differentiates SILs from normal columnar tissues. The greatest discrimination between SILs and normal columnar epithelia was achieved using a constituent algorithm based on normalized, mean-scaled spectra at all three excitation wavelengths. This algorithm demonstrated a substantially improved sensitivity for a similar specificity relative to the previously developed constituent algorithm (2) which used normalized, mean-scaled spectra at 380 nm excitation, only. Multivariate statistical analysis of a combination of normalized, mean-scaled tissue spectra at all three excitation wavelengths resulted in four principal components that demonstrate statistically significant differences between SILs and normal columnar epithelia (Table 2). These four principal components collectively account for 80% of the total variance of the spectral data set. Logistic discrimination was employed to develop a classification algorithm to discriminate between SILs and normal columnar epithelia. The prior probabilities were determined to be: 28% normal columnar tissues and 72% SILs. The optimized cost of misclassification of SIL was equal to 0.58. Posterior probabilities of belonging to each tissue type were calculated for all samples from the data set. FIG. 7 illustrates the retrospective accuracy of the algorithm applied to the calibration data set. The posterior probability of being classified into the SIL category is plotted for all SILs and normal columnar samples examined. FIG. 7 graphically indicates that 91% of high grade SILs and 83% of low grade SILs have a posterior probability that is greater than 0.5. 76% of colposcopically normal columnar epithelia are correctly classified with a posterior probability less than 0.5.

The confusion matrix in Table 4 compares the retrospective accuracy of the constituent algorithm on the calibration data set to its prospective accuracy on the prediction set. The prospective accuracy of the algorithm (Table 4) indicates that there is a small increase in the proportion of correctly classified low grade SILs and a small decrease in the proportion of correctly classified high grade SILs; there is approximately a 10% decrease in the proportion of correctly classified normal columnar tissues. Note that the majority of normal squamous tissues and samples with inflammation from both the calibration and prediction sets are misclassified as SIL using this algorithm. Evaluation of the misclassified SILs from the calibration set indicates that three samples with CIN II, three with CIN I and one with HPV are incorrectly classified. From the prediction set, two samples with CIN III, three with CIN II, and three with CIN I are incorrectly classified.

TABLE 4

Accuracy of constituent algorithm (2) which differentiates SILs and normal columnar tissues from the calibration and prediction sets. The first column corresponds to the spectroscopic classification and the first row corresponds to the histo-pathologic classification.

|  | Normal Squamous | Normal Columnar | Inflammation | LG SIL | HG SIL |
|---|---|---|---|---|---|
| Classification in Calibration Set |  |  |  |  |  |
| Non SIL | 7% | 77% | 27% | 17% | 9% |
| SIL | 93% | 23% | 73% | 83% | 91% |
| Classification in Prediction Set |  |  |  |  |  |
| Non SIL | 5% | 64% | 27% | 13% | 14% |
| SIL | 95% | 36% | 73% | 87% | 86% |

Figure 8:
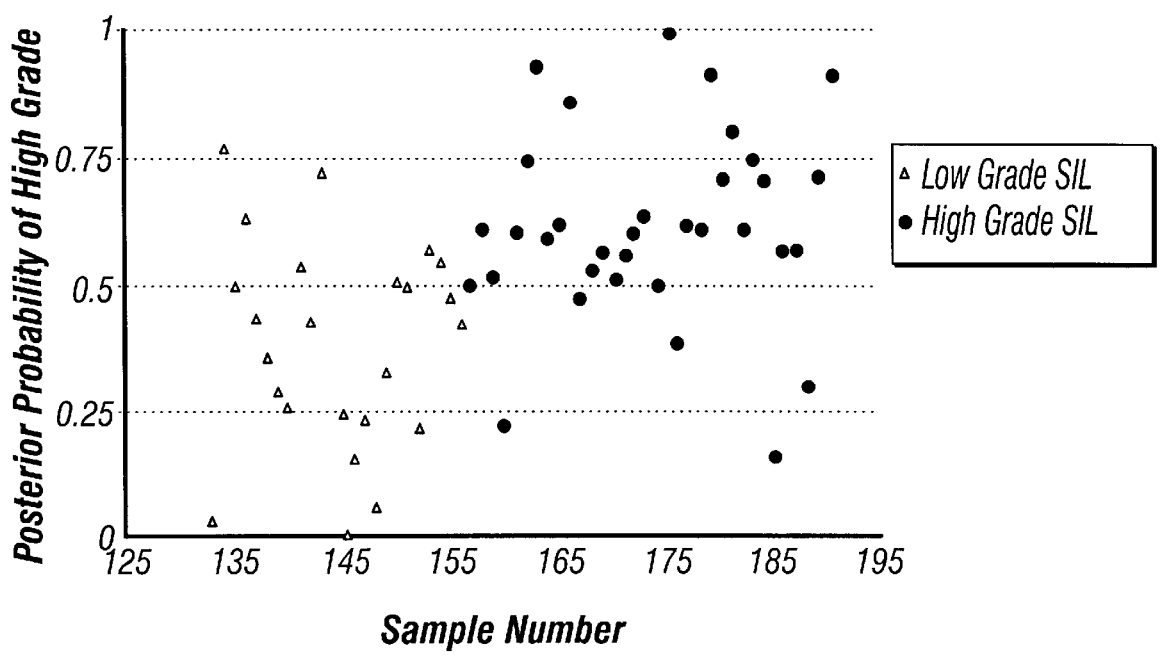
FIG. 8. A plot of the posterior probability of belonging to the HG SIL category of all SILs from the calibration set. Evaluation of the misclassified HG SILs indicates that three samples with CIN III and three with CIN are incorrectly classified as LG SILs; five samples with CIN I and two with HPV are misclassified as HG SIL.

Constituent algorithm (3) which differentiates High Grade SILs and Low Grade SILs. A combination of normalized spectra at all three excitation wavelengths significantly enhanced the accuracy of the previously developed constituent algorithm (3) which differentiated high SILs from low grade SILs using normalized spectra at 460 nm excitation. Multivariate statistical analysis of normalized spectra at all three excitation wavelengths resulted in four statistically significant principal components, that account collectively for 67% of the total variance of the spectral data set (Table 2). Again, a probability based classification algorithm was developed to differentiate high grade SILs from low grade SILs. The prior probability was: 40% low grade SILs and 60% high grade SILs. The optimal cost of misclassification of high grade SIL was equal to 0.51. Posterior probabilities of belonging to each tissue type were calculated. FIG. 8 illustrates the retrospective accuracy of the algorithm applied to the calibration data set. The posterior probability of being classified into the high grade SIL category is plotted for all SILs evaluated. FIG. 8 indicates that 83% of high grade SILs have a posterior probability greater than 0.5, and 70% of low grade SILs have a posterior probability less than 0.5.

The confusion matrix in Table 5 compares the retrospective accuracy of the constituent algorithm on the calibration set to its prospective accuracy on the prediction set. Its prospective accuracy indicates that there is a 5% decrease in the proportion of correctly classified low grade SILs and no change in the proportion of correctly classified high grade SILs. From the calibration set, six high grade SILs are misclassified; three samples with CIN III and three with CIN II are misclassified as low grade SIL. The misclassified low grade SILs comprise of five samples with CIN I and two with HPV. From the prediction set, five high grade SILs are misclassified; two have CIN III and three have CIN II. Of the ten misclassified low grade SILs from the prediction set, seven have CIN I and three have HPV.

TABLE 5

Accuracy of constituent algorithm (3) which differentiates high grade SILs and low grade SILs from the calibration and prediction sets. The first column corresponds to the spectroscopic classification and the first row corresponds to the histo-pathologic classification.

|  | LG SIL | HG SIL |
|---|---|---|
| Classification in Calibration Set |  |  |
| LG SIL | 69% | 17% |
| HG SIL | 31% | 83% |
| Classification in Prediction Set |  |  |
| LG SIL | 63% | 19% |
| HG SIL | 37% | 81% |

"Full-parameter" composite screening and diagnosfic algorithms:

A composite screening algorithm was developed to differentiate SILs and non-SILs (normal squamous and columnar epithelia and inflammation) and a composite diagnostic algorithm was developed to differentiate high grade SILs from non-high grade SILs (low grade SILs, normal epithelia and inflammation). The effective accuracy of both composite algorithms were compared to those of the constituent algorithms from which they were developed and to the accuracy of current detection modalities [5,9].

A composite screening algorithm which discriminates between SILs and non SILs:

A composite screening algorithm to differentiate SILs from non-SILs was developed using a combination of the two constituent algorithms: algorithm (1) which differentiates SILs from normal squamous tissues and algorithm (2) which differentiates SILs from normal columnar epithelia. The optimal cost of misclassification of SIL was equal to 0.66 for constituent algorithm (1) and 0.64 for constituent algorithm (2). Only the costs of misclassification of SIL of the two constituent algorithms was altered for the development of the composite screening algorithm. These costs were selected to minimize the total number of misclassified samples.

The accuracy of the composite screening algorithm on the calibration and prediction data sets is illustrated in the confusion matrix in Table 6. Examination of the confusion matrix indicates that the algorithm correctly classifies approximately 90% of high grade SILs and 75% of low grade SILs from the calibration data set. Furthermore, approximately, 80% of normal squamous tissues and 70% of normal columnar epithelia from the calibration set are correctly classified. Evaluation of the prediction set indicates that there is a small change in the proportion of correctly classified high grade SILs and low grade SILs. There is a negligible change in the correct classification of normal squamous and columnar tissues. Note that while 80% of samples with inflammation from the calibration set are incorrectly classified as SIL, only 43% of these samples from the prediction set are incorrectly classified.

TABLE 6

Accuracy of the original composite algorithm which differentiates SILs and non SILs from the calibration and prediction sets. The first column corresponds to the spectroscopic classification and the first row corresponds to the histo-pathologic classification.

|  | Normal Squamous | Normal Columnar | Inflammation | LG SIL | HG SIL |
|---|---|---|---|---|---|
| Classification in Calibration Set | | | | | |
| Non SIL | 79% | 69% | 20% | 26% | 11% |
| SIL | 21% | 31% | 80% | 74% | 89% |
| Classification in Prediction Set | | | | | |
| Non SIL | 75% | 69% | 57% | 25% | 14% |
| SIL | 25% | 31% | 43% | 75% | 86% |

A comparison of the accuracy of the composite screening algorithm (Table 6) to that of each of the constituent algorithms (1) (Table 3) and (2) (Table 4) on the same spectral data set indicates that in general, there is less than a 10% decrease in the proportion of correctly classified SILs using the composite screening algorithm relative to using either of the constituent algorithms independently. Note, however, that the proportion of correctly classified normal (squamous and columnar) epithelia is substantially higher using the composite algorithm relative to using either of the constituent algorithms independently. These results confirm that utilization of a combination of the two constituent algorithms, significantly reduces the false-positive rate relative to that using each algorithm independently. Evaluation of the spectroscopically misclassified SILs from the calibration set (Table 6) indicates that only one sample with CIN III, three with CIN II, two with CIN I and four with HPV are incorrectly classified. From the prediction data set (Table 6), two samples with CIN III, four with CIN II, three with CIN I and one sample with HPV are incorrectly classified.

A composite diagnostic algorithm which differentiates High Grade SILs from non-High Grade SILs:

A composite diagnostic algorithm which differentially detects high grade SILs was developed using a combination of all three constituent algorithms: algorithm (1) which differentiates SILs from normal squamous tissues, algorithm (2) which differentiates SILs from normal columnar epithelia and algorithm (3) which differentiates high grade SILs from low grade SILs. The optimal costs of misclassification of SIL was equal to 0.87 for algorithm (1) and 0.65 for algorithm (2); the optimal cost of misclassification of high grade SIL was equal to 0.49 for algorithm (3). Only the costs of misclassification of SIL of constituent algorithms (1) and (2) and the cost of misclassification of high grade SIL of constituent algorithm (3) were altered during development of the composite diagnostic algorithm. These costs were selected to minimize the total number of misclassified samples.

The results of the composite diagnostic algorithm on the calibration and prediction sets are shown in the confusion matrix in Table 7. The algorithm correctly classifies 80% of high grade SILs, 74% of low grade SILs and more than 80% of normal epithelia. Evaluation of the prediction set using this composite algorithm indicates that there is only a 3% decrease in the proportion of correctly classified high grade SILs and a 7% decrease in the proportion of correctly classified low grade SILs. There is less than a 10% decrease in the proportion of correctly classified normal epithelia. A comparison between the calibration and prediction sets indicates that while more than 70% of samples with inflammation from the calibration data set are incorrectly classified as high grade SIL, only 14% of samples with inflammation from the prediction set are incorrectly identified. Due to the relatively small number of samples examined in this histo-pathologic category, the results presented here do not conclusively establish if the algorithm is capable of correctly identifying inflammation.

TABLE 7

Accuracy of the original composite screening algorithm which discriminates between high grade SILs and non-high grade SILs from the calibration and prediction sets. The first column corresponds to the spectroscopic classification and the first row corresponds to the histo-pathologic classification.

|  | Normal Squamous | Normal Columnar | Inflammation | LG SIL | HG SIL |
|---|---|---|---|---|---|
| Classification in Calibration Set | | | | | |
| Non HG SIL | 84% | 77% | 27% | 74% | 20% |
| HG SIL | 16% | 23% | 73% | 26% | 80% |
| Classification in Prediction Set | | | | | |
| Non HG SIL | 85% | 69% | 86% | 67% | 23% |
| HG SIL | 15% | 31% | 14% | 33% | 77% |

A comparison of the accuracy of the composite diagnostic algorithm to that of constituent algorithm (3) which differentiates high grade SILs from low grade SILs (Table 5) indicates there is less than a 5% decrease in the proportion of correctly classified high grade SILs and a 5% increase in the proportion of correctly classified low grade SILs using the composite diagnostic algorithm relative to using the constituent algorithm (3). Evaluation of the high grade SILs from the calibration set (Table 7) that were incorrectly classified indicates that three samples with CIN III and four with CIN II are incorrectly classified. From the prediction set, four samples with CIN III and five with CIN II are incorrectly classified.

Figure 9A:
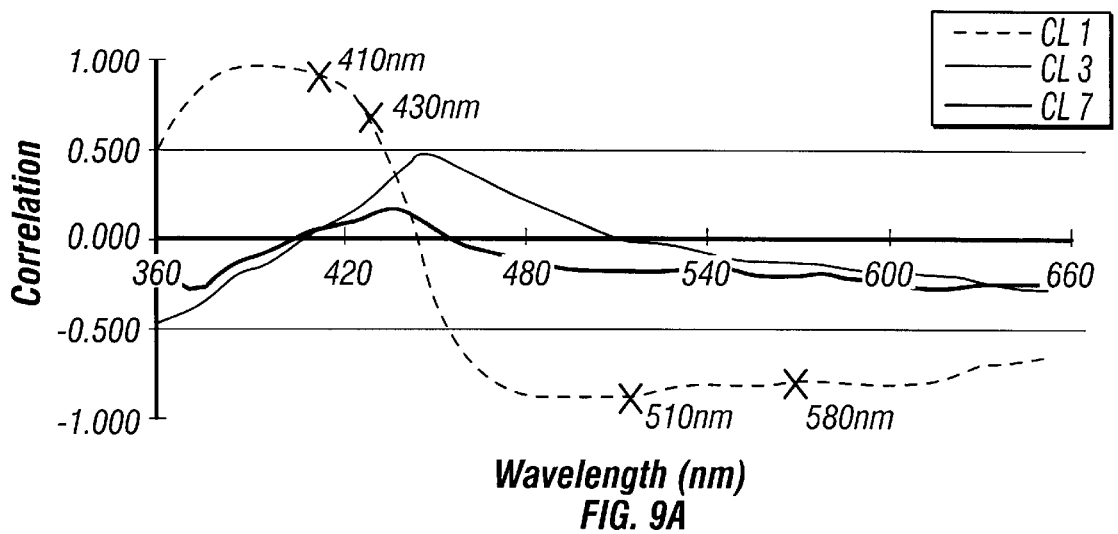
FIGS. 9A, 9B and 9C. Component loadings (CL) of diagnostic principal components of constituent algorithm (1), obtained from normalized spectra at (FIG. 9A) 337, (FIG. 9B) 380 and (FIG. 9C) 460 nm excitation, respectively.
Figure 9B:
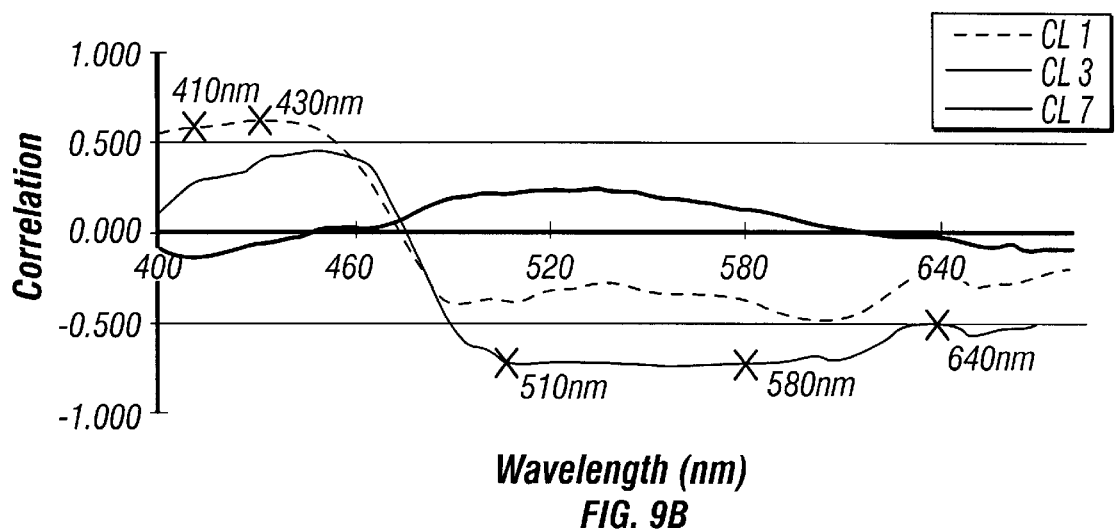
Figure 9C:
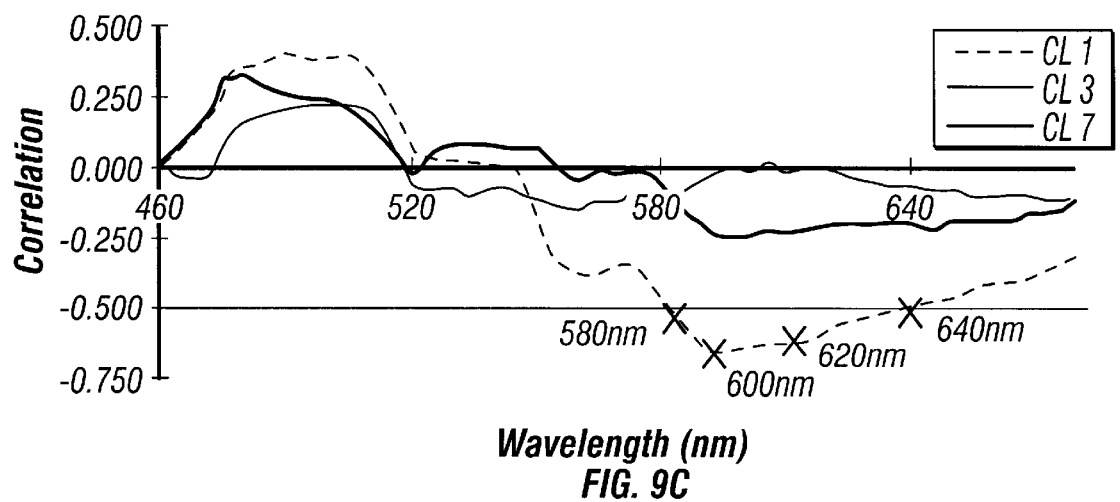
Figure 10A:
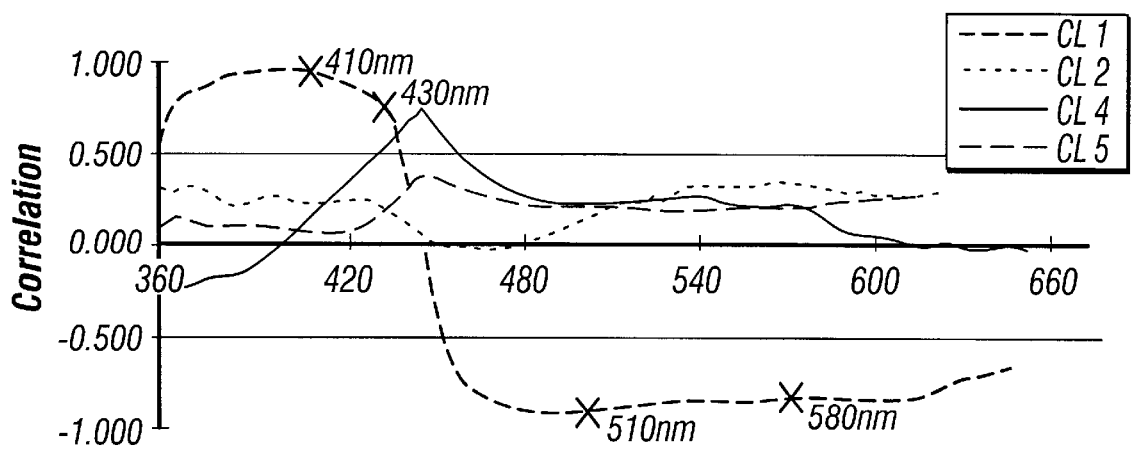
FIGS. 10A, 10B and 10C. Component loadings (CL) of diagnostic principal components of constituent algorithm (2), obtained from normalized, mean-scaled spectra at (FIG. 10A) 337, (FIG. 10B) 380 and (FIG. 10C) 460 nm excitation, respectively.
Figure 10B:
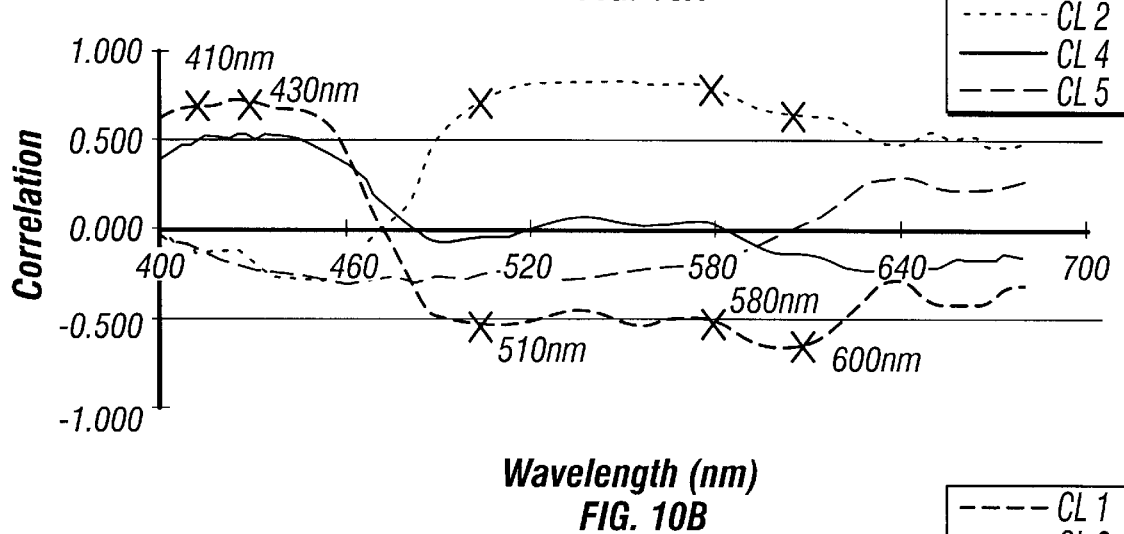
Figure 10C:
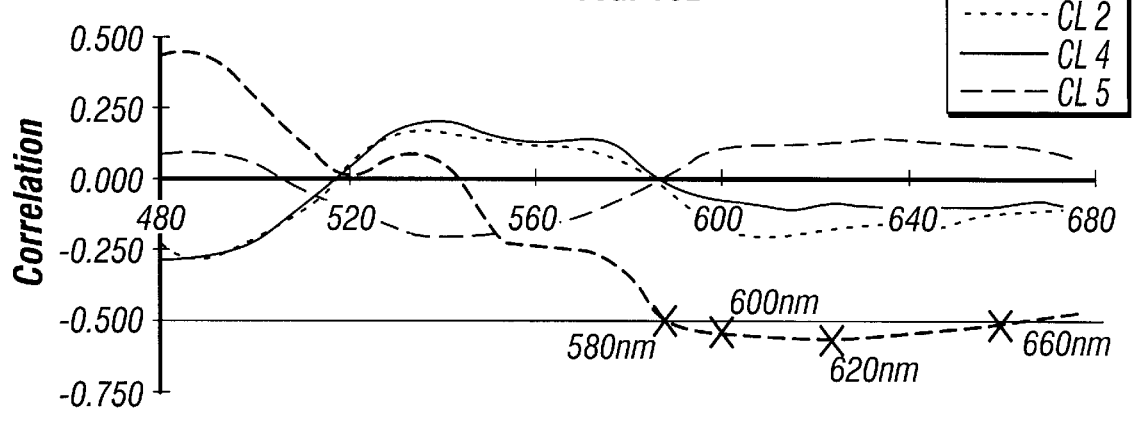

"Reduced-parameter" composite screening and diagnostic algorithms:

Component Loadings. A component loading represents the correlation between each principal component and the original pre-processed fluorescence emission spectra at a particular excitation wavelength. FIGS. 9A, 9B and 9C illustrate component loadings of the diagnostically relevant principal components of constituent algorithm (1) obtained from normalized spectra at 337, 380 and 460 nm excitation, respectively. FIGS. 10A, 10B and 10C display component loadings that correspond to the diagnostically relevant principal components of constituent algorithm (2) obtained from normalized, mean-scaled spectra at 337, 380 and 460 mn excitation, respectively. Finally, FIGS. 11A, 11B and 11C display the component loadings corresponding to the diagnostically relevant principal components of constituent algorithm (3), obtained from normalized spectra at 337, 380 and 460 nm excitation, respectively. In each graph shown, the abscissa corresponds to the emission wavelength range at a particular excitation wavelength and the ordinate corresponds to the correlation coefficient of the component loading. Correlation coefficients of the component loading above 0.5 and below −0.5 are considered to be significant.

Figure 11A:
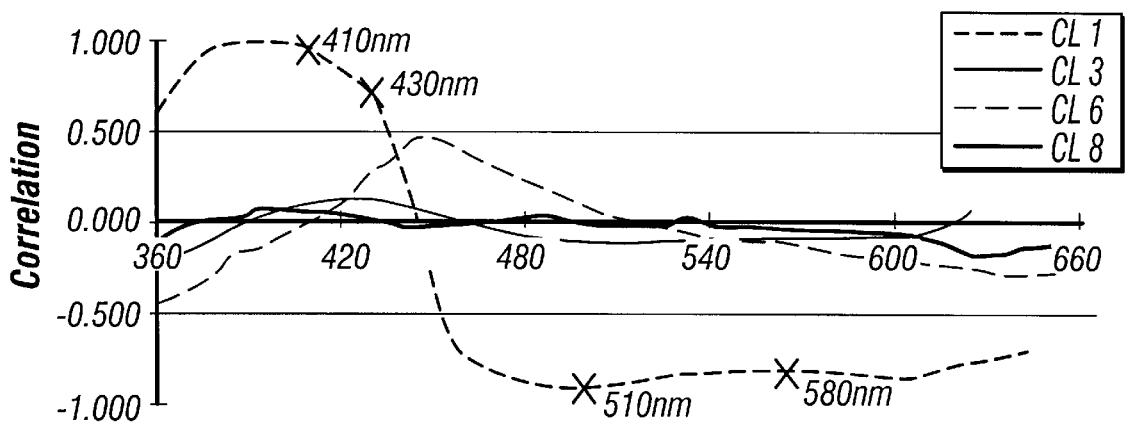
FIGS. 11A, 11B and 11C. Component loadings (CL) of diagnostic principal components of constituent algorithm (3), obtained from normalized spectra at (A) 337, (B) 380 and (C) 460 nm excitation, respectively.

FIGS. 9A, 10A and 11A display component loadings of principal components of constituent algorithms (1), (2) and (3), respectively, obtained from pre-processed spectra at 337 nm excitation. A closer examination indicates that component loading 1 is nearly identical for all three algorithms. Evaluation of this loading indicates that it is positively correlated with corresponding emission spectra over the wavelength range 360–440 nm and negatively correlated with corresponding emission spectra over the wavelength range 460–660 nm. All remaining principal components of all three algorithms display a correlation between −0.5 and 0.5, except component loading 4 of algorithm (2) (FIG. 10A) which displays a positive correlation of 0.75 with the corresponding emission spectra at 460 nm.

Figure 11B:
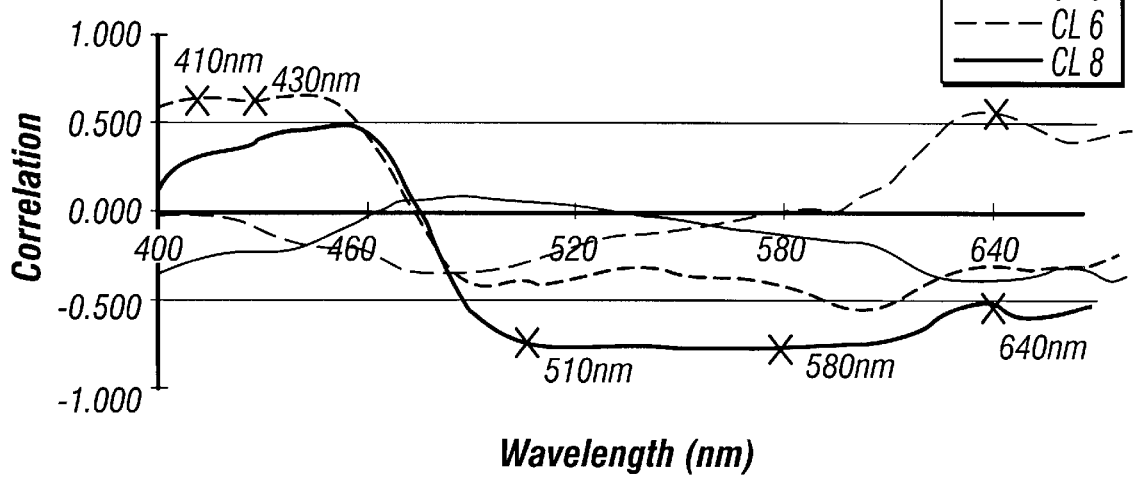

FIGS. 9B, 10B and 11B display component loadings that correspond to the diagnostically relevant principal components of constituent algorithms (1), (2) and (3), respectively obtained from pre-processed spectra at 380 nm excitation. Component loading 1 of all three algorithms is positively correlated with corresponding emission spectra over the wavelength range, 400–450 nm. Between 500–600 nm, only component loading 1 of algorithm (2) (FIG. 10B) is correlated negatively with corresponding emission spectra. However, examination of component loading 3 of algorithm (1) (FIG. 9B) and algorithm (3) (FIG. 11B) indicates that they are also negatively correlated with corresponding emission spectra from 500–600 nm. Only component loading 2 of algorithm (2) (FIG. 10B) is positively correlated with corresponding emission spectra from 500–600 nm. Also note that component loading 3 of algorithm (1) (FIG. 9B) and component loadings 3 and 6 of algorithm (3) (FIG. 11B) display a positive correlation with corresponding emission spectra at approximately 640 nm.

Figure 11C:
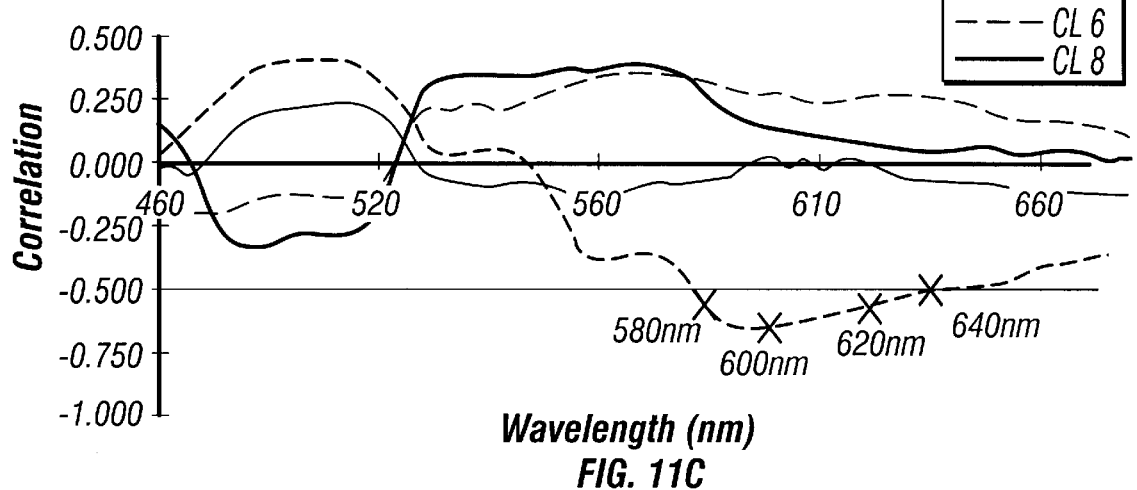

FIGS. 9C, 10C and 11C display component loadings that correspond to the diagnostic principal components of constituent algorithms (1), (2) and (3), respectively obtained from pre-processed spectra at 460 nm excitation. Note that only component loading I displays a negative correlation (<−0.5) with corresponding emission spectra for all three algorithms. This component loading is correlated with corresponding emission spectra over the wavelength range 580–660 nm. The remaining principal components of all three algorithms display a correlation between −0.5 and 0.5.

The component loadings at all three excitation wavelengths of all three constituent algorithms were evaluated to select fluorescence intensities at a minimum number of excitation-emission wavelength pairs required for the previously developed constituent and composite algorithms to perform with a minimal decrease in classification accuracy. Portions of the component loadings of the three constituent algorithms most highly correlated (correlation>0.5 or<−0.5) with corresponding emission spectra at each excitation wavelength were selected and the reduced data matrix was then used to regenerate and evaluate the constituent and composite algorithms. It was iteratively determined that fluorescence intensities at a minimum of 15 excitation-emission wavelength pairs are required to re-develop constituent and composite algorithms that demonstrate a minimum decrease in classification accuracy. At 337 nm excitation, fluorescence intensities at two emission wavelengths between 360–450 nm and intensities at two emission wavelengths between 460–660 nm were selected. At 380 nm excitation, intensities at two emission wavelengths between 400–450 nm and intensities at four emission wavelengths between 500–640 nm were selected. Finally, at 460 nm excitation, fluorescence intensities at five emission wavelengths over the range 580–660 nm was selected. Table 8a lists these excitation-emission wavelength pairs for each of the three constituent algorithms, (1), (2) and (3). These excitation-emission wavelength pairs are also indicated on the component loading plots in FIGS. 9–11. The bandwidth at each emission wavelength is 10 nm.

TABLE 8a

Fluorescence intensities at 18 excitation-emission wavelength pairs needed to re-develop the three constituent algorithms (1), (2) and (3) with a minimal decrease in classification accuracy.

| Algorithm (1) ($\lambda_{exc}$, $\lambda_{emm}$) | Algorithm (2) ($\lambda_{exc}$, $\lambda_{emm}$) | Algorithm (3) ($\lambda_{exc}$, $\lambda_{emm}$) |
| --- | --- | --- |
| 337,410 nm | 337,410 nm | 337,410 nm |
| 337,430 nm | 337,430 nm | 337,430 nm |
| 337,460 nm | 337,460 nm | 337,460 nm |
| 337,510 nm | 337,510 nm | 337,510 nm |
| 337,580 nm | 337,580 nm | 337,580 nm |
| 380,410 nm | 380,410 nm | 380,410 nm |
| 380,430 nm | 380,430 nm | 380,430 nm |
| 380,460 nm | 380,460 nm | 380,460 nm |
| 380,510 nm | 380,510 nm | 380,510 nm |
| 380,580 nm | 380,580 nm | 380,580 nm |
| 380,640 nm | 380,600 nm | 380,640 nm |
| 460,510 nm | 460,510 nm | 460,510 nm |
| 460,580 nm | 460,580 nm | 460,580 nm |
| 460,600 nm | 460,600 nm | 460,600 nm |
| 460,620 nm | 460,620 nm | 460,620 nm |
| 460,640 nm | 460,660 nm | 460,640 nm |

Reduced-parameter composite algorithms:

Using the fluorescence intensities only at the selected excitation-emission wavelength pairs, the three constituent algorithms were re-developed using the same formal analytical process as was done previously using the entire fluorescence emission spectra at all three excitation wavelengths (FIG. 2). The three constituent algorithms were then independently optimized using the calibration set and tested prospectively on the prediction data set. They were combined as described previously into composite screening and diagnostic algorithms. The effective accuracy of these reduced-parameter composite algorithms were compared to that of the full-parameter composite algorithms developed previously using fluorescence emission spectra at all three excitation wavelengths.

TABLE 8b

Fluorescence intensities at 15 excitation-emission wavelength pairs needed to re-develop the three constituent algorithms (1), (2) and (3) with a minimal decrease in classification accuracy.

| Excitation, Emission | Old Bandwidth (nm) | New Bandwidth (nm) |
| --- | --- | --- |
| 337 nm, 410 nm | 10 | 80 |
| 337 nm, 430 nm | 10 | Eliminated |
| 337 nm, 460 nm | 10 | 20 |
| 337 nm, 510 nm | 10 | 60 |
| 337 nm, 580 nm | 10 | 60 |
| 380 nm, 410 nm | 10 | Eliminated |
| 380 nm, 430 nm | 10 | Eliminated |
| 380 nm, 510 nm | 10 | 60 |
| 380 nm, 460 nm | 10 | 20 |
| 380 nm, 580 nm | 10 | 10 |
| 380 nm, 600 nm | 10 | 10 |
| 380 nm, 640 nm | 10 | 10 |
| 460 nm, 510 nm | 10 | 10 |
| 460 nm, 580 nm | 10 | 10 |
| 460 nm, 600 nm | 10 | 10 |
| 460 nm, 620 nm | 10 | 10 |
| 460 nm, 640 nm | 10 | 10 |
| 460 nm, 660 nm | 10 | 10 |

Table 8b contains fluorescence intensities at 15 of the previous 18 excitation-emission wavelength pairs needed to redevelop the three constituent algorithms with a minimal decrease in classification accuracy. This table indicates that three variables are eliminated and the bandwidths of intensities at four excitation-emission wavelength pairs are increased by approximately a factor of four. These results establish that a further reduction in the number of emission variables and an increase in bandwidth minimally affect the classification accuracy of the algorithms. The benefit of eliminating the three emission variables and increasing the bandwidth of four emission variables is that it can reduce the total integration time needed to measure the fluorescence parameters from the tissue.

Table 9 displays the accuracy of the reduced-parameter composite screening algorithm (based on fluorescence intensities at 15 excitation-emission wavelength pairs) which discriminates between SILs and non-SILs applied to the calibration and prediction sets. A comparison between the calibration and prediction data sets indicates that there is less than a 10% decrease in the proportion of correctly classified SILs and normal squamous tissues from the prediction set. Note however that there is a 20% increase in the proportion of correctly classified normal columnar epithelia and a 40% increase in the proportion of correctly classified samples with inflammation from the prediction set.

TABLE 9

Accuracy of the reduced composite screening algorithm which differentiates SILs and non-SILs from the calibration and prediction sets. The first column corresponds to the spectroscopic classification and the first row corresponds to the histo-pathologic classification.

|  | Normal Squamous | Normal Columnar | Inflammation | LG SIL | HG SIL |
|---|---|---|---|---|---|
| Classification in Calibration Set | | | | | |
| Non SIL | 73% | 46% | 13% | 17% | 15% |
| SIL | 27% | 54% | 87% | 83% | 85% |
| Classification in Prediction Set | | | | | |
| Non SIL | 72% | 64% | 50% | 25% | 11% |
| SIL | 28% | 36% | 50% | 75% | 89% |

The accuracy of the reduced-parameter composite screening algorithm (Table 9) was compared to that of the full-parameter composite screening algorithm (Table 6) applied to the same spectral data set. A comparison indicates that in general there is less than a 10% decrease in the accuracy of the reduced-parameter composite algorithm relative to that of the full-parameter composite screening algorithm, except for a 20% decrease in the proportion of correctly classified normal columnar epithelia from the calibration set tested using the reduced-parameter composite screening algorithm (Table 9).

Table 10 displays the accuracy of the reduced-parameter composite diagnostic algorithm that differentially identifies high grade SILs from the calibration and prediction sets. A comparison of sample classification between the calibration and prediction data sets indicates that there is negligible change in the proportion of correctly classified high grade, low grade SILs and normal squamous epithelia. Note that there is approximately a 20% increase in the proportion of correctly classified normal columnar epithelia and samples with inflammation from the prediction set.

TABLE 10

Accuracy of reduced composite diagnostic algorithm which differentiates high grade SILs from non-high grade SILs from the calibration and prediction sets. The first column corresponds to the spectroscopic classification and the first row corresponds to the histo-pathologic classification.

|  | Normal Squamous | Normal Columnar | Inflammation | LG SIL | HG SIL |
|---|---|---|---|---|---|
| Classification in Calibration Set | | | | | |
| Non HG SIL | 79% | 62% | 40% | 65% | 23% |
| HG SIL | 21% | 38% | 60% | 35% | 77% |
| Classification in Prediction Set | | | | | |
| Non HG SIL | 82% | 86% | 64% | 63% | 20% |
| HG SIL | 18% | 14% | 36% | 37% | 80% |

A comparison of the composite diagnostic algorithm based on the reduced emission variables (Table 10) to that using fluorescence emission spectra at all three excitation wavelengths (Table 7) applied to the same spectral data set indicates that in general, the accuracy of the reduced-parameter composite diagnostic algorithm is within 10% of that reported for the full-parameter composite diagnostic algorithm. However, a comparison between Tables 7 and 10 indicates that there is approximately a 15% decrease and a 20% increase in the proportion of correctly classified normal columnar epithelia from the calibration and prediction sets (Table 10), respectively which were tested using the reduced-parameter composite diagnostic algorithm. The opposite trend is observed for samples with inflammation tested using the reduced-parameter composite diagnostic algorithm (Table 10).

Table 11 compares the sensitivity and specificity of the full-parameter and reduced-parameter composite algorithms to that of Pap smear screening [5] and colposcopy in expert hands [9]. Table 11 indicates that the composite screening algorithms have a similar specificity and a significantly improved sensitivity relative to Pap smear screening [5]. A comparison of the sensitivity of the composite screening algorithms to that of colposcopy in expert hands for differentiating SILs from non SILs indicates that these algorithms demonstrate a 10% decrease in sensitivity, but a 20% improvement in specificity. The composite diagnostic algorithms and colposcopy in expert hands discriminate high grade SILs from non-high grade SILs with a very similar sensitivity and specificity. A comparison between the full-parameter and reduced-parameter composite algorithms indicates that the algorithms based on the reduced emission variables demonstrate a similar classification accuracy relative to those that employ fluorescence emission spectra at all three excitation wavelengths.

TABLE 11

Comparison of accuracy of composite screening and diagnostic algorithms to that of Pap smear screening and colposcopy in expert hands.

| | SILs vs. NON SILs | | HG SIL vs. Non HG SIL | |
|---|---|---|---|---|
| Classification | Sensitivity | Specificity | Sensitivity | Specificity |
| Pap Smear | 62% ± 23 | 68% ± 21 | N/A | N/A |
| Colposcopy in Expert Hands | 94% ± 6 | 48% ± 23 | 79% ± 23 | 76% ± 13 |

TABLE 11-continued

Comparison of accuracy of composite screening and diagnostic algorithms to that of Pap smear screening and colposcopy in expert hands.

| Classification | SILs vs. NON SILs | | HG SIL vs. Non HG SIL | |
|---|---|---|---|---|
| | Sensitivity | Specificity | Sensitivity | Specificity |
| Original Composite Algorithm | 82% ± 1.4 | 68% ± 0.0 | 79% ± 2 | 78% ± 6 |
| Reduced Composite Algorithm | 84% ± 1.5 | 65% ± 2 | 78% ± 0.7 | 74% ± 2 |

CLINICAL METHODS

In a clinical setting, the following exemplary steps are carried out to perform the composite screening algorithm in accordance with the present invention:

The instrument (FIG. 1) is turned on and calibrated. Next, the prior probability that the patient to be measured has SIL is entered. This probability may be derived from statistics from the general population, or may be derived from patient-specific data collected, for example, from a prior colposcopy. Next, a speculum is inserted and the cervix is observed. Acetic acid may be applied to the cervix, if desired.

The probe is directed to the cervix, ensuring that areas desired for screening will be illuminated. Multiple placements of the probe may be necessary. Using the probe, the cervix is illuminated with excitation at approximately 337 nm, 380 nm and 460 nm. The probe will record resulting fluorescence data.

Data from each spatial location assessed is analyzed to indicate whether the tissue is SIL or not. Analysis steps carried out include:

1. Data recorded from each spatial location on the cervix is pre-processed in two ways: normalization, and normalization followed by mean scaling. Similarly pre-processed data obtained at each excitation wavelength are concatenated into a vector for each spatial location assessed.
2. The normalized data vector from each site (Dn') is multiplied by the reduced eigenvector matrix stored in memory (Cn'). Cn' contained only those eigenvectors which displayed statistically significant differences for samples to be classified by constituent algorithm 1.
3. The posterior probabilities that a sample is SIL or normal squamous epithelium are calculated using Bayes theorem. In this calculation, the mean values and standard deviations of the PC scores for normal squamous epithelium and SILs and optimal costs of misclassification stored in memory and the entered prior probability are used.
4. The normalized, mean-scaled prediction data vector (Dnm') is multiplied by the reduced eigenvector matrix from normalized, mean-scaled spectral data stored in memory (Cnm'). Cnm' contains only those eigenvectors which displayed statistically significant differences for samples to be classified by constituent algorithm 2.
5. The posterior probabilities that a sample is SIL or normal columnar epithelium are calculated using Bayes theorem. In this calculation, the mean values and standard deviations of the PC scores for normal columnar epithelium and SILs and optimal costs of misclassification stored in memory and entered prior probabilities are used.
6. Using constituent algorithm 1, sites with a posterior probability of being normal squamous epithelium greater than a threshold value are classified as non-SIL. Remaining sites are classified based on the output of constituent algorithm 2. Using constituent algorithm 2, sample with a posterior probability of being normal columnar epithelium greater than a threshold are classified as non-SIL. The remaining samples are classified as SIL. These tissue classifications may then be displayed in an easily understandable way, for example, by displaying an image of the cervix with the different tissue types displayed as different colors.

To use the composite diagnostic algorithm of the present invention in clinical practice, the following exemplary steps are carried out:

The instrument (FIG. 1) is turned on and calibrated. The prior probability that the patient to be measured has SIL and HGSIL is entered. Once again, this probability may be derived from statistics from the general population, or may be derived from patient-specific data collected, for example, from a prior colposcopy. Next, a speculum is inserted and the cervix is observed. Acetic acid may be applied to the cervix, if desired.

The probe is directed to the cervix, ensuring that areas desired for screening will be illuminated. Multiple placements of the probe may be necessary. Using the probe, the cervix is illuminated with excitation at approximately 337 nm, 380 nm and 460 nm. The probe will record resulting fluorescence data.

Data from each spatial location assessed is analyzed to indicate whether the tissue is HGSIL or not. Analysis steps carried out include:

1. Data recorded from each spatial location on the cervix is pre-processed in two ways: normalization, and normalization followed by mean scaling. Similarly pre-processed data obtained at each excitation wavelength are concatenated into a vector for each spatial location assessed.
2. The normalized data vector from each site (Dn') is multiplied by the reduced eigenvector matrix stored in memory (Cn'). Cn' contained only those eigenvectors which displayed statistically significant differences for samples to be classified by constituent algorithm 1.
3. The posterior probabilities that a sample is SIL or normal squamous epithelium are calculated using Bayes theorem. In this calculation, the mean values and standard deviations of the PC scores for normal squamous epithelium and SILs and optimal costs of misclassification stored in memory and the entered prior probability are used.
4. The normalized, mean-scaled prediction data vector (Dnm') is multiplied by the reduced eigenvector matrix from normalized, mean-scaled spectral data stored in memory (Crn'). Cnm' contains only those eigenvectors which displayed statistically significant differences for samples to be classified by constituent algorithm 2.
5. The posterior probabilities that a sample is SIL or normal columnar epithelium are calculated using Bayes theorem. In this calculation, the mean values and standard deviations of the PC scores for normal columnar epithelium and SILs and optimal costs of misclassification stored in memory and entered prior probabilities are used.
6. The normalized prediction data vector (Dn') is multiplied by the reduced eigenvector matrix from normalized spectral data of the calibration set (Cn'). Cn' contains only those eigenvectors which displayed statistically significant differences for samples to be classified by constituent algorithm 3.
7. The posterior probabilities that a sample HGSIL or LGSIL are calculated using Bayes theorem. In this calculation, the mean values and standard deviations of the PC scores for HGSILs and LGSILs and optimal costs of misclassification stored in memory and entered prior probabilities are used.
8. Using constituent algorithm 1, sample with a posterior probability of being normal squamous epithelium greater than a threshold are classified as non-SIL. Remaining samples are classified based on the output of constituent algorithm 2. Using constituent algorithm 2, sample with a posterior probability of being normal columnar epithelium greater than a threshold are classified as non-SIL. Remaining samples are classified based on the output of constituent algorithm 3. Using constituent algorithm 3, samples with a posterior probability of being LGSIL greater than a threshold are classified as LGSIL. The remaining samples are classified as HGSIL. These tissue classifications may then be displayed in an easily understandable way, for example, by displaying an image of the cervix with the different tissue types displayed as different colors.

The present invention has been described with reference to particular exemplary embodiments. However it will be understood by those of ordinary skill in this technology that additions, deletions and changes may be made to the exemplary embodiments without departing from the scope of the present invention.

APPENDIX 1: SPECIFICITY AND SENSITIVITY

Summarized from: Albert A., Harris E. K.: *Multivariate Interpretation of Clinical Laboratory Data,* Marcel Dekker Inc., New York, pp. 75–82, (1987), the disclosure of which is expressly incorporated herein by reference.

Assuming a group of T samples which can be categorized as normal (N samples) or diseased (D samples). A diagnostic test, designed to determine whether the sample is normal or diseased, is applied to each sample. The results of the tests is the continuous variable x, which is then used to determine the sample type. FIG. 22 illustrates a hypothetical distribution of test values for each sample type. A diagnostic method based on this test can easily be defined by choosing a cutoff point, d, such that a sample with an observed value x<d is diagnosed as normal and a sample with an observed value x≧d is diagnosed as abnormal.

Several quantitative measures have been defined to evaluate the performance of this type of method. The first type evaluates the test itself (i.e. measures the ability of the test to separate the two populations, N and D). Sensitivity and specificity are two such measures. The second type is designed to aid in the interpretation of a particular test result (i.e. deciding whether the individual test measurement has come from a normal or diseased sample). Positive and negative predictive value are two measures of this type.

To define these measures, some terminology and notation must be introduced. Referring to Table 12, a sample to be tested can be either normal or diseased; the result of the test for each type of sample can be either negative or positive. True negatives represent those normal with a positive test result. In these cases, the diagnosis based on the rest result is correct. False positives are those normal samples which have a positive test result and false negatives are those diseased samples which have a negative test result. In these cases, the diagnosis based on the test result is incorrect.

TABLE 12

|  | Normal | Diseased | Total Samples |
| --- | --- | --- | --- |
| Test Negative (x < d) | True Negatives (TN) | False Negatives (FN) | Negatives (Neg) |
| Test Positive (x ≧ d) | False Positives (FP) | True Positives (TP) | Positives (Pos) |
| Total Samples | N | D | T |

With this terminology, Table 13 contains a definition of sensitivity and specificity, the two measures which assess the performance of the diagnostic method. Specificity is the proportion of normal samples with a negative test result (proportion of normal samples diagnosed correctly). Sensitivity is the proportion of diseased samples with a positive test result (Proportion of diseased samples correctly diagnosed). Specificity represents the area under the normal sample distribution curve to the left of the cut off point while sensitivity represent the area under the diseased sample distribution curve to the right of the cut off point.

TABLE 13

| Test Measure | Meaning | Calculation |
| --- | --- | --- |
| Specificity | Proportion of normal samples with negative test result | Sp = TN/N |
| Sensitivity | Proportion of diseased samples with positive test result | Se = TP/D |

While sensitivity and specificity characterize the performance of a particular method, another set of statistics is required to interpret the laboratory test result for a given specimen. The positive and negative predictive value quantify the meaning of an individual test result (Table 14). The positive predictive value is the probability that if the test result is positive, the sample is diseased. The negative predictive value is the probability that if the test result is negative, the sample is normal. Positive and negative predictive value are calculated from Bayes rule as outlined in Albert and Harris. Table 14 contains two equivalent formulas for calculation positive and negative predictive value.

TABLE 14

| Measure | Meaning | Calculation 1 | Calculation 2 |
| --- | --- | --- | --- |
| Positive Predictive Value | The probability that, if the test is positive, the sample is diseased | $PV_+ = TP/Pos$ | $PV_+ = DSe/(DSe + N(1 - Sp))$ |
| Negative Predictive Value | The probability that, if the test is negative, the sample is normal | $PV_- = TN/Neg$ | $PV_- = NSp/(NSp + D(1 - Se))$ |

VI. References

The following references, to the extent that they provide exemplary experimental details or other information supplementary to that set forth herein, are incorporated by reference:
1. Wright T. C., Kurman R. J., Ferenczy A. (1994) Cervical Intraepithelial Neoplasia. In *Pathology of the Female Genital Tract.* (Edited by A.Blaustein), New York.
2. American Cancer Society (1995) Cancer Facts and Figures, 12.

3. Kurman R. J., Henson D. E., Herbst A. L., Noller K. L., Schiffinan M. H. (1994) Interim guidelines of management of abnormal cervical cytology. JAMA 271, 1866–1869.
4. World Health Organization, Geneva (1988) Cytological Screening in the Control of Cervical Cancer: Technical Guidelines.
5. Fahey M. T., Irwig L., Macaskill P. (1995) Meta-analysis of Pap test accuracy. American J Epidemiology 141(7), 680–689.
6. Wilkinson E. J. (1990) Pap Smears and screening for cervical neoplasia. Clin Obstet Gynecol 33, 817–825.
7. Koss L. G. (1989) The Papanicolaou test for cervical cancer detection: a triumph and a tragedy. JAMA, 737–743.
8. Burke L., Ducatnan B. S. (1991) Colposcopy, text and atlas. Appleton and Large, Norwalk, Conn.
9. Mitchell M F. (1994) Accuracy of Colposcopy. Consultations in Obstetrics and Gynecology 6(1), 70–73.
10. Richards-Kortum R. R., Rava R. P., Fitzmaurice M., Sivak M. V. (1991) Spectroscopic diagnosis of colonic dysplasia. Photochemistry and Photobiology 53, 777–786.
11. Kapadia C. R., Cutruzzola F. W., O'Brien K. M., Stetz M. L., Enriquez R., Deckelbaum L. I. (1990) Laser-induced fluorescence spectroscopy of human colonic mucosa, Gastroenterology 99, 150–157.
12. Marchesini R., Brambilla M., Pignoli E., Bottiroli G., Croce A. C., Dal Fante M., Spinelli P., Di Palma S. (1992) Light-induced fluorescence spectroscopy of adenomas, adenocarcinomas and non-neoplastic mucosa in human colon, J Photochemistry and Photobiology 14(3), 219–30.
13. Cothren R. M., Richards-Kortum R. R., Rava R. P., Boyce G. A., Doxtader M., Blackman R., Ivanc T., Hayes G. B., Feld M. S., Petras R. E. (1990) Gastrointestinal tissue diagnosis by laser induced fluorescence spectroscopy at endoscopy. Gastrointestinal Endoscopy 36, 105–111.
14. Schomacker K. T., Frisoli J. K., Compton C. C., Flotte T. J., Richter J. M., Nishioka N. S., Deutsch T. F. (1992) Ultraviolet laser induced fluorescence of colonic tissue: basic biology and diagnostic potential. Lasers in Surgery and Medicine 12, 63–78.
15. Hung J., Lam S., LeRiche J. C., Palcic B. (1991) Autofluorescence of normal and malignant bronchial tissue. Lasers in Surgery and Medicine 11(2), 99–105.
16. Lam S., Hung J. Y. C., Kennedy S. M., Leriche J. C., Vedal R., Nelems B., Macaulay C. E., Palcic B. (1992) Detection of dysplasia and carcinoma in situ by ratio fluorimetry. Am Rev Dis 146, 1458–1461.
17. Lam S., Macaulay C., Palcic B. (1993) Detection and localization of early lung cancer by imaging techniques. Chest 103, 12s–14s.
18. Yuanlong Y., Yanming Y., Fuming L., Yufen L., Paozhong M. (1987) Characteristic autofluorescence for cancer diagnosis and its origin, Lasers in Surgery and Medicine 7, 528–532.
19. Montan S., Stromblad L. G. (1987) Spectral characterization of brain tumors utilizing laser-induced fluorescence. Lasers in Life Sciences 1(4), 275–285.
20. Liu C. H., Das B. B., Sha Glassman W. L., Tang G. C., Yoo K. M., Zhu H. R., Akins D. L., Lubicz S. S., Cleary J., Prudente R. (1992) Raman, fluorescence and time-resolved light scattering as optical diagnostic techniques to separate diseased and normal biomedical media. J Photochemistry and Photobiology 16(2), 187–209.
21. Glassman W. S. Liu C. H., Tang G. C., Lubicz S., Alfano R. R. (1992) Ultraviolet excited fluorescence spectra from non-malignant and malignant tissues of the gynecologic tract. Lasers in Life Sciences 5, 49–58.
22. Lohmann W., Mußmann J., Lohmann C., Kunzel W. (1989) Fluorescence of the cervix uteri as a marker for dysplasia and invasive carcinoma. European Journal of Obstetrics and Gynecology and Reproductive Biology 131, 249–253.
23. Mahadevan A., Mitchell M., Silva E., Thomsen S., Richards-Kortum R. R. (1993) Study of the fluorescence properties of normal and neoplastic human cervical tissue. Lasers in Surgery and Medicine 13, 647–655.
24. Braichotte D. R., Wagnieres G. A., Bays R., Monnier P., Van den Bergh H. E. (1995) Clinical pharmacokinetic studies of photofrin by fluorescence spectroscopy in the oral cavity, the esophagus and the bronchi. Cancer 75(11), 2768–78.
25. Gray M. J., Lipson R., Maeck J. V. S., Parker L., Romeyn D. (1967) Use of hematoporphyrin derivative in detection and management of cervical cancer. Am J Obst & Gynec, 766–770.
26. Kennedy J. C. Pottier R. H. (1992) Endogenous protoporphyrin IX, a clinical useful photosensitizer for photodynamic therapy. J Photochem Photobiol B:Biol 14, 275–292.
27. Loh C. S., MacRobert A. J., Bedwell J., Regula J., Krasner N., Bown S. G. (1993) Oral versus intravenous administration of 5-aminolaevulinic acid for photodynamic therapy. British Journal of Cancer 68(1), 41–51.
28. Dillon R. W., Goldstein M (1984) *Multivariate Analysis: Methods and Applications*. John Wiley and Sons, New York.
29. Walpole R. E., Myers R. H. (1987) *Probability and Statistics for Engineers and Scientists*. Decker, New York.
30. Albert A., Harris E. K. (1987) *Multivariate Interpretation of Clinical Laboratory Data*. Marcel Dekker, New York.
31. Devore J. L. (1992) *Probability and Statistics for Engineering and the Science*. Brooks/Cole, Pacific Grove.

APPENDIX II: PRINCIPAL COMPONENTS

Principal Components of Full-Parameter Constituent Algorithm 1 which differentiates SILs from Normal Squamous Tissues. Results reported for calibration set:

| Legend | PC1 | PC3 | PC7 |
|---|---|---|---|
| 1 | 0.630 | -0.576 | 0.288 |
| 1 | 0.590 | -0.460 | 0.294 |
| 1 | 0.902 | -0.849 | -0.034 |
| 1 | 1.150 | -0.678 | -0.104 |
| 1 | -0.413 | -0.179 | -0.150 |
| 1 | -1.190 | -0.171 | -0.225 |
| 1 | 0.489 | -0.049 | -0.138 |
| 1 | 0.200 | -0.163 | -0.130 |
| 1 | -0.889 | -0.457 | -0.104 |
| 1 | 1.060 | -0.256 | -0.253 |
| 1 | 1.290 | -0.360 | -0.143 |
| 1 | -0.113 | -0.220 | -0.162 |
| 1 | 0.610 | -0.108 | -0.031 |
| 1 | -1.460 | -0.554 | -0.129 |
| 1 | 0.468 | -0.314 | -0.262 |
| 1 | 1.290 | -0.422 | -0.093 |
| 1 | 0.174 | -0.690 | -0.156 |
| 1 | 0.428 | -0.798 | -0.225 |
| 1 | 1.290 | -0.742 | -0.362 |
| 1 | 1.410 | -0.530 | -0.154 |
| 1 | 0.284 | -0.518 | -0.331 |
| 1 | 2.220 | -1.400 | -0.137 |
| 1 | 1.160 | -0.191 | -0.116 |
| 1 | 0.231 | -0.099 | -0.247 |
| 1 | 1.640 | -0.271 | -0.249 |
| 1 | 0.538 | -0.179 | -0.112 |
| 1 | -0.864 | 0.032 | 0.118 |
| 1 | 0.130 | -0.273 | -0.135 |
| 1 | 0.152 | 0.029 | -0.010 |
| 1 | -0.978 | -0.702 | 0.095 |
| 1 | 0.635 | -0.120 | -0.079 |
| 1 | 1.660 | -0.683 | 0.002 |
| 1 | 0.934 | -0.401 | -0.150 |
| 1 | 0.692 | 0.015 | 0.144 |
| 1 | 0.018 | -0.363 | -0.094 |
| 1 | 0.401 | -0.085 | 0.071 |
| 1 | 0.187 | -0.146 | -0.043 |
| 1 | 0.132 | -0.142 | -0.175 |
| 1 | -0.593 | -1.260 | -0.103 |
| 1 | 1.140 | -0.565 | -0.353 |
| 1 | -0.349 | -0.423 | -0.147 |

| | | | |
|---|---|---|---|
| 1 | 0.717 | -0.084 | -0.373 |
| 1 | -0.128 | 0.065 | -0.141 |
| 1 | 1.570 | -0.223 | -0.171 |
| 1 | 1.500 | -0.661 | 0.034 |
| 1 | -1.210 | -0.545 | -0.126 |
| 1 | -0.009 | -0.104 | -0.175 |
| 1 | 0.553 | -0.169 | -0.117 |
| 1 | 0.247 | 0.010 | 0.125 |
| 1 | 0.502 | -0.182 | -0.039 |
| 1 | 1.620 | -0.247 | -0.210 |
| 1 | 1.350 | -0.546 | -0.311 |
| 1 | 0.940 | -0.690 | -0.236 |
| 1 | -0.258 | -0.276 | -0.033 |
| 1 | 0.369 | -0.385 | -0.347 |
| 1 | -0.185 | -0.227 | -0.011 |
| 1 | 0.602 | -0.642 | -0.358 |
| 1 | 0.890 | -0.963 | -0.797 |
| 1 | 0.864 | -0.463 | -0.326 |
| 1 | 1.090 | -0.548 | -0.336 |
| 1 | 0.003 | -0.152 | -0.122 |
| 1 | 0.087 | -0.153 | -0.161 |
| 1 | 0.182 | -0.315 | -0.114 |
| 1 | 0.666 | -0.437 | -0.389 |
| 1 | 1.470 | -0.874 | -0.148 |
| 1 | 0.055 | -0.492 | -0.119 |
| 1 | 1.200 | -0.728 | -0.438 |
| 1 | 1.430 | -0.442 | -0.285 |
| 1 | 0.991 | -0.580 | -0.409 |
| 1 | -0.454 | -0.600 | -0.174 |
| 1 | 0.659 | -0.931 | -0.505 |
| 1 | 0.225 | -0.266 | -0.351 |
| 1 | -1.110 | -0.519 | -0.184 |
| 1 | 1.060 | -0.390 | -0.392 |
| 1 | 1.650 | -0.584 | -0.146 |
| 1 | 0.026 | -0.048 | -0.140 |
| 1 | 0.112 | -0.466 | -0.318 |
| 1 | 1.710 | -0.561 | -0.275 |
| 1 | 1.630 | -0.918 | -0.353 |
| 1 | 0.624 | -0.490 | -0.182 |
| 1 | 0.051 | -0.922 | -0.164 |
| 1 | 0.197 | -0.004 | 0.003 |
| 1 | -0.814 | -0.239 | 0.066 |
| 1 | -1.510 | -0.399 | 0.135 |
| 1 | 0.403 | -0.161 | -0.281 |
| 1 | 0.043 | -0.967 | -0.132 |
| 1 | -1.940 | -1.510 | -0.130 |
| 1 | -0.980 | -0.603 | 0.107 |
| 1 | 0.468 | -0.327 | -0.141 |
| 1 | 0.174 | -1.140 | 0.033 |
| 1 | 1.220 | -0.413 | -0.340 |
| 1 | 1.110 | -0.272 | -0.135 |

| | | | |
|---|---|---|---|
| 1 | 0.096 | -0.299 | -0.195 |
| 1 | -1.190 | -0.083 | -0.324 |
| 2 | -0.642 | -0.115 | -0.100 |
| 2 | -0.421 | -0.074 | -0.194 |
| 2 | -0.170 | -0.293 | -0.344 |
| 2 | -1.680 | -1.210 | -0.469 |
| 2 | -0.828 | -0.215 | -0.426 |
| 2 | -0.327 | -0.096 | -0.287 |
| 2 | -1.690 | -0.350 | -0.090 |
| 2 | -1.330 | -0.709 | -0.367 |
| 2 | -0.481 | 0.261 | -0.238 |
| 2 | -0.623 | -0.126 | 0.095 |
| 2 | 0.035 | -0.325 | -0.319 |
| 2 | -0.809 | -0.255 | -0.329 |
| 2 | -0.764 | -0.153 | -0.095 |
| 3 | -1.850 | -1.730 | 0.225 |
| 3 | -0.299 | -0.487 | 0.162 |
| 3 | -0.205 | -0.496 | -0.077 |
| 3 | 1.990 | -1.760 | -0.094 |
| 3 | -0.612 | -0.292 | -0.084 |
| 3 | -1.110 | -1.070 | -0.083 |
| 3 | -1.300 | -0.330 | -0.103 |
| 3 | -0.176 | -0.114 | 0.061 |
| 3 | -1.460 | -0.228 | -0.519 |
| 3 | -0.435 | -0.881 | -0.072 |
| 4 | -0.286 | -0.057 | 0.141 |
| 4 | -1.080 | -0.546 | -0.247 |
| 4 | -1.140 | -0.573 | -0.438 |
| 4 | -0.649 | -0.848 | 0.010 |
| 4 | -1.770 | -1.110 | -0.186 |
| 4 | -1.140 | -0.881 | -0.392 |
| 4 | 1.940 | -1.980 | 0.130 |
| 4 | -0.839 | -0.500 | -0.069 |
| 4 | -1.550 | -0.608 | -0.328 |
| 4 | -0.263 | -0.158 | -0.309 |
| 4 | 1.590 | -0.250 | -0.311 |
| 4 | -1.030 | -0.353 | -0.182 |
| 4 | -1.420 | -0.641 | -0.278 |
| 4 | -0.864 | -0.313 | -0.018 |
| 4 | -0.095 | -0.982 | 0.087 |
| 5 | 0.415 | -0.346 | -0.154 |
| 5 | -1.320 | -0.560 | -0.359 |
| 5 | 0.716 | -0.066 | 0.068 |
| 5 | -1.010 | -0.403 | -0.571 |
| 5 | -0.057 | -1.040 | -0.162 |
| 5 | 0.067 | -0.471 | -0.615 |
| 5 | 0.702 | -1.080 | -0.830 |
| 5 | 0.297 | -0.568 | 0.185 |
| 5 | -0.403 | -0.508 | -0.164 |
| 5 | 1.060 | -1.030 | -0.079 |
| 5 | -0.971 | -0.624 | -0.294 |

| | | | |
|---|---|---|---|
| 5 | -1.300 | -0.254 | -0.693 |
| 5 | -1.200 | -0.041 | -0.474 |
| 5 | -0.276 | 0.347 | -0.453 |
| 5 | 0.183 | -0.273 | -0.343 |
| 5 | -0.616 | -0.661 | -0.506 |
| 5 | -0.318 | -0.323 | -0.240 |
| 5 | -0.406 | -0.773 | -0.154 |
| 5 | -0.451 | -0.297 | -0.447 |
| 5 | 0.557 | -0.088 | -0.262 |
| 5 | -0.208 | -0.863 | -0.223 |
| 5 | -0.258 | 0.027 | -0.437 |
| 5 | -0.400 | -0.813 | -0.122 |
| 6 | -0.382 | -1.460 | 0.152 |
| 6 | -1.370 | -0.247 | -0.609 |
| 6 | -0.616 | -0.256 | -0.112 |
| 6 | 0.390 | -0.182 | -0.235 |
| 6 | -0.546 | -0.424 | -0.129 |
| 6 | 0.768 | -1.170 | -0.515 |
| 6 | -0.770 | -0.906 | -0.002 |
| 6 | -1.810 | -0.883 | -0.097 |
| 6 | 0.026 | -1.210 | -0.334 |
| 6 | -1.060 | -0.393 | -0.111 |
| 6 | -1.370 | -0.783 | -0.251 |
| 6 | 0.880 | -0.476 | -0.368 |
| 6 | -0.589 | -0.346 | -0.384 |
| 6 | 0.662 | -1.040 | -0.347 |
| 6 | -0.292 | -0.048 | -0.470 |
| 6 | -0.106 | -0.239 | -0.073 |
| 6 | -1.020 | -0.816 | -0.129 |
| 6 | -0.484 | -0.425 | -0.207 |
| 6 | -0.834 | -0.521 | -0.006 |
| 6 | -1.340 | -1.860 | -0.283 |
| 6 | -0.084 | -0.197 | -0.125 |
| 6 | -0.733 | -0.689 | -0.253 |
| 6 | -0.788 | -0.409 | -0.028 |
| 6 | -1.280 | -1.410 | -0.298 |
| 6 | -0.816 | -0.099 | -0.078 |
| 6 | -1.160 | -1.060 | 0.185 |
| 6 | -0.434 | -0.092 | -0.075 |
| 6 | -0.139 | -1.300 | -0.195 |
| 6 | -0.768 | 0.120 | -0.300 |
| 6 | -0.951 | -0.441 | -0.219 |
| 6 | -0.392 | -0.307 | -0.727 |
| 6 | -0.015 | 0.071 | -0.171 |
| 6 | -1.430 | -0.619 | -0.127 |
| 6 | -1.110 | -1.070 | -0.104 |
| 6 | -1.360 | -0.504 | -0.699 |

Principal Components of Full-Parameter Constituent Algorithm 2 which differentiates SILs from Normal Columnar Tissues. Results reported for calibration set:

| L | PC1 | PC2 | PC4 | PC5 |
|---|---|---|---|---|
| 1 | 0.413 | -0.096 | -0.067 | -0.134 |
| 1 | 0.763 | -0.119 | -0.089 | 0.078 |
| 1 | 0.674 | 0.403 | -0.184 | 0.040 |
| 1 | 1.100 | 0.472 | -0.308 | 0.210 |
| 1 | 0.381 | 0.166 | 0.253 | -0.064 |
| 1 | -0.309 | -0.278 | -0.048 | -0.080 |
| 1 | 0.664 | -0.169 | -0.038 | -0.021 |
| 1 | -0.083 | -0.204 | 0.161 | -0.003 |
| 1 | -1.210 | -0.193 | -0.096 | -0.109 |
| 1 | 0.053 | -0.105 | 0.207 | 0.083 |
| 1 | 0.258 | -0.055 | 0.162 | -0.217 |
| 1 | 0.021 | -0.009 | -0.110 | 0.127 |
| 1 | 0.357 | 0.091 | 0.072 | 0.112 |
| 1 | -1.020 | -0.412 | -0.765 | -0.043 |
| 1 | -0.089 | -0.065 | -0.025 | 0.045 |
| 1 | 0.842 | 0.141 | -0.168 | -0.017 |
| 1 | 0.020 | 0.016 | 0.009 | 0.047 |
| 1 | 0.263 | 0.199 | 0.016 | 0.127 |
| 1 | 1.190 | 0.055 | -0.406 | -0.087 |
| 1 | 0.913 | 0.102 | -0.215 | -0.359 |
| 1 | 0.685 | 0.127 | 0.152 | 0.159 |
| 1 | 0.224 | -0.241 | 0.032 | 0.071 |
| 1 | 1.070 | 0.314 | -0.017 | -0.022 |
| 1 | 0.914 | -0.262 | 0.391 | -0.103 |
| 1 | 1.790 | -0.233 | -0.561 | -0.166 |
| 1 | 0.557 | 0.127 | -0.101 | 0.017 |
| 1 | -0.310 | -0.323 | -0.217 | -0.136 |
| 1 | 0.422 | 0.134 | 0.046 | 0.005 |
| 1 | 0.164 | -0.325 | 0.074 | 0.010 |
| 1 | -1.050 | 0.274 | -0.081 | -0.224 |
| 1 | 0.845 | -0.057 | -0.089 | 0.163 |
| 1 | 0.733 | -0.462 | -0.653 | -0.422 |
| 1 | 0.084 | -0.271 | 0.128 | 0.041 |
| 1 | 0.792 | -0.338 | 0.092 | -0.166 |
| 1 | 0.560 | 0.264 | 0.209 | -0.040 |
| 1 | 0.535 | 0.180 | 0.189 | 0.013 |
| 1 | 0.318 | 0.209 | 0.133 | 0.137 |
| 1 | 0.521 | 0.174 | 0.058 | 0.179 |
| 1 | 0.067 | 0.747 | -0.188 | 0.072 |
| 1 | 1.300 | -0.134 | -0.288 | -0.060 |
| 1 | -0.049 | 0.134 | 0.312 | -0.153 |
| 1 | 0.494 | 0.152 | 0.079 | 0.033 |
| 1 | 0.183 | -0.462 | 0.144 | 0.071 |
| 1 | 1.420 | 0.051 | -0.340 | -0.033 |
| 1 | 1.300 | -0.384 | -0.421 | -0.279 |
| 1 | -0.383 | 0.239 | -0.255 | -0.165 |
| 1 | 0.341 | -0.111 | -0.067 | 0.114 |

| | | | | |
|---|---|---|---|---|
| 1 | 0.443 | 0.169 | 0.408 | 0.132 |
| 1 | 0.289 | -0.053 | 0.099 | 0.016 |
| 1 | 1.210 | -0.378 | 0.141 | 0.187 |
| 1 | 1.060 | 0.199 | -0.337 | -0.096 |
| 1 | 0.631 | -0.161 | -0.164 | -0.054 |
| 1 | 0.795 | 0.417 | -0.069 | 0.166 |
| 1 | 0.209 | 0.189 | 0.050 | 0.012 |
| 1 | 1.080 | -0.132 | 0.267 | -0.027 |
| 1 | 0.425 | 0.065 | 0.001 | 0.217 |
| 1 | 0.079 | 0.044 | -0.094 | 0.066 |
| 1 | 0.275 | 0.053 | -0.175 | -0.043 |
| 1 | 0.843 | 0.151 | -0.142 | 0.129 |
| 1 | 1.550 | 0.030 | -0.181 | 0.243 |
| 1 | 0.626 | -0.096 | 0.135 | 0.033 |
| 1 | 0.482 | -0.093 | 0.075 | 0.070 |
| 1 | 0.599 | -0.019 | 0.143 | 0.048 |
| 1 | 0.849 | 0.389 | -0.038 | 0.100 |
| 1 | 0.494 | -0.108 | -0.082 | -0.002 |
| 1 | 0.505 | -0.274 | 0.209 | -0.007 |
| 1 | 1.470 | -0.026 | -0.380 | -0.059 |
| 1 | 1.050 | 0.296 | -0.017 | -0.050 |
| 1 | 0.845 | -0.148 | -0.065 | -0.001 |
| 1 | -0.030 | 0.380 | 0.107 | -0.095 |
| 1 | 0.405 | 0.217 | -0.119 | 0.186 |
| 1 | 0.563 | -0.104 | 0.039 | 0.131 |
| 1 | -0.809 | -0.244 | -0.451 | 0.206 |
| 1 | 0.552 | 0.085 | -0.066 | 0.107 |
| 1 | 1.070 | -0.184 | -0.589 | -0.234 |
| 1 | 0.312 | -0.133 | -0.028 | 0.084 |
| 1 | 0.183 | 0.048 | 0.129 | 0.003 |
| 1 | 1.410 | 0.112 | -0.637 | -0.194 |
| 1 | 0.852 | -0.304 | -0.304 | -0.381 |
| 1 | 0.508 | -0.419 | 0.008 | -0.018 |
| 1 | 0.257 | 0.368 | -0.054 | 0.018 |
| 1 | 0.573 | 0.077 | -0.080 | 0.010 |
| 1 | -0.156 | -0.155 | -0.338 | 0.124 |
| 1 | -0.885 | -0.231 | -0.527 | -0.055 |
| 1 | 0.313 | -0.447 | 0.072 | 0.271 |
| 1 | 0.103 | 0.574 | 0.086 | 0.037 |
| 1 | 0.151 | 0.359 | 0.135 | -0.162 |
| 1 | 0.129 | 0.140 | 0.188 | -0.140 |
| 1 | -0.081 | -0.156 | 0.219 | 0.155 |
| 1 | 0.093 | 0.716 | -0.151 | -0.032 |
| 1 | 0.265 | -0.348 | 0.374 | 0.251 |
| 1 | 0.674 | -0.365 | -0.125 | -0.049 |
| 1 | 0.457 | -0.110 | 0.050 | 0.070 |
| 1 | 0.089 | -0.378 | -0.401 | 0.031 |
| 2 | -0.616 | -0.363 | -0.106 | 0.101 |
| 2 | -0.258 | -0.340 | -0.080 | -0.043 |
| 2 | -0.543 | -0.072 | -0.197 | -0.002 |
| 2 | -1.190 | 0.109 | -0.003 | 0.020 |

| | | | | |
|---|---|---|---|---|
| 2 | -0.407 | -0.526 | 0.177 | -0.005 |
| 2 | -0.123 | -0.199 | 0.107 | 0.142 |
| 2 | -0.813 | -0.344 | -0.523 | 0.010 |
| 2 | -1.180 | -0.174 | 0.041 | -0.079 |
| 2 | -0.677 | -0.544 | -0.032 | -0.061 |
| 2 | -0.603 | -0.250 | -0.259 | 0.088 |
| 2 | -0.323 | 0.114 | 0.197 | 0.061 |
| 2 | -1.290 | -0.338 | 0.078 | -0.082 |
| 2 | -0.968 | -0.028 | 0.228 | 0.046 |
| 3 | -0.714 | 0.263 | -0.224 | 0.128 |
| 3 | -0.432 | -0.297 | 0.090 | -0.260 |
| 3 | -0.246 | 0.003 | 0.116 | 0.079 |
| 3 | -0.045 | 0.128 | 0.036 | 0.090 |
| 3 | -0.087 | 0.367 | 0.180 | 0.018 |
| 3 | -0.988 | 0.348 | 0.061 | -0.227 |
| 3 | -1.470 | -0.567 | -0.515 | -0.060 |
| 3 | -0.260 | -0.288 | 0.266 | -0.152 |
| 3 | -1.800 | -0.666 | -0.386 | -0.044 |
| 3 | -0.163 | 0.543 | 0.082 | -0.165 |
| 4 | -0.446 | -0.511 | 0.187 | -0.238 |
| 4 | -0.224 | 0.330 | 0.114 | 0.034 |
| 4 | -1.030 | 0.176 | -0.054 | 0.084 |
| 4 | -0.730 | 0.394 | 0.214 | -0.147 |
| 4 | -1.440 | 0.154 | -0.394 | -0.036 |
| 4 | -0.771 | 0.256 | 0.054 | 0.055 |
| 4 | -0.127 | 0.288 | -0.166 | 0.085 |
| 4 | -0.672 | 0.244 | 0.185 | -0.124 |
| 4 | -0.671 | 0.193 | -0.103 | 0.078 |
| 4 | 0.060 | -0.285 | 0.133 | 0.006 |
| 4 | 1.020 | 0.142 | -0.438 | -0.001 |
| 4 | -0.425 | -0.080 | -0.119 | 0.006 |
| 4 | -0.999 | 0.142 | -0.198 | 0.047 |
| 4 | 0.268 | -0.186 | 0.184 | -0.075 |
| 4 | -0.717 | 0.356 | -0.096 | 0.030 |
| 5 | 0.240 | -0.121 | 0.021 | 0.126 |
| 5 | -0.593 | 0.039 | -0.421 | 0.007 |
| 5 | 0.372 | -0.086 | -0.063 | -0.200 |
| 5 | -1.480 | -0.321 | -0.188 | 0.232 |
| 5 | -0.954 | 0.501 | 0.298 | 0.105 |
| 5 | -0.442 | -0.102 | 0.232 | 0.014 |
| 5 | -0.073 | 0.109 | 0.100 | 0.315 |
| 5 | 0.265 | 0.389 | 0.032 | -0.144 |
| 5 | -0.276 | 0.371 | 0.166 | -0.075 |
| 5 | -0.055 | 0.431 | -0.243 | -0.376 |
| 5 | -0.451 | -0.360 | 0.221 | -0.354 |
| 5 | -1.040 | -0.285 | -0.166 | 0.302 |
| 5 | -0.642 | -0.475 | 0.058 | 0.085 |
| 5 | -0.755 | -0.254 | 0.592 | 0.010 |
| 5 | -0.490 | -0.434 | 0.179 | 0.045 |
| 5 | 0.063 | -0.043 | 0.092 | 0.089 |
| 5 | -0.327 | -0.135 | 0.005 | -0.019 |

| | | | | |
|---|---|---|---|---|
| 5 | 0.043 | 0.292 | 0.345 | -0.252 |
| 5 | -0.109 | -0.355 | 0.106 | 0.298 |
| 5 | 1.010 | -0.267 | -0.130 | 0.085 |
| 5 | -0.457 | 0.147 | 0.117 | -0.196 |
| 5 | 0.130 | 0.181 | 0.331 | 0.119 |
| 5 | -0.551 | 0.157 | 0.103 | -0.121 |
| 6 | -0.668 | 1.010 | 0.133 | 0.016 |
| 6 | -0.601 | -0.219 | -0.273 | 0.268 |
| 6 | -0.488 | -0.070 | -0.079 | -0.058 |
| 6 | 0.045 | 0.046 | 0.046 | -0.072 |
| 6 | -0.278 | 0.004 | -0.230 | -0.055 |
| 6 | -0.156 | 0.620 | 0.129 | 0.208 |
| 6 | -0.553 | 0.533 | 0.069 | -0.216 |
| 6 | -1.190 | -0.493 | -0.774 | 0.083 |
| 6 | -0.735 | 0.701 | 0.163 | -0.019 |
| 6 | -0.619 | 0.066 | -0.068 | -0.078 |
| 6 | -0.926 | 0.028 | 0.101 | -0.023 |
| 6 | 0.361 | 0.116 | -0.041 | -0.064 |
| 6 | -0.339 | 0.180 | 0.181 | -0.054 |
| 6 | 0.488 | 0.172 | -0.086 | 0.000 |
| 6 | -0.271 | -0.517 | 0.171 | 0.199 |
| 6 | 0.269 | -0.207 | 0.095 | -0.099 |
| 6 | -0.136 | 0.233 | 0.077 | -0.103 |
| 6 | 0.066 | -0.330 | 0.455 | -0.310 |
| 6 | -0.660 | 0.283 | 0.093 | -0.132 |
| 6 | -1.400 | 1.460 | -0.371 | 0.665 |
| 6 | 0.296 | 0.131 | -0.031 | 0.090 |
| 6 | -0.235 | -0.047 | -0.327 | 0.147 |
| 6 | -0.529 | -0.019 | 0.127 | -0.117 |
| 6 | -1.510 | 0.623 | 0.091 | 0.344 |
| 6 | 0.064 | -0.064 | -0.030 | -0.076 |
| 6 | -0.373 | 1.040 | -0.099 | -0.280 |
| 6 | -0.075 | -0.130 | 0.077 | -0.130 |
| 6 | 0.479 | 0.206 | -0.047 | 0.080 |
| 6 | -0.092 | -0.433 | 0.087 | 0.045 |
| 6 | -0.364 | 0.010 | -0.046 | 0.126 |
| 6 | -1.220 | -0.321 | 0.804 | 0.698 |
| 6 | -0.196 | -0.155 | 0.300 | 0.123 |
| 6 | -0.347 | -0.111 | -0.024 | -0.097 |
| 6 | -0.479 | -0.206 | 0.047 | -0.080 |
| 6 | -0.078 | 0.406 | 0.047 | 0.227 |

5

Principal Components of Full-Parameter Constituent Algorithm 3 which differentiates HG SILs from LG SILs. Results reported for calibration set.

| L | PC1 | PC3 | PC6 | PC8 |
|---|-----|-----|-----|-----|
| 1 | 0.630 | -0.576 | -0.733 | -0.127 |
| 1 | 0.590 | -0.460 | -0.800 | -0.113 |
| 1 | 0.902 | -0.849 | -0.480 | -1.080 |
| 1 | 1.150 | -0.678 | -1.070 | -0.601 |
| 1 | -0.413 | -0.179 | -0.777 | -0.231 |
| 1 | -1.190 | -0.171 | -0.859 | -0.273 |
| 1 | 0.489 | -0.049 | -0.676 | -0.292 |
| 1 | 0.200 | -0.163 | -0.819 | -0.476 |
| 1 | -0.889 | -0.457 | -0.883 | -0.420 |
| 1 | 1.060 | -0.256 | -0.807 | -0.268 |
| 1 | 1.290 | -0.360 | -0.860 | -0.321 |
| 1 | -0.113 | -0.220 | -0.879 | -0.511 |
| 1 | 0.610 | -0.108 | -0.927 | -0.446 |
| 1 | -1.460 | -0.554 | -1.050 | -0.356 |
| 1 | 0.468 | -0.314 | -1.010 | -0.557 |
| 1 | 1.290 | -0.422 | -0.800 | -0.340 |
| 1 | 0.174 | -0.690 | -0.966 | -0.505 |
| 1 | 0.428 | -0.798 | -0.975 | -0.517 |
| 1 | 1.290 | -0.742 | -0.809 | -0.214 |
| 1 | 1.410 | -0.530 | -0.942 | -0.253 |
| 1 | 0.284 | -0.518 | -0.950 | -0.454 |
| 1 | 2.220 | -1.400 | -0.802 | -0.765 |
| 1 | 1.160 | -0.191 | -0.919 | -0.652 |
| 1 | 0.231 | -0.099 | -0.907 | -0.476 |
| 1 | 1.640 | -0.271 | -0.678 | -0.411 |
| 1 | 0.538 | -0.179 | -0.942 | -0.693 |
| 1 | -0.864 | 0.032 | -0.905 | -0.388 |
| 1 | 0.130 | -0.273 | -1.110 | -0.464 |
| 1 | 0.152 | 0.029 | -0.958 | -0.725 |
| 1 | -0.978 | -0.702 | -1.240 | -0.666 |
| 1 | 0.635 | -0.120 | -0.823 | -0.554 |
| 1 | 1.660 | -0.683 | -0.848 | -0.439 |
| 1 | 0.934 | -0.401 | -0.956 | -0.532 |
| 1 | 0.692 | 0.015 | -0.850 | -0.492 |
| 1 | 0.018 | -0.363 | -0.938 | -0.491 |
| 1 | 0.401 | -0.085 | -0.984 | -0.561 |
| 1 | 0.187 | -0.146 | -1.030 | -0.532 |
| 1 | 0.132 | -0.142 | -1.050 | -0.625 |
| 1 | -0.593 | -1.260 | -1.070 | -0.557 |
| 1 | 1.140 | -0.565 | -0.758 | -0.378 |
| 1 | -0.349 | -0.423 | -0.766 | -0.458 |
| 1 | 0.717 | -0.084 | -0.918 | -0.529 |
| 1 | -0.128 | 0.065 | -0.820 | -0.553 |
| 1 | 1.570 | -0.223 | -0.801 | -0.474 |
| 1 | 1.500 | -0.661 | -0.754 | -0.278 |
| 1 | -1.210 | -0.545 | -0.776 | -0.353 |
| 1 | -0.009 | -0.104 | -0.816 | -0.518 |

| | | | | |
|---|---|---|---|---|
| 1 | 0.553 | -0.169 | -0.939 | -0.618 |
| 1 | 0.247 | 0.010 | -0.968 | -0.611 |
| 1 | 0.502 | -0.182 | -1.010 | -0.522 |
| 1 | 1.620 | -0.247 | -0.887 | -0.497 |
| 1 | 1.350 | -0.546 | -0.791 | -0.528 |
| 1 | 0.940 | -0.690 | -1.040 | -0.574 |
| 1 | -0.258 | -0.276 | -1.020 | -0.645 |
| 1 | 0.369 | -0.385 | -0.836 | -0.745 |
| 1 | -0.185 | -0.227 | -1.060 | -0.527 |
| 1 | 0.602 | -0.642 | -0.865 | -0.293 |
| 1 | 0.890 | -0.963 | -1.510 | -0.591 |
| 1 | 0.864 | -0.463 | -1.050 | -0.461 |
| 1 | 1.090 | -0.548 | -0.932 | -0.358 |
| 1 | 0.003 | -0.152 | -0.927 | -0.361 |
| 1 | 0.087 | -0.153 | -0.861 | -0.595 |
| 1 | 0.182 | -0.315 | -0.965 | -0.411 |
| 1 | 0.666 | -0.437 | -0.994 | -0.330 |
| 1 | 1.470 | -0.874 | -0.725 | -0.089 |
| 1 | 0.055 | -0.492 | -1.000 | -0.383 |
| 1 | 1.200 | -0.728 | -0.907 | -0.348 |
| 1 | 1.430 | -0.442 | -0.902 | -0.446 |
| 1 | 0.991 | -0.580 | -0.889 | -0.315 |
| 1 | -0.454 | -0.600 | -1.040 | -0.611 |
| 1 | 0.659 | -0.931 | -0.672 | -0.599 |
| 1 | 0.225 | -0.266 | -0.918 | -0.373 |
| 1 | -1.110 | -0.519 | -0.988 | -0.279 |
| 1 | 1.060 | -0.390 | -0.991 | -0.485 |
| 1 | 1.650 | -0.584 | -0.973 | -0.558 |
| 1 | 0.026 | -0.048 | -0.880 | -0.406 |
| 1 | 0.112 | -0.466 | -0.980 | -0.447 |
| 1 | 1.710 | -0.561 | -0.755 | -0.408 |
| 1 | 1.630 | -0.918 | -1.230 | -0.470 |
| 1 | 0.624 | -0.490 | -0.944 | -0.599 |
| 1 | 0.051 | -0.922 | -0.990 | -0.450 |
| 1 | 0.197 | -0.004 | -0.908 | -0.510 |
| 1 | -0.814 | -0.239 | -0.815 | -0.289 |
| 1 | -1.510 | -0.399 | -0.932 | -0.328 |
| 1 | 0.403 | -0.161 | -1.000 | -0.616 |
| 1 | 0.043 | -0.967 | -0.972 | -0.665 |
| 1 | -1.940 | -1.510 | -0.728 | -0.651 |
| 1 | -0.980 | -0.603 | -0.988 | -0.440 |
| 1 | 0.468 | -0.327 | -0.855 | -0.442 |
| 1 | 0.174 | -1.140 | -0.843 | -0.627 |
| 1 | 1.220 | -0.413 | -0.873 | -0.518 |
| 1 | 1.110 | -0.272 | -0.801 | -0.410 |
| 1 | 0.096 | -0.299 | -0.956 | -0.524 |
| 1 | -1.190 | -0.083 | -0.928 | -0.501 |
| 2 | -0.642 | -0.115 | -0.891 | -0.659 |
| 2 | -0.421 | -0.074 | -0.746 | -0.336 |
| 2 | -0.170 | -0.293 | -0.999 | -0.479 |
| 2 | -1.680 | -1.210 | -0.052 | -0.787 |

| | | | | |
|---|---|---|---|---|
| 2 | -0.828 | -0.215 | -0.730 | -0.495 |
| 2 | -0.327 | -0.096 | -0.893 | -0.541 |
| 2 | -1.690 | -0.350 | -1.570 | 0.044 |
| 2 | -1.330 | -0.709 | -0.869 | -0.413 |
| 2 | -0.481 | 0.261 | -0.864 | -0.420 |
| 2 | -0.623 | -0.126 | -0.913 | -0.550 |
| 2 | 0.035 | -0.325 | -0.990 | -0.496 |
| 2 | -0.809 | -0.255 | -0.765 | -0.478 |
| 2 | -0.764 | -0.153 | -0.959 | -0.573 |
| 3 | -1.850 | -1.730 | -1.060 | -1.300 |
| 3 | -0.299 | -0.487 | -0.796 | -0.542 |
| 3 | -0.205 | -0.496 | -0.880 | -0.481 |
| 3 | 1.990 | -1.760 | -0.752 | -0.609 |
| 3 | -0.612 | -0.292 | -1.150 | -0.562 |
| 3 | -1.110 | -1.070 | -0.996 | -0.604 |
| 3 | -1.300 | -0.330 | -1.240 | -0.852 |
| 3 | -0.176 | -0.114 | -0.995 | -0.616 |
| 3 | -1.460 | -0.228 | -1.110 | -0.520 |
| 3 | -0.435 | -0.881 | -1.090 | -0.533 |
| 4 | -0.286 | -0.057 | -0.928 | -0.711 |
| 4 | -1.080 | -0.546 | -0.964 | -0.488 |
| 4 | -1.140 | -0.573 | -1.030 | -0.261 |
| 4 | -0.649 | -0.848 | -1.060 | -0.411 |
| 4 | -1.770 | -1.110 | -0.822 | -0.476 |
| 4 | -1.140 | -0.881 | -0.894 | -0.408 |
| 4 | 1.940 | -1.980 | -0.856 | -0.521 |
| 4 | -0.839 | -0.500 | -0.955 | -0.571 |
| 4 | -1.550 | -0.608 | -1.180 | -0.232 |
| 4 | -0.263 | -0.158 | -0.744 | -0.297 |
| 4 | 1.590 | -0.250 | -0.869 | -0.474 |
| 4 | -1.030 | -0.353 | -0.739 | -0.284 |
| 4 | -1.420 | -0.641 | -1.030 | -0.377 |
| 4 | -0.864 | -0.313 | -1.090 | -0.495 |
| 4 | -0.095 | -0.982 | -1.050 | -0.451 |
| 5 | 0.415 | -0.346 | -0.649 | -0.850 |
| 5 | -1.320 | -0.560 | -0.940 | -0.282 |
| 5 | 0.716 | -0.066 | -0.872 | -0.464 |
| 5 | -1.010 | -0.403 | -1.070 | -0.492 |
| 5 | -0.057 | -1.040 | -1.090 | -0.594 |
| 5 | 0.067 | -0.471 | -1.020 | -0.277 |
| 5 | 0.702 | -1.080 | -1.610 | -0.545 |
| 5 | 0.297 | -0.568 | -1.020 | -0.626 |
| 5 | -0.403 | -0.508 | -0.966 | -0.386 |
| 5 | 1.060 | -1.030 | -1.030 | -0.227 |
| 5 | -0.971 | -0.624 | -0.731 | -0.284 |
| 5 | -1.300 | -0.254 | -1.590 | -0.970 |
| 5 | -1.200 | -0.041 | -1.020 | -0.759 |
| 5 | -0.276 | 0.347 | -0.762 | -0.781 |
| 5 | 0.183 | -0.273 | -0.794 | -0.676 |
| 5 | -0.616 | -0.661 | -0.989 | -0.818 |
| 5 | -0.318 | -0.323 | -1.130 | -0.570 |

| | | | | |
|---|---|---|---|---|
| 5 | -0.406 | -0.773 | -0.981 | -0.286 |
| 5 | -0.451 | -0.297 | -1.050 | -0.430 |
| 5 | 0.557 | -0.088 | -0.927 | -0.665 |
| 5 | -0.208 | -0.863 | -0.967 | -0.484 |
| 5 | -0.258 | 0.027 | -0.908 | -0.372 |
| 5 | -0.400 | -0.813 | -0.967 | -0.583 |
| 6 | -0.382 | -1.460 | -0.829 | -0.076 |
| 6 | -1.370 | -0.247 | -0.950 | -0.132 |
| 6 | -0.616 | -0.256 | -0.867 | -0.432 |
| 6 | 0.390 | -0.182 | -0.796 | -0.355 |
| 6 | -0.546 | -0.424 | -1.200 | -0.654 |
| 6 | 0.768 | -1.170 | -1.140 | -0.381 |
| 6 | -0.770 | -0.906 | -0.862 | -0.358 |
| 6 | -1.810 | -0.883 | -1.110 | -0.225 |
| 6 | 0.026 | -1.210 | -0.959 | -0.584 |
| 6 | -1.060 | -0.393 | -0.945 | -0.578 |
| 6 | -1.370 | -0.783 | -0.837 | -0.544 |
| 6 | 0.880 | -0.476 | -0.936 | -0.372 |
| 6 | -0.589 | -0.346 | -1.040 | -0.451 |
| 6 | 0.662 | -1.040 | -0.993 | -0.515 |
| 6 | -0.292 | -0.048 | -0.985 | -0.457 |
| 6 | -0.106 | -0.239 | -0.796 | -0.440 |
| 6 | -1.020 | -0.816 | -0.936 | -0.213 |
| 6 | -0.484 | -0.425 | -0.757 | -0.417 |
| 6 | -0.834 | -0.521 | -1.000 | -0.586 |
| 6 | -1.340 | -1.860 | -0.571 | -0.439 |
| 6 | -0.084 | -0.197 | -1.010 | -0.541 |
| 6 | -0.733 | -0.689 | -1.050 | -0.421 |
| 6 | -0.788 | -0.409 | -0.958 | -0.358 |
| 6 | -1.280 | -1.410 | -1.210 | -0.353 |
| 6 | -0.816 | -0.099 | -0.780 | -0.370 |
| 6 | -1.160 | -1.060 | -1.060 | -0.531 |
| 6 | -0.434 | -0.092 | -0.785 | -0.477 |
| 6 | -0.139 | -1.300 | -0.827 | -0.555 |
| 6 | -0.768 | 0.120 | -0.628 | -0.568 |
| 6 | -0.951 | -0.441 | -1.110 | -0.085 |
| 6 | -0.392 | -0.307 | -0.411 | -0.213 |
| 6 | -0.015 | 0.071 | -0.829 | -0.420 |
| 6 | -1.430 | -0.619 | -1.150 | -0.767 |
| 6 | -1.110 | -1.070 | -0.843 | -0.648 |
| 6 | -1.360 | -0.504 | -0.251 | -0.591 |
| | -1.940 | -1.980 | -1.610 | -1.300 |

Principal Components of Reduced-Parameter Constituent Algorithm 1 which differentiates SILs from Normal Squamous Tissues. Results reported for calibration set.

| L | PC1 | PC2 | PC3 | PC4 | PC6 |
|---|---|---|---|---|---|
| 1 | 0.748 | -1.370 | 0.432 | -0.128 | -0.580 |
| 1 | 0.747 | -1.380 | 0.432 | -0.128 | -0.602 |
| 1 | 0.857 | -1.490 | 0.644 | -0.281 | -0.410 |
| 1 | 0.937 | -1.410 | 0.678 | -0.111 | -0.615 |
| 1 | 0.513 | -1.310 | 0.791 | -0.172 | -0.572 |
| 1 | 0.150 | -1.190 | 0.803 | -0.165 | -0.552 |
| 1 | 0.828 | -1.280 | 0.772 | -0.179 | -0.553 |
| 1 | 0.768 | -1.370 | 0.870 | -0.187 | -0.568 |
| 1 | 0.334 | -1.350 | 0.819 | -0.183 | -0.606 |
| 1 | 0.929 | -1.340 | 0.657 | -0.183 | -0.589 |
| 1 | 0.989 | -1.300 | 0.676 | -0.143 | -0.577 |
| 1 | 0.584 | -1.320 | 0.789 | -0.170 | -0.590 |
| 1 | 0.807 | -1.300 | 0.716 | -0.165 | -0.584 |
| 1 | -0.221 | -1.050 | 0.509 | -0.117 | -0.515 |
| 1 | 0.729 | -1.360 | 0.699 | -0.146 | -0.575 |
| 1 | 0.969 | -1.320 | 0.646 | -0.158 | -0.575 |
| 1 | 0.701 | -1.450 | 0.734 | -0.056 | -0.563 |
| 1 | 0.773 | -1.490 | 0.722 | -0.071 | -0.577 |
| 1 | 0.878 | -1.270 | 0.697 | -0.173 | -0.622 |
| 1 | 0.766 | -1.120 | 0.535 | -0.141 | -0.550 |
| 1 | 0.645 | -1.370 | 0.690 | -0.125 | -0.534 |
| 1 | 0.741 | -0.828 | 0.386 | -0.060 | -0.589 |
| 1 | 0.972 | -1.270 | 0.761 | -0.146 | -0.541 |
| 1 | 0.680 | -1.260 | 0.774 | -0.179 | -0.578 |
| 1 | 0.993 | -1.100 | 0.718 | -0.213 | -0.566 |
| 1 | 0.848 | -1.340 | 0.819 | -0.130 | -0.508 |
| 1 | 0.316 | -1.180 | 0.794 | -0.125 | -0.533 |
| 1 | 0.579 | -1.310 | 0.730 | -0.077 | -0.535 |
| 1 | 0.738 | -1.250 | 0.851 | -0.083 | -0.509 |
| 1 | 0.303 | -1.370 | 0.816 | 0.046 | -0.575 |
| 1 | 0.862 | -1.290 | 0.736 | -0.124 | -0.524 |
| 1 | 0.975 | -1.140 | 0.635 | -0.116 | -0.564 |
| 1 | 0.935 | -1.330 | 0.763 | -0.065 | -0.530 |
| 1 | 0.897 | -1.270 | 0.703 | -0.111 | -0.528 |
| 1 | 0.697 | -1.380 | 0.821 | -0.085 | -0.551 |
| 1 | 0.789 | -1.300 | 0.724 | -0.075 | -0.523 |
| 1 | 0.701 | -1.320 | 0.700 | -0.073 | -0.536 |
| 1 | 0.676 | -1.340 | 0.765 | -0.110 | -0.541 |
| 1 | 0.433 | -1.540 | 0.666 | 0.109 | -0.541 |
| 1 | 0.910 | -1.340 | 0.776 | -0.315 | -0.621 |
| 1 | 0.557 | -1.370 | 0.781 | -0.099 | -0.481 |
| 1 | 0.923 | -1.300 | 0.873 | -0.105 | -0.514 |
| 1 | 0.628 | -1.210 | 0.845 | -0.101 | -0.473 |
| 1 | 1.060 | -1.170 | 0.705 | -0.141 | -0.543 |
| 1 | 0.897 | -1.140 | 0.598 | -0.167 | -0.600 |
| 1 | 0.143 | -1.310 | 0.845 | -0.269 | -0.687 |

| | | | | | |
|---|---|---|---|---|---|
| 1 | 0.635 | -1.310 | 0.807 | -0.185 | -0.568 |
| 1 | 0.867 | -1.360 | 0.763 | -0.069 | -0.531 |
| 1 | 0.771 | -1.250 | 0.769 | -0.051 | -0.472 |
| 1 | 0.763 | -1.330 | 0.681 | -0.114 | -0.552 |
| 1 | 1.060 | -1.170 | 0.697 | -0.135 | -0.522 |
| 1 | 1.040 | -1.330 | 0.754 | -0.143 | -0.568 |
| 1 | 0.898 | -1.430 | 0.724 | -0.096 | -0.574 |
| 1 | 0.558 | -1.330 | 0.789 | -0.059 | -0.487 |
| 1 | 0.668 | -1.340 | 0.771 | -0.192 | -0.536 |
| 1 | 0.582 | -1.320 | 0.713 | 0.020 | -0.537 |
| 1 | 0.771 | -1.440 | 0.656 | -0.164 | -0.597 |
| 1 | 0.635 | -1.280 | 0.691 | -0.059 | -0.559 |
| 1 | 0.854 | -1.400 | 0.686 | -0.126 | -0.585 |
| 1 | 0.876 | -1.360 | 0.640 | -0.142 | -0.599 |
| 1 | 0.679 | -1.260 | 0.784 | 0.006 | -0.511 |
| 1 | 0.690 | -1.320 | 0.834 | -0.146 | -0.491 |
| 1 | 0.711 | -1.340 | 0.753 | -0.096 | -0.524 |
| 1 | 0.694 | -1.300 | 0.677 | -0.099 | -0.546 |
| 1 | 0.812 | -1.160 | 0.545 | -0.188 | -0.640 |
| 1 | 0.671 | -1.390 | 0.754 | -0.054 | -0.556 |
| 1 | 0.869 | -1.300 | 0.844 | -0.337 | -0.660 |
| 1 | 1.000 | -1.300 | 0.724 | -0.160 | -0.568 |
| 1 | 0.860 | -1.350 | 0.693 | -0.166 | -0.576 |
| 1 | 0.476 | -1.340 | 0.738 | 0.152 | -0.500 |
| 1 | 0.804 | -1.500 | 0.728 | -0.141 | -0.576 |
| 1 | 0.729 | -1.330 | 0.790 | -0.069 | -0.509 |
| 1 | 0.167 | -1.360 | 0.671 | -0.096 | -0.558 |
| 1 | 0.929 | -1.330 | 0.733 | -0.087 | -0.542 |
| 1 | 0.933 | -1.110 | 0.651 | -0.113 | -0.562 |
| 1 | 0.581 | -1.270 | 0.710 | -0.182 | -0.577 |
| 1 | 0.655 | -1.370 | 0.765 | -0.077 | -0.570 |
| 1 | 0.921 | -1.070 | 0.652 | -0.187 | -0.548 |
| 1 | 0.753 | -1.010 | 0.620 | -0.111 | -0.522 |
| 1 | 0.730 | -1.320 | 0.687 | -0.124 | -0.546 |
| 1 | 0.615 | -1.430 | 0.692 | -0.014 | -0.552 |
| 1 | 0.640 | -1.150 | 0.655 | -0.012 | -0.445 |
| 1 | 0.155 | -1.200 | 0.583 | -0.225 | -0.573 |
| 1 | -0.120 | -1.140 | 0.592 | -0.191 | -0.573 |
| 1 | 0.694 | -1.280 | 0.727 | -0.123 | -0.544 |
| 1 | 0.556 | -1.460 | 0.645 | -0.043 | -0.506 |
| 1 | -0.245 | -1.390 | 0.594 | -0.170 | -0.560 |
| 1 | 0.126 | -1.310 | 0.639 | -0.083 | -0.486 |
| 1 | 0.726 | -1.330 | 0.668 | -0.131 | -0.559 |
| 1 | 0.633 | -1.490 | 0.669 | -0.076 | -0.568 |
| 1 | 0.879 | -1.260 | 0.732 | -0.224 | -0.559 |
| 1 | 0.898 | -1.260 | 0.606 | -0.183 | -0.567 |
| 1 | 0.641 | -1.290 | 0.788 | -0.113 | -0.552 |
| 1 | -0.132 | -0.941 | 0.564 | -0.168 | -0.439 |
| 2 | 0.407 | -1.260 | 0.803 | -0.116 | -0.546 |
| 2 | 0.494 | -1.260 | 0.841 | -0.228 | -0.586 |
| 2 | 0.474 | -1.350 | 0.762 | -0.273 | -0.653 |

| | | | | | |
|---|---|---|---|---|---|
| 2 | 0.009 | -1.650 | 0.734 | -0.455 | -0.352 |
| 2 | 0.254 | -1.280 | 0.903 | -0.364 | -0.616 |
| 2 | 0.496 | -1.250 | 0.868 | -0.143 | -0.534 |
| 2 | -0.170 | -1.120 | 0.642 | 0.053 | -0.728 |
| 2 | 0.179 | -1.460 | 0.977 | -0.370 | -0.650 |
| 2 | 0.490 | -1.170 | 0.905 | -0.200 | -0.513 |
| 2 | 0.383 | -1.240 | 0.739 | -0.193 | -0.555 |
| 2 | 0.585 | -1.320 | 0.819 | -0.163 | -0.569 |
| 2 | 0.376 | -1.310 | 0.890 | -0.186 | -0.557 |
| 2 | 0.403 | -1.230 | 0.785 | -0.018 | -0.471 |
| 3 | -0.201 | -1.510 | 0.489 | -0.004 | -0.466 |
| 3 | 0.590 | -1.380 | 0.739 | -0.071 | -0.536 |
| 3 | 0.593 | -1.380 | 0.751 | -0.082 | -0.539 |
| 3 | 0.658 | -0.962 | 0.373 | -0.144 | -0.665 |
| 3 | 0.520 | -1.370 | 0.890 | -0.003 | -0.508 |
| 3 | 0.279 | -1.550 | 0.839 | -0.186 | -0.608 |
| 3 | -0.062 | -1.080 | 0.662 | -0.004 | -0.488 |
| 3 | 0.657 | -1.310 | 0.849 | -0.085 | -0.530 |
| 3 | -0.090 | -1.100 | 0.788 | -0.163 | -0.527 |
| 3 | 0.533 | -1.490 | 0.769 | 0.040 | -0.530 |
| 4 | 0.549 | -1.290 | 0.801 | -0.188 | -0.538 |
| 4 | 0.270 | -1.390 | 0.864 | -0.182 | -0.633 |
| 4 | 0.241 | -1.450 | 0.882 | -0.166 | -0.635 |
| 4 | 0.455 | -1.470 | 0.764 | -0.005 | -0.613 |
| 4 | -0.119 | -1.380 | 0.636 | -0.180 | -0.601 |
| 4 | 0.162 | -1.460 | 0.753 | -0.179 | -0.605 |
| 4 | 0.610 | -1.010 | 0.285 | -0.158 | -0.690 |
| 4 | 0.394 | -1.360 | 0.826 | -0.039 | -0.551 |
| 4 | -0.007 | -1.290 | 0.706 | 0.034 | -0.564 |
| 4 | 0.494 | -1.260 | 0.818 | -0.195 | -0.556 |
| 4 | 0.999 | -1.150 | 0.673 | -0.154 | -0.518 |
| 4 | 0.243 | -1.310 | 0.784 | -0.140 | -0.667 |
| 4 | 0.102 | -1.290 | 0.656 | 0.177 | -0.501 |
| 4 | 0.176 | -1.190 | 0.687 | -0.058 | -0.504 |
| 4 | 0.444 | -1.430 | 0.540 | -0.059 | -0.606 |
| 5 | 0.731 | -1.380 | 0.721 | -0.247 | -0.437 |
| 5 | 0.004 | -1.260 | 0.744 | -0.204 | -0.625 |
| 5 | 0.864 | -1.330 | 0.667 | -0.177 | -0.579 |
| 5 | -0.023 | -1.140 | 0.653 | -0.274 | -0.600 |
| 5 | 0.671 | -1.540 | 0.729 | 0.059 | -0.539 |
| 5 | 0.622 | -1.400 | 0.823 | -0.079 | -0.534 |
| 5 | 0.495 | -1.230 | 0.677 | -0.069 | -0.513 |
| 5 | 0.759 | -1.440 | 0.780 | -0.097 | -0.608 |
| 5 | 0.581 | -1.450 | 0.835 | -0.080 | -0.588 |
| 5 | 0.782 | -1.360 | 0.539 | -0.088 | -0.662 |
| 5 | 0.242 | -1.380 | 0.812 | -0.253 | -0.647 |
| 5 | -0.019 | -1.210 | 0.932 | -0.074 | -0.532 |
| 5 | 0.194 | -1.230 | 0.990 | -0.170 | -0.529 |
| 5 | 0.682 | -1.160 | 1.080 | -0.110 | -0.391 |
| 5 | 0.750 | -1.330 | 0.848 | -0.108 | -0.485 |
| 5 | 0.274 | -1.370 | 0.748 | -0.135 | -0.538 |

| | | | | | |
|---|---|---|---|---|---|
| 5 | 0.510 | -1.360 | 0.785 | -0.090 | -0.560 |
| 5 | 0.533 | -1.440 | 0.781 | -0.053 | -0.590 |
| 5 | 0.468 | -1.350 | 0.903 | -0.216 | -0.532 |
| 5 | 0.747 | -1.160 | 0.733 | 0.027 | -0.441 |
| 5 | 0.593 | -1.450 | 0.746 | 0.072 | -0.555 |
| 5 | 0.570 | -1.230 | 0.841 | -0.065 | -0.504 |
| 5 | 0.451 | -1.430 | 0.709 | -0.052 | -0.607 |
| 6 | 0.499 | -1.670 | 0.458 | 0.002 | -0.634 |
| 6 | 0.015 | -1.220 | 0.779 | -0.226 | -0.605 |
| 6 | 0.427 | -1.310 | 0.809 | -0.164 | -0.589 |
| 6 | 0.760 | -1.390 | 0.745 | -0.267 | -0.633 |
| 6 | 0.262 | -1.270 | 0.734 | -0.141 | -0.603 |
| 6 | 0.825 | -1.540 | 0.724 | -0.006 | -0.617 |
| 6 | 0.389 | -1.470 | 0.767 | -0.072 | -0.623 |
| 6 | -0.249 | -1.250 | 0.494 | -0.049 | -0.592 |
| 6 | 0.698 | -1.590 | 0.770 | 0.038 | -0.580 |
| 6 | 0.255 | -1.360 | 0.910 | -0.258 | -0.648 |
| 6 | 0.178 | -1.460 | 0.854 | -0.178 | -0.598 |
| 6 | 0.857 | -1.340 | 0.784 | -0.122 | -0.570 |
| 6 | 0.402 | -1.320 | 0.813 | -0.063 | -0.534 |
| 6 | 0.677 | -1.460 | 0.632 | -0.088 | -0.583 |
| 6 | 0.485 | -1.190 | 0.900 | -0.112 | -0.512 |
| 6 | 0.610 | -1.260 | 0.765 | -0.104 | -0.553 |
| 6 | 0.271 | -1.440 | 0.752 | -0.104 | -0.621 |
| 6 | 0.498 | -1.390 | 0.801 | -0.156 | -0.573 |
| 6 | 0.405 | -1.380 | 0.790 | 0.034 | -0.527 |
| 6 | 0.165 | -1.830 | 0.499 | -0.127 | -0.531 |
| 6 | 0.582 | -1.320 | 0.755 | -0.166 | -0.580 |
| 6 | 0.352 | -1.410 | 0.689 | -0.041 | -0.538 |
| 6 | 0.413 | -1.340 | 0.805 | -0.068 | -0.574 |
| 6 | 0.065 | -1.510 | 0.689 | 0.089 | -0.554 |
| 6 | 0.364 | -1.240 | 0.845 | -0.212 | -0.586 |
| 6 | 0.261 | -1.440 | 0.720 | 0.055 | -0.573 |
| 6 | 0.538 | -1.270 | 0.802 | -0.074 | -0.507 |
| 6 | 0.526 | -1.580 | 0.615 | -0.049 | -0.606 |
| 6 | 0.397 | -1.150 | 0.778 | 0.019 | -0.473 |
| 6 | 0.292 | -1.310 | 0.758 | 0.000 | -0.584 |
| 6 | 0.433 | -1.370 | 0.797 | -0.322 | -0.716 |
| 6 | 0.635 | -1.190 | 0.803 | -0.116 | -0.483 |
| 6 | -0.064 | -1.230 | 0.813 | -0.203 | -0.636 |
| 6 | 0.254 | -1.530 | 0.733 | -0.091 | -0.587 |
| 6 | 0.037 | -1.230 | 0.671 | -0.260 | -0.454 |

5

Principal Components of Reduced-Parameter Constituent Algorithm 2 which differentiates SILs from Normal Columnar Tissues. Results reported for calibration set:

| L | PC1 | PC2 | PC5 |
|---|---|---|---|
| 1 | 0.118 | 0.022 | 0.021 |
| 1 | 0.238 | 0.021 | -0.035 |
| 1 | 0.190 | -0.095 | 0.056 |
| 1 | 0.275 | -0.114 | 0.013 |
| 1 | 0.195 | -0.053 | 0.002 |
| 1 | -0.127 | 0.084 | 0.008 |
| 1 | 0.222 | 0.044 | 0.000 |
| 1 | 0.003 | 0.056 | -0.018 |
| 1 | -0.429 | 0.065 | 0.027 |
| 1 | 0.088 | 0.007 | -0.042 |
| 1 | 0.146 | 0.031 | 0.032 |
| 1 | -0.017 | -0.012 | -0.005 |
| 1 | 0.174 | -0.022 | -0.028 |
| 1 | -0.542 | 0.127 | 0.036 |
| 1 | -0.044 | 0.029 | 0.007 |
| 1 | 0.249 | -0.052 | -0.006 |
| 1 | 0.007 | -0.005 | -0.016 |
| 1 | 0.079 | -0.046 | -0.015 |
| 1 | 0.267 | 0.051 | 0.074 |
| 1 | 0.247 | -0.009 | 0.039 |
| 1 | 0.248 | -0.052 | -0.085 |
| 1 | 0.083 | 0.050 | -0.048 |
| 1 | 0.340 | -0.073 | 0.011 |
| 1 | 0.342 | 0.089 | 0.057 |
| 1 | 0.463 | 0.124 | 0.095 |
| 1 | 0.166 | -0.026 | 0.027 |
| 1 | -0.170 | 0.089 | 0.018 |
| 1 | 0.155 | -0.058 | -0.047 |
| 1 | 0.079 | 0.084 | -0.009 |
| 1 | -0.370 | -0.067 | 0.062 |
| 1 | 0.272 | 0.012 | -0.021 |
| 1 | 0.110 | 0.177 | 0.131 |
| 1 | 0.060 | 0.062 | -0.019 |
| 1 | 0.280 | 0.087 | 0.026 |
| 1 | 0.268 | -0.086 | -0.002 |
| 1 | 0.239 | -0.068 | -0.024 |
| 1 | 0.151 | -0.084 | -0.042 |
| 1 | 0.186 | -0.063 | -0.034 |
| 1 | -0.004 | -0.200 | 0.026 |
| 1 | 0.353 | 0.058 | 0.026 |
| 1 | 0.087 | -0.044 | 0.019 |
| 1 | 0.179 | -0.028 | 0.005 |
| 1 | 0.092 | 0.130 | -0.046 |
| 1 | 0.390 | 0.011 | 0.028 |
| 1 | 0.334 | 0.147 | 0.086 |

| | | | |
|---|---|---|---|
| 1 | -0.201 | -0.065 | 0.108 |
| 1 | 0.098 | 0.024 | -0.007 |
| 1 | 0.249 | -0.036 | -0.036 |
| 1 | 0.123 | 0.008 | -0.024 |
| 1 | 0.425 | 0.087 | -0.039 |
| 1 | 0.277 | -0.047 | 0.043 |
| 1 | 0.172 | 0.061 | 0.032 |
| 1 | 0.237 | -0.106 | -0.018 |
| 1 | 0.077 | -0.071 | -0.037 |
| 1 | 0.396 | 0.027 | -0.057 |
| 1 | 0.146 | -0.042 | -0.037 |
| 1 | 0.025 | -0.034 | -0.002 |
| 1 | 0.029 | 0.016 | 0.025 |
| 1 | 0.239 | -0.038 | -0.004 |
| 1 | 0.449 | -0.020 | -0.026 |
| 1 | 0.243 | 0.026 | -0.016 |
| 1 | 0.187 | 0.024 | -0.015 |
| 1 | 0.243 | 0.002 | -0.015 |
| 1 | 0.261 | -0.106 | -0.007 |
| 1 | 0.149 | 0.042 | -0.006 |
| 1 | 0.209 | 0.071 | 0.000 |
| 1 | 0.363 | 0.059 | 0.063 |
| 1 | 0.346 | -0.066 | 0.022 |
| 1 | 0.257 | 0.043 | 0.004 |
| 1 | 0.013 | -0.115 | 0.011 |
| 1 | 0.092 | -0.062 | 0.014 |
| 1 | 0.184 | 0.042 | -0.029 |
| 1 | -0.373 | 0.015 | -0.060 |
| 1 | 0.164 | -0.035 | -0.018 |
| 1 | 0.207 | 0.125 | 0.111 |
| 1 | 0.114 | 0.006 | -0.034 |
| 1 | 0.081 | -0.019 | -0.004 |
| 1 | 0.284 | 0.057 | 0.120 |
| 1 | 0.240 | 0.125 | 0.079 |
| 1 | 0.175 | 0.140 | 0.039 |
| 1 | 0.086 | -0.106 | 0.021 |
| 1 | 0.171 | -0.018 | 0.027 |
| 1 | -0.129 | 0.000 | -0.033 |
| 1 | -0.405 | 0.057 | 0.038 |
| 1 | 0.116 | 0.117 | -0.099 |
| 1 | 0.046 | -0.147 | -0.003 |
| 1 | 0.064 | -0.058 | 0.068 |
| 1 | 0.081 | -0.045 | -0.014 |
| 1 | 0.025 | 0.025 | -0.059 |
| 1 | 0.015 | -0.203 | 0.040 |
| 1 | 0.158 | 0.074 | -0.079 |
| 1 | 0.229 | 0.079 | 0.011 |
| 1 | 0.146 | 0.032 | -0.029 |
| 1 | -0.110 | 0.113 | -0.017 |
| 2 | -0.243 | 0.099 | -0.029 |
| 2 | -0.111 | 0.109 | 0.025 |

| | | | |
|---|---|---|---|
| 2 | -0.304 | 0.052 | 0.062 |
| 2 | -0.388 | -0.008 | 0.038 |
| 2 | -0.134 | 0.168 | 0.031 |
| 2 | -0.044 | 0.049 | -0.038 |
| 2 | -0.412 | 0.076 | 0.010 |
| 2 | -0.389 | 0.069 | 0.008 |
| 2 | -0.242 | 0.152 | -0.002 |
| 2 | -0.258 | 0.059 | 0.013 |
| 2 | -0.074 | -0.025 | 0.009 |
| 2 | -0.388 | 0.079 | 0.004 |
| 2 | -0.248 | -0.046 | -0.042 |
| 3 | -0.231 | -0.054 | 0.051 |
| 3 | -0.099 | 0.063 | 0.031 |
| 3 | -0.026 | -0.027 | -0.041 |
| 3 | -0.007 | -0.058 | -0.025 |
| 3 | 0.013 | -0.095 | 0.008 |
| 3 | -0.297 | -0.118 | 0.056 |
| 3 | -0.660 | 0.204 | 0.066 |
| 3 | 0.003 | 0.065 | -0.010 |
| 3 | -0.696 | 0.166 | 0.012 |
| 3 | -0.027 | -0.141 | 0.058 |
| 4 | -0.108 | 0.129 | -0.005 |
| 4 | -0.021 | -0.098 | 0.026 |
| 4 | -0.376 | -0.046 | -0.024 |
| 4 | -0.176 | -0.140 | 0.012 |
| 4 | -0.517 | -0.055 | 0.028 |
| 4 | -0.241 | -0.087 | -0.031 |
| 4 | -0.057 | -0.129 | -0.003 |
| 4 | -0.158 | -0.096 | 0.019 |
| 4 | -0.260 | -0.036 | -0.052 |
| 4 | 0.031 | 0.075 | -0.007 |
| 4 | 0.224 | -0.024 | 0.027 |
| 4 | -0.187 | 0.032 | 0.049 |
| 4 | -0.356 | -0.083 | -0.054 |
| 4 | 0.131 | 0.052 | -0.016 |
| 4 | -0.260 | -0.123 | 0.010 |
| 5 | 0.071 | 0.037 | -0.041 |
| 5 | -0.311 | 0.000 | 0.043 |
| 5 | 0.086 | 0.008 | 0.030 |
| 5 | -0.536 | 0.088 | 0.012 |
| 5 | -0.223 | -0.170 | -0.050 |
| 5 | -0.126 | 0.049 | -0.037 |
| 5 | -0.031 | -0.035 | -0.072 |
| 5 | 0.098 | -0.098 | 0.074 |
| 5 | -0.042 | -0.110 | 0.013 |
| 5 | -0.068 | -0.098 | 0.127 |
| 5 | -0.178 | 0.116 | 0.065 |
| 5 | -0.439 | 0.122 | -0.028 |
| 5 | -0.224 | 0.156 | 0.001 |
| 5 | -0.106 | 0.111 | -0.024 |
| 5 | -0.115 | 0.111 | -0.033 |

| | | | |
|---|---|---|---|
| 5 | -0.002 | -0.006 | -0.061 |
| 5 | -0.107 | 0.033 | 0.003 |
| 5 | 0.094 | -0.065 | 0.033 |
| 5 | -0.038 | 0.052 | -0.144 |
| 5 | 0.300 | 0.072 | -0.012 |
| 5 | -0.122 | -0.060 | -0.001 |
| 5 | 0.092 | -0.012 | -0.002 |
| 5 | -0.145 | -0.052 | 0.026 |
| 6 | -0.157 | -0.274 | -0.011 |
| 6 | -0.295 | 0.073 | -0.065 |
| 6 | -0.173 | 0.017 | 0.006 |
| 6 | -0.021 | -0.002 | 0.017 |
| 6 | -0.157 | -0.009 | 0.046 |
| 6 | -0.066 | -0.166 | -0.028 |
| 6 | -0.165 | -0.151 | 0.059 |
| 6 | -0.581 | 0.115 | 0.014 |
| 6 | -0.190 | -0.212 | -0.011 |
| 6 | -0.226 | -0.014 | 0.047 |
| 6 | -0.259 | -0.011 | 0.013 |
| 6 | 0.092 | -0.019 | 0.013 |
| 6 | -0.079 | -0.032 | -0.007 |
| 6 | 0.112 | -0.015 | 0.036 |
| 6 | -0.116 | 0.187 | -0.076 |
| 6 | 0.117 | 0.048 | -0.009 |
| 6 | -0.028 | -0.079 | 0.007 |
| 6 | 0.075 | 0.072 | 0.009 |
| 6 | -0.197 | -0.081 | 0.022 |
| 6 | -0.477 | -0.439 | -0.113 |
| 6 | 0.097 | -0.037 | -0.012 |
| 6 | -0.157 | -0.019 | -0.019 |
| 6 | -0.133 | -0.010 | 0.015 |
| 6 | -0.525 | -0.174 | -0.121 |
| 6 | 0.025 | -0.008 | 0.011 |
| 6 | -0.100 | -0.314 | 0.069 |
| 6 | -0.003 | 0.034 | -0.007 |
| 6 | 0.137 | -0.049 | -0.018 |
| 6 | -0.024 | 0.142 | -0.038 |
| 6 | -0.143 | -0.011 | -0.045 |
| 6 | -0.232 | 0.011 | -0.195 |
| 6 | -0.007 | 0.023 | -0.085 |
| 6 | -0.110 | 0.073 | 0.136 |
| 6 | -0.137 | 0.049 | 0.018 |
| 6 | 0.035 | -0.101 | -0.044 |

5

Principal Components of Reduced-Parameter Constituent Algorithm 3 which differentiates HG SILs from LG SILs. Results reported for calibration set:

| L | PC1 | PC3 | PC4 | PC7 | PC8 |
|---|---|---|---|---|---|
| 1 | 0.748 | 0.432 | -0.128 | -0.304 | 0.052 |
| 1 | 0.747 | 0.432 | -0.128 | -0.281 | 0.032 |
| 1 | 0.857 | 0.644 | -0.281 | -0.223 | -0.014 |
| 1 | 0.937 | 0.678 | -0.111 | -0.172 | 0.008 |
| 1 | 0.513 | 0.791 | -0.172 | -0.254 | 0.075 |
| 1 | 0.150 | 0.803 | -0.165 | -0.271 | 0.013 |
| 1 | 0.828 | 0.772 | -0.179 | -0.232 | 0.077 |
| 1 | 0.768 | 0.870 | -0.187 | -0.229 | 0.074 |
| 1 | 0.334 | 0.819 | -0.183 | -0.214 | 0.086 |
| 1 | 0.929 | 0.657 | -0.183 | -0.175 | 0.017 |
| 1 | 0.989 | 0.676 | -0.143 | -0.192 | 0.039 |
| 1 | 0.584 | 0.789 | -0.170 | -0.191 | 0.032 |
| 1 | 0.807 | 0.716 | -0.165 | -0.186 | 0.061 |
| 1 | -0.221 | 0.509 | -0.117 | -0.193 | 0.006 |
| 1 | 0.729 | 0.699 | -0.146 | -0.164 | -0.011 |
| 1 | 0.969 | 0.646 | -0.158 | -0.243 | 0.051 |
| 1 | 0.701 | 0.734 | -0.056 | -0.198 | 0.045 |
| 1 | 0.773 | 0.722 | -0.071 | -0.173 | 0.048 |
| 1 | 0.878 | 0.697 | -0.173 | -0.207 | 0.061 |
| 1 | 0.766 | 0.535 | -0.141 | -0.252 | 0.031 |
| 1 | 0.645 | 0.690 | -0.125 | -0.159 | 0.030 |
| 1 | 0.741 | 0.386 | -0.060 | -0.187 | 0.026 |
| 1 | 0.972 | 0.761 | -0.146 | -0.177 | 0.032 |
| 1 | 0.680 | 0.774 | -0.179 | -0.173 | -0.008 |
| 1 | 0.993 | 0.718 | -0.213 | -0.176 | 0.021 |
| 1 | 0.848 | 0.819 | -0.130 | -0.191 | 0.019 |
| 1 | 0.316 | 0.794 | -0.125 | -0.281 | 0.117 |
| 1 | 0.579 | 0.730 | -0.077 | -0.253 | 0.043 |
| 1 | 0.738 | 0.851 | -0.083 | -0.222 | 0.022 |
| 1 | 0.303 | 0.816 | 0.046 | -0.252 | 0.020 |
| 1 | 0.862 | 0.736 | -0.124 | -0.213 | 0.054 |
| 1 | 0.975 | 0.635 | -0.116 | -0.166 | 0.056 |
| 1 | 0.935 | 0.763 | -0.065 | -0.199 | 0.032 |
| 1 | 0.897 | 0.703 | -0.111 | -0.214 | 0.063 |
| 1 | 0.697 | 0.821 | -0.085 | -0.210 | 0.052 |
| 1 | 0.789 | 0.724 | -0.075 | -0.205 | 0.049 |
| 1 | 0.701 | 0.700 | -0.073 | -0.166 | 0.025 |
| 1 | 0.676 | 0.765 | -0.110 | -0.149 | 0.018 |
| 1 | 0.433 | 0.666 | 0.109 | -0.136 | 0.032 |
| 1 | 0.910 | 0.776 | -0.315 | -0.154 | 0.016 |
| 1 | 0.557 | 0.781 | -0.099 | -0.220 | 0.041 |
| 1 | 0.923 | 0.873 | -0.105 | -0.146 | 0.044 |
| 1 | 0.628 | 0.845 | -0.101 | -0.248 | 0.048 |
| 1 | 1.060 | 0.705 | -0.141 | -0.167 | 0.050 |
| 1 | 0.897 | 0.598 | -0.167 | -0.198 | 0.053 |
| 1 | 0.143 | 0.845 | -0.269 | -0.243 | 0.063 |
| 1 | 0.635 | 0.807 | -0.185 | -0.218 | 0.032 |

| | | | | | |
|---|---|---|---|---|---|
| 1 | 0.867 | 0.763 | -0.069 | -0.180 | 0.047 |
| 1 | 0.771 | 0.769 | -0.051 | -0.227 | 0.054 |
| 1 | 0.763 | 0.681 | -0.114 | -0.185 | 0.040 |
| 1 | 1.060 | 0.697 | -0.135 | -0.152 | 0.042 |
| 1 | 1.040 | 0.754 | -0.143 | -0.162 | 0.049 |
| 1 | 0.898 | 0.724 | -0.096 | -0.164 | 0.022 |
| 1 | 0.558 | 0.789 | -0.059 | -0.246 | 0.035 |
| 1 | 0.668 | 0.771 | -0.192 | -0.236 | 0.012 |
| 1 | 0.582 | 0.713 | 0.020 | -0.188 | 0.026 |
| 1 | 0.771 | 0.656 | -0.164 | -0.163 | 0.065 |
| 1 | 0.635 | 0.691 | -0.059 | -0.154 | 0.021 |
| 1 | 0.854 | 0.686 | -0.126 | -0.151 | 0.025 |
| 1 | 0.876 | 0.640 | -0.142 | -0.171 | 0.003 |
| 1 | 0.679 | 0.784 | 0.006 | -0.245 | 0.046 |
| 1 | 0.690 | 0.834 | -0.146 | -0.232 | 0.035 |
| 1 | 0.711 | 0.753 | -0.096 | -0.184 | 0.067 |
| 1 | 0.694 | 0.677 | -0.099 | -0.267 | 0.044 |
| 1 | 0.812 | 0.545 | -0.188 | -0.228 | 0.083 |
| 1 | 0.671 | 0.754 | -0.054 | -0.210 | 0.059 |
| 1 | 0.869 | 0.844 | -0.337 | -0.190 | 0.049 |
| 1 | 1.000 | 0.724 | -0.160 | -0.220 | 0.042 |
| 1 | 0.860 | 0.693 | -0.166 | -0.203 | 0.027 |
| 1 | 0.476 | 0.738 | 0.152 | -0.252 | 0.040 |
| 1 | 0.804 | 0.728 | -0.141 | -0.229 | 0.005 |
| 1 | 0.729 | 0.790 | -0.069 | -0.184 | 0.056 |
| 1 | 0.167 | 0.671 | -0.096 | -0.196 | 0.078 |
| 1 | 0.929 | 0.733 | -0.087 | -0.182 | 0.015 |
| 1 | 0.933 | 0.651 | -0.113 | -0.140 | 0.035 |
| 1 | 0.581 | 0.710 | -0.182 | -0.189 | 0.026 |
| 1 | 0.655 | 0.765 | -0.077 | -0.175 | 0.022 |
| 1 | 0.921 | 0.652 | -0.187 | -0.134 | 0.057 |
| 1 | 0.753 | 0.620 | -0.111 | -0.150 | 0.059 |
| 1 | 0.730 | 0.687 | -0.124 | -0.156 | 0.047 |
| 1 | 0.615 | 0.692 | -0.014 | -0.194 | 0.086 |
| 1 | 0.640 | 0.655 | -0.012 | -0.197 | 0.053 |
| 1 | 0.155 | 0.583 | -0.225 | -0.285 | 0.020 |
| 1 | -0.120 | 0.592 | -0.191 | -0.257 | 0.052 |
| 1 | 0.694 | 0.727 | -0.123 | -0.111 | 0.012 |
| 1 | 0.556 | 0.645 | -0.043 | -0.189 | 0.026 |
| 1 | -0.245 | 0.594 | -0.170 | -0.183 | 0.030 |
| 1 | 0.126 | 0.639 | -0.083 | -0.304 | 0.065 |
| 1 | 0.726 | 0.668 | -0.131 | -0.153 | 0.055 |
| 1 | 0.633 | 0.669 | -0.076 | -0.202 | 0.052 |
| 1 | 0.879 | 0.732 | -0.224 | -0.150 | 0.048 |
| 1 | 0.898 | 0.606 | -0.183 | -0.163 | 0.012 |
| 1 | 0.641 | 0.788 | -0.113 | -0.198 | 0.044 |
| 1 | -0.132 | 0.564 | -0.168 | -0.220 | 0.026 |
| 2 | 0.407 | 0.803 | -0.116 | -0.236 | 0.019 |
| 2 | 0.494 | 0.841 | -0.228 | -0.215 | 0.088 |
| 2 | 0.474 | 0.762 | -0.273 | -0.165 | -0.025 |
| 2 | 0.009 | 0.734 | -0.455 | -0.235 | 0.006 |

| | | | | | |
|---|---|---|---|---|---|
| 2 | 0.254 | 0.903 | -0.364 | -0.250 | 0.029 |
| 2 | 0.496 | 0.868 | -0.143 | -0.251 | 0.048 |
| 2 | -0.170 | 0.642 | 0.053 | -0.182 | 0.033 |
| 2 | 0.179 | 0.977 | -0.370 | -0.191 | 0.081 |
| 2 | 0.490 | 0.905 | -0.200 | -0.187 | 0.089 |
| 2 | 0.383 | 0.739 | -0.193 | -0.216 | 0.066 |
| 2 | 0.585 | 0.819 | -0.163 | -0.209 | 0.060 |
| 2 | 0.376 | 0.890 | -0.186 | -0.235 | 0.030 |
| 2 | 0.403 | 0.785 | -0.018 | -0.141 | 0.036 |
| 3 | -0.201 | 0.489 | -0.004 | -0.120 | 0.018 |
| 3 | 0.590 | 0.739 | -0.071 | -0.266 | 0.060 |
| 3 | 0.593 | 0.751 | -0.082 | -0.214 | 0.036 |
| 3 | 0.658 | 0.373 | -0.144 | -0.215 | 0.064 |
| 3 | 0.520 | 0.890 | -0.003 | -0.197 | 0.075 |
| 3 | 0.279 | 0.839 | -0.186 | -0.219 | 0.000 |
| 3 | -0.062 | 0.662 | -0.004 | -0.218 | -0.037 |
| 3 | 0.657 | 0.849 | -0.085 | -0.260 | 0.031 |
| 3 | -0.090 | 0.788 | -0.163 | -0.164 | -0.063 |
| 3 | 0.533 | 0.769 | 0.040 | -0.221 | 0.048 |
| 4 | 0.549 | 0.801 | -0.188 | -0.269 | 0.003 |
| 4 | 0.270 | 0.864 | -0.182 | -0.217 | -0.049 |
| 4 | 0.241 | 0.882 | -0.166 | -0.156 | 0.065 |
| 4 | 0.455 | 0.764 | -0.005 | -0.233 | 0.054 |
| 4 | -0.119 | 0.636 | -0.180 | -0.140 | 0.016 |
| 4 | 0.162 | 0.753 | -0.179 | -0.159 | 0.040 |
| 4 | 0.610 | 0.285 | -0.158 | -0.228 | 0.068 |
| 4 | 0.394 | 0.826 | -0.039 | -0.232 | 0.028 |
| 4 | -0.007 | 0.706 | 0.034 | -0.163 | 0.062 |
| 4 | 0.494 | 0.818 | -0.195 | -0.259 | 0.031 |
| 4 | 0.999 | 0.673 | -0.154 | -0.135 | 0.046 |
| 4 | 0.243 | 0.784 | -0.140 | -0.259 | 0.081 |
| 4 | 0.102 | 0.656 | 0.177 | -0.171 | 0.064 |
| 4 | 0.176 | 0.687 | -0.058 | -0.244 | 0.054 |
| 4 | 0.444 | 0.540 | -0.059 | -0.266 | -0.008 |
| 5 | 0.731 | 0.721 | -0.247 | -0.203 | 0.018 |
| 5 | 0.004 | 0.744 | -0.204 | -0.144 | 0.012 |
| 5 | 0.864 | 0.667 | -0.177 | -0.183 | 0.050 |
| 5 | -0.023 | 0.653 | -0.274 | -0.144 | -0.129 |
| 5 | 0.671 | 0.729 | 0.059 | -0.158 | 0.048 |
| 5 | 0.622 | 0.823 | -0.079 | -0.172 | 0.052 |
| 5 | 0.495 | 0.677 | -0.069 | -0.142 | 0.045 |
| 5 | 0.759 | 0.780 | -0.097 | -0.250 | 0.025 |
| 5 | 0.581 | 0.835 | -0.080 | -0.207 | 0.035 |
| 5 | 0.782 | 0.539 | -0.088 | -0.211 | 0.007 |
| 5 | 0.242 | 0.812 | -0.253 | -0.244 | 0.067 |
| 5 | -0.019 | 0.932 | -0.074 | -0.118 | -0.131 |
| 5 | 0.194 | 0.990 | -0.170 | -0.168 | -0.026 |
| 5 | 0.682 | 1.080 | -0.110 | -0.099 | 0.095 |
| 5 | 0.750 | 0.848 | -0.108 | -0.183 | 0.016 |
| 5 | 0.274 | 0.748 | -0.135 | -0.177 | -0.021 |
| 5 | 0.510 | 0.785 | -0.090 | -0.151 | 0.033 |

| | | | | | |
|---|---|---|---|---|---|
| 5 | 0.533 | 0.781 | -0.053 | -0.257 | 0.069 |
| 5 | 0.468 | 0.903 | -0.216 | -0.185 | 0.049 |
| 5 | 0.747 | 0.733 | 0.027 | -0.273 | 0.027 |
| 5 | 0.593 | 0.746 | 0.072 | -0.242 | 0.035 |
| 5 | 0.570 | 0.841 | -0.065 | -0.162 | 0.041 |
| 5 | 0.451 | 0.709 | -0.052 | -0.199 | 0.006 |
| 6 | 0.499 | 0.458 | 0.002 | -0.240 | 0.081 |
| 6 | 0.015 | 0.779 | -0.226 | -0.126 | 0.069 |
| 6 | 0.427 | 0.809 | -0.164 | -0.204 | 0.055 |
| 6 | 0.760 | 0.745 | -0.267 | -0.175 | 0.051 |
| 6 | 0.262 | 0.734 | -0.141 | -0.294 | -0.078 |
| 6 | 0.825 | 0.724 | -0.006 | -0.153 | 0.040 |
| 6 | 0.389 | 0.767 | -0.072 | -0.268 | 0.073 |
| 6 | -0.249 | 0.494 | -0.049 | -0.104 | 0.052 |
| 6 | 0.698 | 0.770 | 0.038 | -0.118 | 0.030 |
| 6 | 0.255 | 0.910 | -0.258 | -0.261 | 0.024 |
| 6 | 0.178 | 0.854 | -0.178 | -0.207 | 0.024 |
| 6 | 0.857 | 0.784 | -0.122 | -0.242 | 0.050 |
| 6 | 0.402 | 0.813 | -0.063 | -0.157 | 0.043 |
| 6 | 0.677 | 0.632 | -0.088 | -0.153 | 0.052 |
| 6 | 0.485 | 0.900 | -0.112 | -0.182 | 0.083 |
| 6 | 0.610 | 0.765 | -0.104 | -0.241 | 0.046 |
| 6 | 0.271 | 0.752 | -0.104 | -0.250 | 0.024 |
| 6 | 0.498 | 0.801 | -0.156 | -0.235 | 0.047 |
| 6 | 0.405 | 0.790 | 0.034 | -0.223 | 0.055 |
| 6 | 0.165 | 0.499 | -0.127 | -0.037 | 0.107 |
| 6 | 0.582 | 0.755 | -0.166 | -0.159 | 0.039 |
| 6 | 0.352 | 0.689 | -0.041 | -0.145 | 0.039 |
| 6 | 0.413 | 0.805 | -0.068 | -0.245 | 0.067 |
| 6 | 0.065 | 0.689 | 0.089 | -0.153 | 0.038 |
| 6 | 0.364 | 0.845 | -0.212 | -0.256 | 0.079 |
| 6 | 0.261 | 0.720 | 0.055 | -0.232 | 0.054 |
| 6 | 0.538 | 0.802 | -0.074 | -0.253 | 0.071 |
| 6 | 0.526 | 0.615 | -0.049 | -0.174 | 0.050 |
| 6 | 0.397 | 0.778 | 0.019 | -0.201 | 0.059 |
| 6 | 0.292 | 0.758 | 0.000 | -0.217 | 0.052 |
| 6 | 0.433 | 0.797 | -0.322 | -0.248 | 0.037 |
| 6 | 0.635 | 0.803 | -0.116 | -0.195 | 0.064 |
| 6 | -0.064 | 0.813 | -0.203 | -0.183 | -0.045 |
| 6 | 0.254 | 0.733 | -0.091 | -0.194 | 0.050 |
| 6 | 0.037 | 0.671 | -0.260 | -0.106 | 0.115 |

What is claimed is:

1. A method of classifying a sample of tissue of a mammalian anatomical structure, the tissue of which may have various morphological and biochemical states, comprising:
   illuminating the sample with electromagnetic radiation wavelengths of about 337 nm, about 380 nm and about 460 nm to produce fluorescence therein having spectral characteristics indicative of a tissue classification relating to different epithelial tissues ranging from normal to neoplastic and inflammation;
   detecting a plurality of discrete emission wavelengths from the fluorescence; and
   calculating from the emission wavelengths a probability that the sample belongs in the tissue classification.

2. The method of claim 1, wherein the illumination wavelengths are in the ranges of 317–357 nm, 360–400 nm and 440–480 nm.

3. The method of claim 1, wherein the emission wavelengths are about 410 nm, about 460 nm, about 510 nm and about 580 nm for an illumination of about 337 nm; about 460 nm, about 510 nm, about 580 nm, about 600 nm and about 640 nm for an illumination of about 380 nm; and about 510, about 580 nm, about 600 nm, about 620 nm, about 640 nm and about 660 nm for an illumination of about 460 nm.

4. The method of claim 1, wherein the sample is illuminated in vitro.

5. The method of claim 1, wherein the sample is illuminated in vivo.

6. The method of claim 4, further comprising obtaining the sample by biopsy.

7. The method of claim 6, wherein the obtaining step further comprises generating a monolayer cell touch preparation or a pellet.

8. The method of claim 7, wherein the obtaining step further comprises ethanol fixation of the tissue sample.

9. The method of claim 1, wherein the illuminating comprises illuminating the sample substantially normal to a surface of the sample, and wherein the detecting step comprises detecting the spectra at an angle of approximately 20° from normal.

10. The method of claim 1, wherein the calculating step includes discriminating SIL from normal squamous epithelia.

11. The method of claim 1, wherein the calculating step includes discriminating SIL from normal columnar epithelium.

12. The method of claim 1, wherein the calculating step includes discriminating SIL from inflamed tissue.

13. The method of claim 1, wherein the calculating step includes discriminating high grade SIL tissue from low grade SIL tissue.

14. The method of claim 1, wherein the calculating step includes discriminating high grade SIL from normal tissue.

15. The method of claim 1, wherein the calculating step includes discriminating SIL from non-SIL.

16. The method of claim 1, wherein the calculating step includes discriminating high grade SIL from non-high grade SIL.

17. A method of developing a model for differentiating between tissue classifications for a tissue sample, the tissue classifications relating to different epithelial tissues ranging from normal to neoplastic and inflammation, comprising:
   providing a plurality of tissue samples belonging to the tissue classifications;
   illuminating the samples with electromagnetic radiation wavelengths of about 337 nm, about 380 nm and about 460 nm to produce fluorescence therein;
   detecting a plurality of discrete emission wavelengths from the fluorescence;
   forming from the emission wavelengths a set of principal components that provide statistically significant differences between the tissue classifications; and
   incorporating the principal components into a logistic discriminant analysis to develop a relevant model for differentiating between the tissue classifications.

18. The method of claim 17, wherein the illumination wavelengths are in the ranges of 317–357 nm, 360–400 nm and 440–480 nm.

19. The method of claim 17, wherein the emission wavelengths are:
   about 410 nm, about 460 nm, about 510 nm and about 580 nm for an illuminating wavelength of about 337 nm;
   about 460 nm, about 510 nm, about 580 nm, about 600 nm and about 640 nm for an illuminating wavelength of about 380 nm; and
   about 510, about 580 nm, about 600 nm, about 620 nm, about 640 nm and about 660 nm for an illuminating wavelength of about 460 nm.

20. A method of classifying a sample of tissue of a mammalian anatomical structure, the tissue of which may have various morphological and biochemical states, comprising:
   illuminating the sample with electromagnetic radiation wavelengths of about 337 nm, about 380 nm and about 460 nm to produce fluorescence having spectral characteristics indicative of a tissue classification relating to different epithelial tissues ranging from normal to neoplastic and inflammation;
   detecting a plurality of emission wavelengths from the fluorescence;
   obtaining principal components PC1, PC3 and PC7 from the emission wavelengths; and
   establishing from the principal components PC1, PC3 and PC7 a probability that the sample belongs in the tissue classification.

21. A method of classifying a sample of tissue of a mammalian anatomical structure, the tissue of which may have various morphological and biochemical states, comprising:
   illuminating the sample with electromagnetic radiation wavelengths of about 337 nm, about 380 nm and about 460 nm to produce fluorescence having spectral characteristics indicative of a tissue classification relating to different epithelial tissues ranging from normal to neoplastic and inflammation;
   detecting a plurality of emission wavelengths from the fluorescence;
   obtaining principal components PC1, PC2, PC4, and PC5 from the emission wavelengths; and
   establishing from the principal components PC1, PC2, PC4 and PC5 a probability that the sample belongs in the tissue classification.

22. A method of classifying a sample of tissue of a mammalian anatomical structure, the tissue of which may have various morphological and biochemical states, comprising:
   illuminating the sample with electromagnetic radiation wavelengths of about 337 nm, about 380 nm and about 460 nm to produce fluorescence having spectral characteristics indicative of a tissue classification relating to different epithelial tissues ranging from normal to neoplastic and inflammation;

detecting a plurality of emission wavelengths from the fluorescence;

obtaining principal components PC1, PC3, PC6, and PC8 from the emission wavelengths; and establishing from the principal components PC1, PC3 PC6 and PC8 a probability that the sample belongs in the tissue classification.

23. A method of classifying a tissue of a patient in a particular one of a plurality of tissue classifications relating to different epithelial tissues ranging from normal to neoplastic and inflammation, comprising:

identifying the patient with a predetermined population having a prior probability of tissue belonging to the particular tissue classification;

applying a plurality of excitation wavelengths to a plurality of locations on the tissue of the patient;

obtaining from the applications of the excitation wavelengths in the applying step respective sets of fluorescence spectral data, each comprising a plurality of discrete emission wavelengths;

preprocessing the sets of fluorescence spectral data;

concatenating the preprocessed fluorescence spectral data into respective vectors for the tissue locations;

processing the vectors with a matrix of reduced eigenvectors that display statistically significant differences for the tissue classifications in the population; and calculating a posterior probability for each of the locations on the tissue of the patient that the tissue belongs to the particular tissue classification from the processed vectors, from the prior probabilities, and from distribution functions of principal component scores for the tissue classifications in the population.

24. A method as in claim 23, wherein the emission wavelengths are:

about 410 nm, about 460 nm, about 510 nm and about 580 nm for an excitation wavelength of about 337 nm;

about 460 nm, about 510 nm, about 580 nm, about 600 nm and about 640 nm for an excitation wavelength of about 380 nm; and about 510, about 580 nm, about 600 mn, about 620 nm, about 640 nm and about 660 nm for an excitation wavelength of about 460 nm.

25. A method as in claim 23 further comprising displaying the tissue of the patient graphically, wherein locations on the tissue of the patient having a posterior probability greater than a predetermined threshold are displayed in a different color than locations on the tissue of the patient having a posterior probability less than the predetermined threshold.

26. A method of developing an index for calculating a probability that a tissue of a living organism belongs to one of a plurality of tissue classifications relating to different epithelial tissues ranging from normal to neoplastic and inflammation, comprising:

applying a plurality of excitation wavelengths to a plurality of tissue sites in a sample population, each of the histo-pathologic tissue classifications having a prior probability of occurring in the sample population;

obtaining from the applications of the excitation wavelengths in the applying step respective sets of spectral data of fluorescence intensities at discrete emission wavelengths;

forming a first dimensionally reduced set of vectors from the sets of spectral data that shows statistically significant differences between a first one and a second one of the histo-pathologic tissue classifications and accounts for a significant amount of variation in collectively the sets of spectral data;

calculating first probability distribution functions for the tissue classifications from the first dimensionally reduced set of vectors;

forming a second dimensionally reduced set of vectors from the sets of spectral data that shows statistically significant differences between a third one and a fourth one of the histo-pathologic tissue classifications and accounts for a significant amount of variation in collectively the sets of spectral data;

calculating second probability distribution functions for the tissue classifications from the second dimensionally reduced set of vectors; and finishing the first and second probability distribution functions and the first and second dimensionally reduced set of vectors as the index.

27. A method as in claim 26, wherein the emission wavelengths are:

about 410 nm, about 460 nm, about 510 nm and about 580 nm for an excitation wavelength of about 337 nm;

about 460 nm, about 510 nm, about 580 mn, about 600 nm and about 640 nm for an excitation wavelength of about 380 nm; and about 510, about 580 nm, about 600 nm, about 620 nm, about 640 nm and about 660 nm for an excitation wavelength of about 460 nm.

28. The method of claim 26 further comprising the step of preprocessing the sets of spectral data prior to the step of forming a first dimensionally reduced set of vectors and prior to the step of forming a second dimensionally reduced set of vectors to reduce variations in spectral data from each organism and from different organisms of the population, wherein:

the tissue classifications comprise two histo-pathologic tissue classifications;

the plurality of excitation wavelengths comprises about 337 nm, about 380 nm, and about 460 nm;

the step of forming a first dimensionally reduced set of vectors comprises principal component analysis; and the step of forming a second dimensionally reduced set of vectors comprises principal component analysis.

29. A method of identifying a probability of a particular tissue classification for tissue of a patient having a plurality of possible tissue classifications relating to different epithelial tissues ranging from normal to neoplastic and inflammation, comprising:

identifying the patient with a predetermined population having prior probabilities of the possible tissue classifications therein;

applying electromagnetic radiation at a plurality of wavelengths to a plurality of tissue sites of subjects in the population and to the tissue of the patient;

obtaining respective sets of subject fluorescence spectral data from the electromagnetic radiation applying step;

preprocessing the sets of subject fluorescence spectral data to reduce inter-patient and intra-patient variation therein;

forming a dimensionally reduced set of orthogonal linear combinations of emission variables, including a reduced eigenvector matrix, that shows statistically significant differences between the possible tissue classifications and that significantly accounts for variation in the preprocessed sets of subject fluorescence spectral data;

calculating subject scores of the dimensionally reduced set of orthogonal linear combinations from the preprocessed sets of subject fluorescence spectral data for the possible tissue classifications;

obtaining respective sets of patient fluorescence spectral data from the electromagnetic radiation applying step;

preprocessing the sets of patient fluorescence spectral data to reduce intra-patient variation therein;

concatenating the preprocessed patient fluorescence spectral data into vectors;

processing the vectors with the reduced eigenvector matrix to obtain patient scores; and calculating a posterior probability of the particular tissue classification from the subject scores, from the patient scores, and from the prior probability.

30. The method of claim 29, wherein the step of forming a dimensionally reduced set of orthogonal linear combinations of emission variables comprises:

forming principal components and principle component scores from the preprocessed sets of subject fluorescence spectral data;

retaining eigenvalues from the principal components forming step that account for a significant amount of the variation in the preprocessed sets of subject fluorescence spectral data;

calculating the diagnostic contribution of each of the principle components for the retained eigenvalues; and retaining the eigenvalues corresponding to the principle components identified in the diagnostic contribution calculating step as having a significant diagnostic contribution.

31. The method of claim 30, wherein the posterior probability calculating step comprises calculating posterior probability using logistic discrimination.

32. The method of claim 31, wherein the diagnostic contribution calculating step comprises calculating the diagnostic contribution using a Student's T-Test.

33. The method of claim 30, wherein:

the subject fluorescence spectral data obtaining step comprises obtaining respective sets of subject fluorescence spectral data from the electromagnetic radiation applying step at respective first, second and third sets of discrete wavelengths at which component loadings for the principle components identified in the diagnostic contribution calculating step as having a significant diagnostic contribution are significant; and the patient fluorescence spectral data obtaining step comprises obtaining respective sets of patient fluorescence spectral data from the electromagnetic radiation applying step at the first, second, and third sets of discrete wavelengths.

34. The method of claim 33, wherein:

the first wavelength is about 337 nm and the first set of discrete wavelengths is about 410 about 430 nm, about 510 nm, and about 580 nm;

the second wavelength is about 380 nm, and the second set of discrete wavelengths is about 410 nm, about 430 nm, about 510 nm, about 580 nm, and about 640 nm; and the third wavelength is about 460 nm, and the third set of discrete wavelengths is about 580 nm, about 600 nm, about 620 nm, and about 640 nm.

35. A method as in claim 29 further comprising displaying the tissue of the patient graphically, wherein locations on the tissue of the patient having a posterior probability greater than a predetermined threshold are displayed in a different color than locations on the tissue of the patient having a posterior probability less than the predetermined threshold.

* * * * *

UNITED STATES PATENT AND TRADEMARK OFFICE
CERTIFICATE OF CORRECTION

| | | |
|---|---|---|
| PATENT NO. | : 6,258,576 B1 | Page 1 of 1 |
| DATED | : July 10, 2001 | |
| INVENTOR(S) | : Rebecca Richards-Kortum, Nirmala Ramanujam, Anita-Mahadevan-Jansen Michele Follen Mitchell | |

It is certified that error appears in the above-identified patent and that said Letters Patent is hereby corrected as shown below:

<u>Column 87,</u>
Line 53, please add "histo-pathologic" after "plurality of".

Signed and Sealed this

Twenty-fourth Day of December, 2002

JAMES E. ROGAN
*Director of the United States Patent and Trademark Office*